(12) United States Patent
Hodorek et al.

(10) Patent No.: US 10,849,762 B1
(45) Date of Patent: Dec. 1, 2020

(54) IMPLANTS, SYSTEMS AND METHODS OF USING THE SAME

(71) Applicant: IGNITE ORTHOPEDICS LLC, Warsaw, IN (US)

(72) Inventors: Brian C. Hodorek, Winona Lake, IN (US); Matthew J. Purdy, Winona Lake, IN (US); Russ M. Parrott, Winona Lake, IN (US); J. Michael Wiater, Beverly Hills, MI (US); Anand M. Murthi, Baltimore, MD (US); Matthew J. Smith, Columbia, MO (US); Derek J. Cuff, Venice, FL (US); Andrew Jawa, Cambridge, MA (US); Luke Austin, Haddonfield, NJ (US)

(73) Assignee: IGNITE ORTHOPEDICS LLC, Warsaw, IN (US)

( * ) Notice: Subject to any disclaimer, the term of this patent is extended or adjusted under 35 U.S.C. 154(b) by 0 days.

(21) Appl. No.: 16/947,316

(22) Filed: Jul. 28, 2020

Related U.S. Application Data

(63) Continuation of application No. 16/799,057, filed on Feb. 24, 2020, now Pat. No. 10,722,373, which is a continuation of application No. PCT/US2019/043983, filed on Jul. 29, 2019.

(60) Provisional application No. 62/711,500, filed on Jul. 28, 2018, provisional application No. 62/711,416, filed on Jul. 27, 2018.

(51) Int. Cl.
*A61F 2/40* (2006.01)
*A61F 2/30* (2006.01)

(52) U.S. Cl.
CPC ........ *A61F 2/4014* (2013.01); *A61F 2/30749* (2013.01); *A61F 2002/30383* (2013.01); *A61F 2002/30428* (2013.01); *A61F 2002/4022* (2013.01)

(58) Field of Classification Search
CPC ...... A61F 2/40; A61F 2/4014; A61F 2/30749; A61F 2/4003; A61F 2/4081; A61F 2002/4018; A61F 2002/30904; A61F 2002/30878; A61F 2002/30884
See application file for complete search history.

(56) References Cited

U.S. PATENT DOCUMENTS

| 5,910,171 A | 6/1999 | Kummer |
| 6,228,120 B1 | 5/2001 | Leonard |

(Continued)

FOREIGN PATENT DOCUMENTS

| CN | 203074933 | 7/2013 |
| EP | 2564814 | 3/2013 |

(Continued)

OTHER PUBLICATIONS

International Search Report and Written Opinion of the International Searching Authority for PCT/US2019/043983, dated Dec. 27, 2019, 18 pages.

*Primary Examiner* — Brian A Dukert
(74) *Attorney, Agent, or Firm* — Heslin Rothenberg Farley & Mesiti P.C.; Jacquelyn A. Graff, Esq.

(57) ABSTRACT

Implants, device, systems and methods for replacing an articulation surface in a joint, for example, shoulder prostheses with stemless humeral components or stemmed humeral components. Methods for using the shoulder prostheses with stemless humeral components or stemmed humeral components are also disclosed.

32 Claims, 54 Drawing Sheets

(56) References Cited

U.S. PATENT DOCUMENTS

| | | |
|---|---|---|
| 6,626,946 B1 | 9/2003 | Walch |
| 6,673,114 B2 | 1/2004 | Hartdegen |
| 6,736,852 B2 | 5/2004 | Callaway |
| 6,942,699 B2 | 9/2005 | Stone |
| 8,002,838 B2 | 8/2011 | Klotz |
| 8,512,410 B2 | 8/2013 | Metcalfe |
| 8,845,742 B2 | 9/2014 | Kusogullari |
| 9,510,951 B2 | 12/2016 | Bachmaier |
| 9,700,437 B2 * | 7/2017 | Anthony ............ A61B 17/1684 |
| 9,956,083 B2 | 5/2018 | Humphrey |
| 9,962,266 B2 | 5/2018 | Humphrey |
| 10,010,424 B2 | 7/2018 | Ekelund et al. |
| 10,226,349 B2 | 3/2019 | Sperling et al. |
| 10,433,969 B2 | 10/2019 | Humphrey |
| 2001/0049561 A1 | 12/2001 | Dews |
| 2002/0156534 A1 | 10/2002 | Grusin |
| 2007/0173945 A1 | 7/2007 | Wiley |
| 2010/0114326 A1 | 5/2010 | Winslow |
| 2011/0060417 A1 | 3/2011 | Simmen |
| 2012/0172996 A1 | 7/2012 | Ries |
| 2013/0261629 A1 | 10/2013 | Anthony |
| 2015/0265411 A1 | 9/2015 | Deransart et al. |
| 2017/0105843 A1 | 4/2017 | Britton |
| 2017/0304063 A1 | 10/2017 | Hatzidakis et al. |
| 2017/0340449 A1 | 11/2017 | Deransart et al. |
| 2018/0092760 A1 | 4/2018 | Sperling et al. |
| 2018/0214276 A1 | 8/2018 | Humphrey |
| 2018/0280151 A1 | 10/2018 | Humphrey |
| 2018/0280152 A1 | 10/2018 | Mutchler et al. |

FOREIGN PATENT DOCUMENTS

| | | |
|---|---|---|
| EP | 3045149 | 5/2017 |
| EP | 2965720 | 7/2017 |
| EP | 3335675 | 6/2018 |
| WO | 2008050091 | 5/2008 |
| WO | 2014005644 | 1/2014 |
| WO | 2018022227 | 2/2018 |
| WO | 2018039493 | 3/2018 |

* cited by examiner

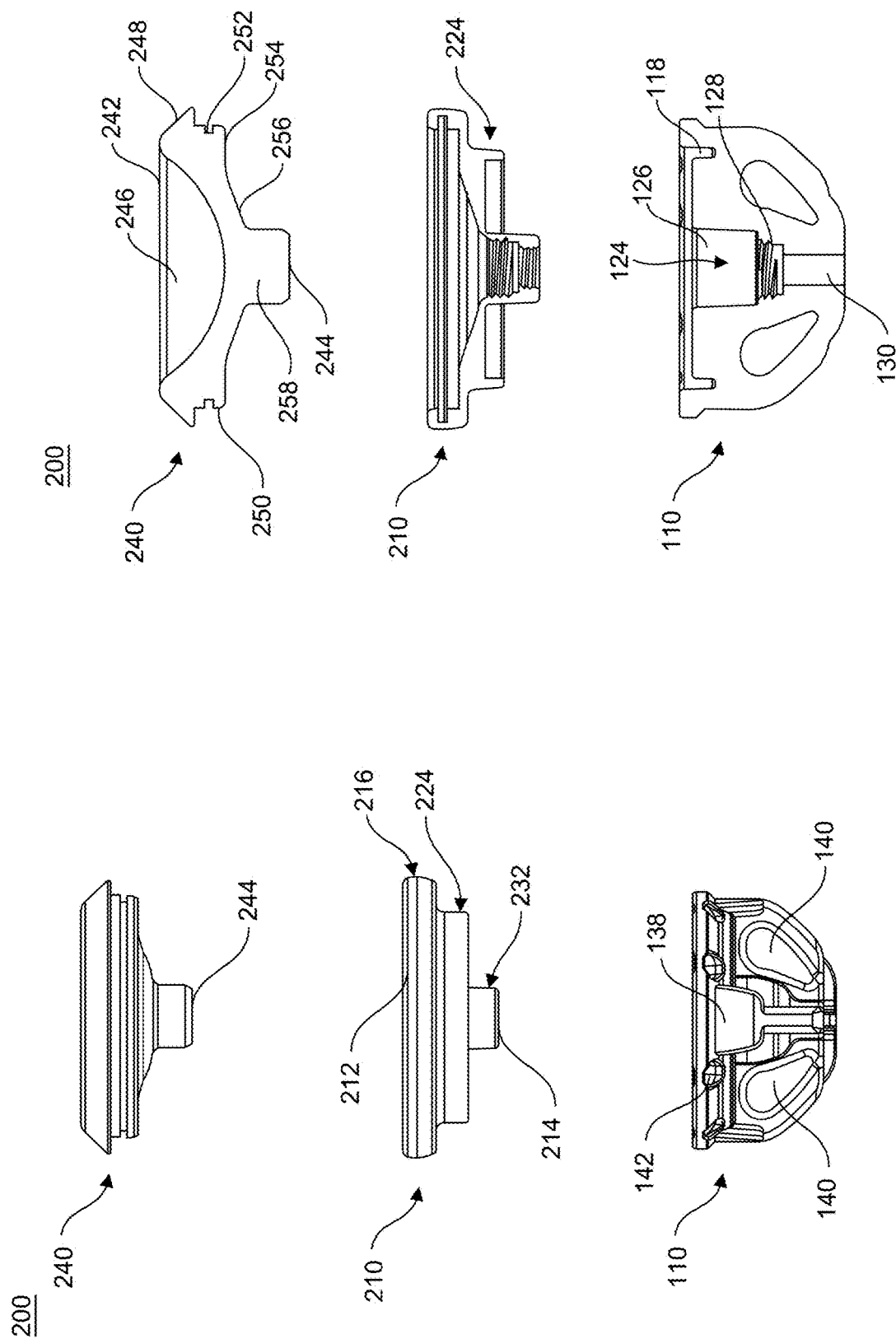

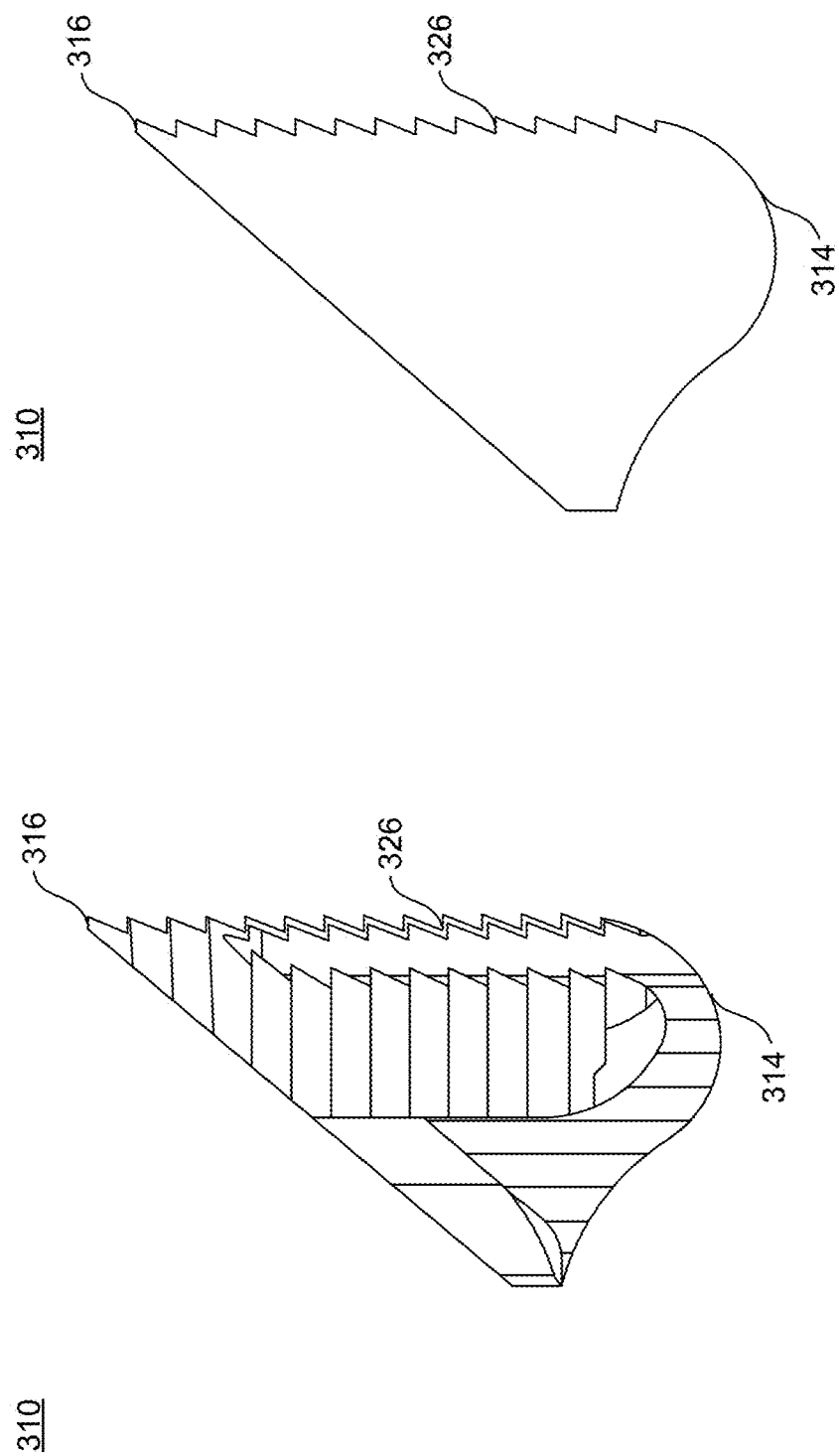

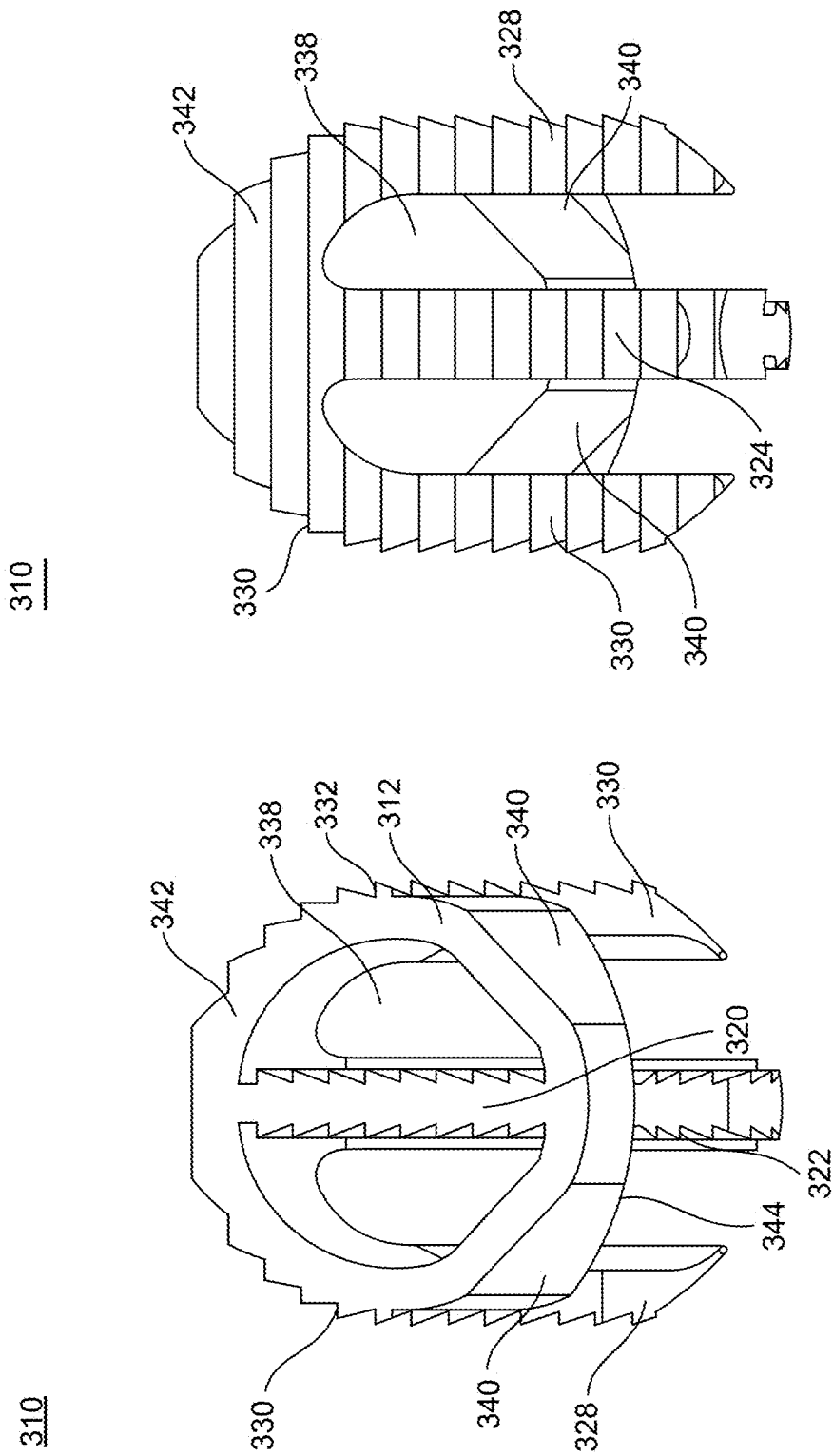

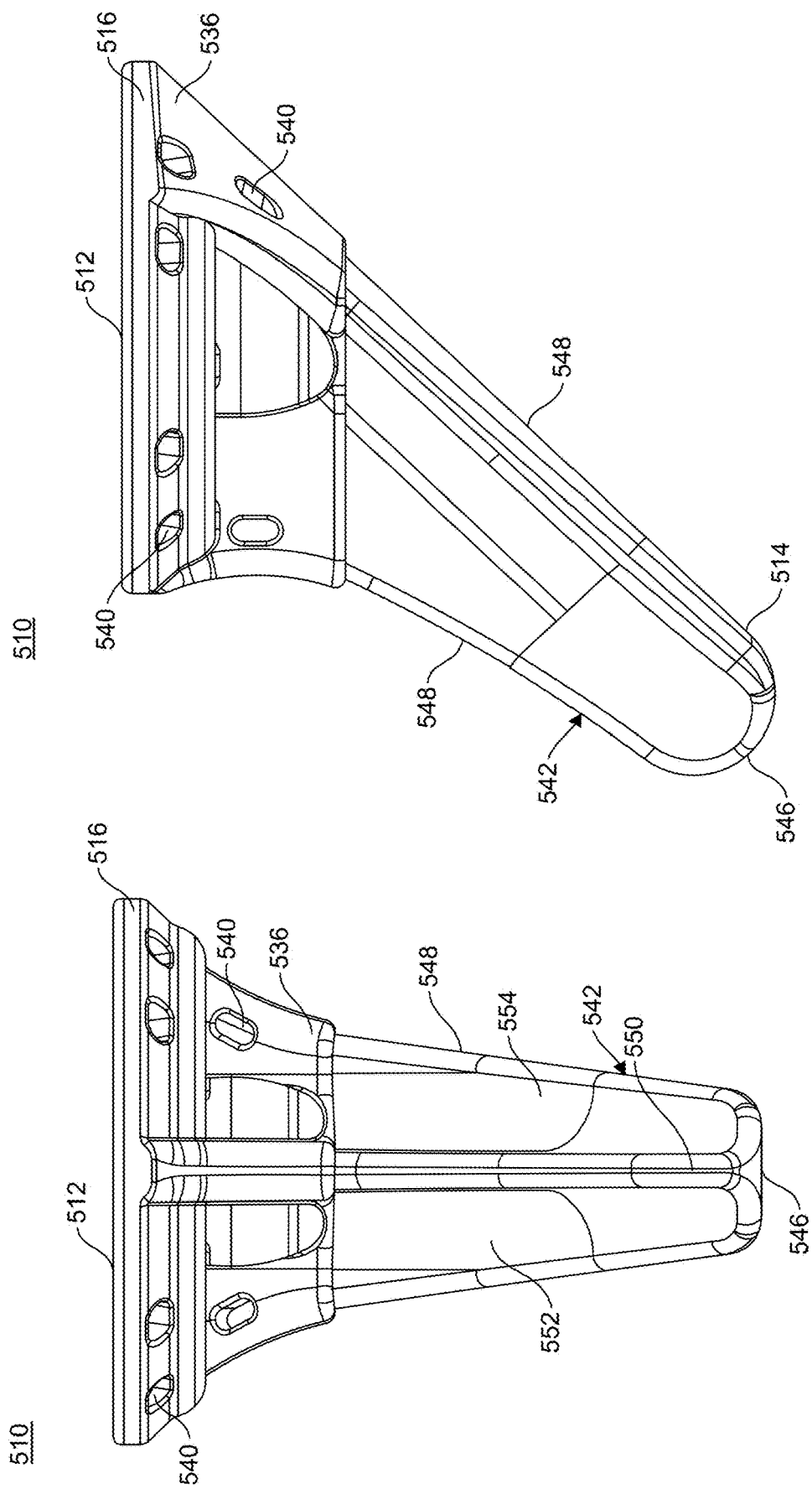

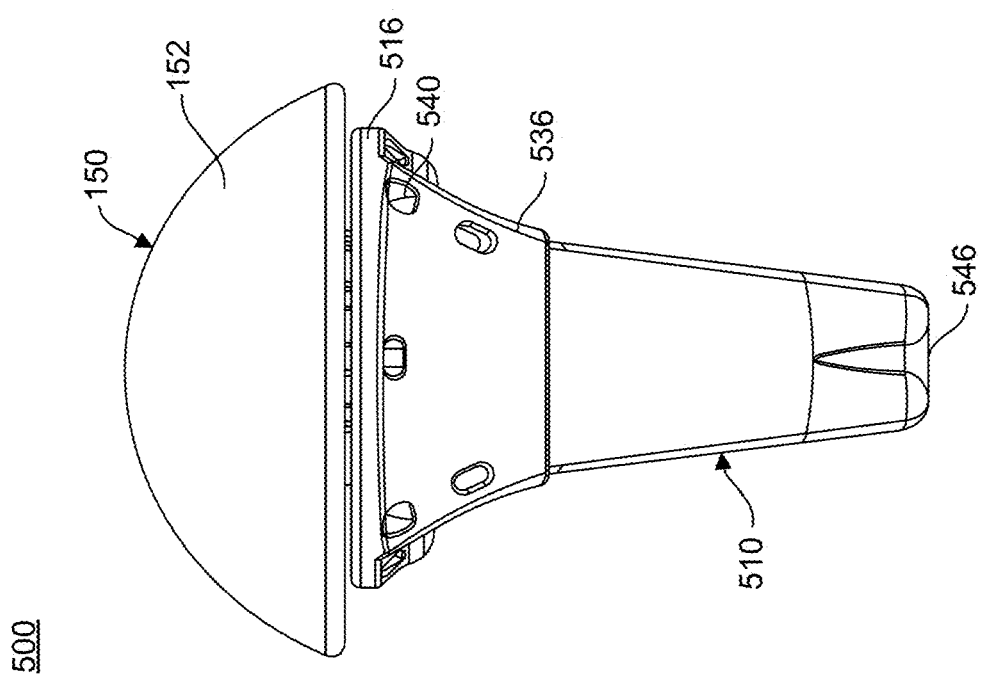
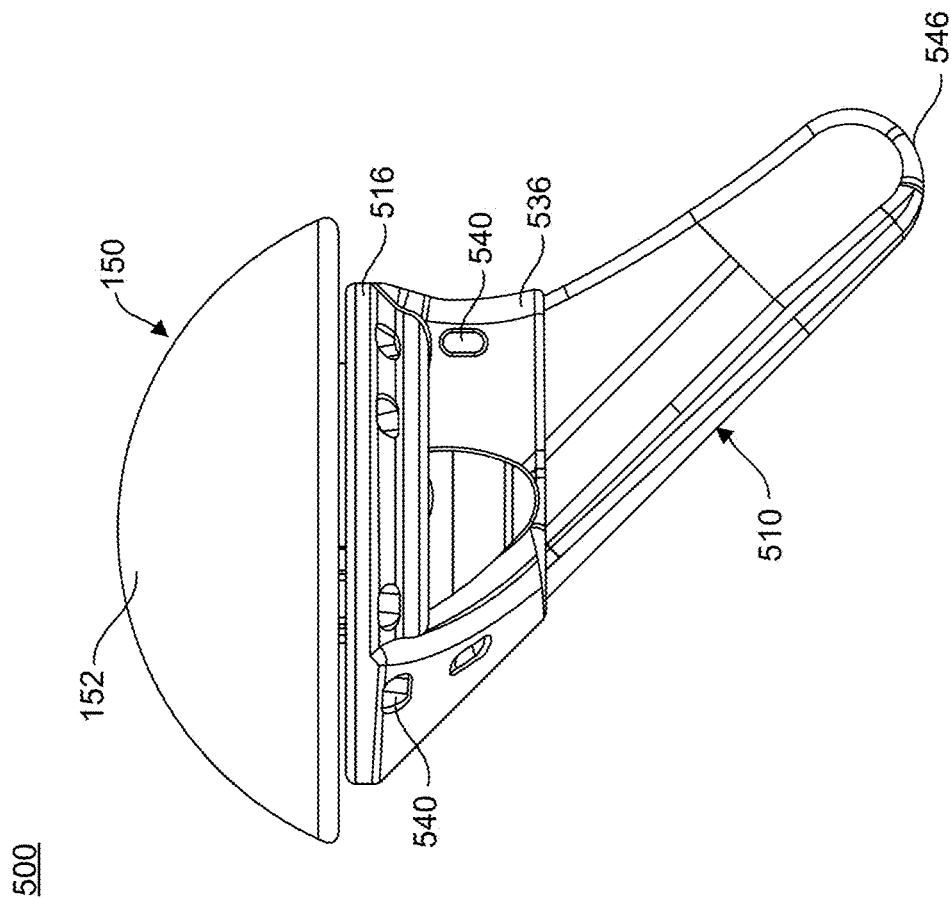

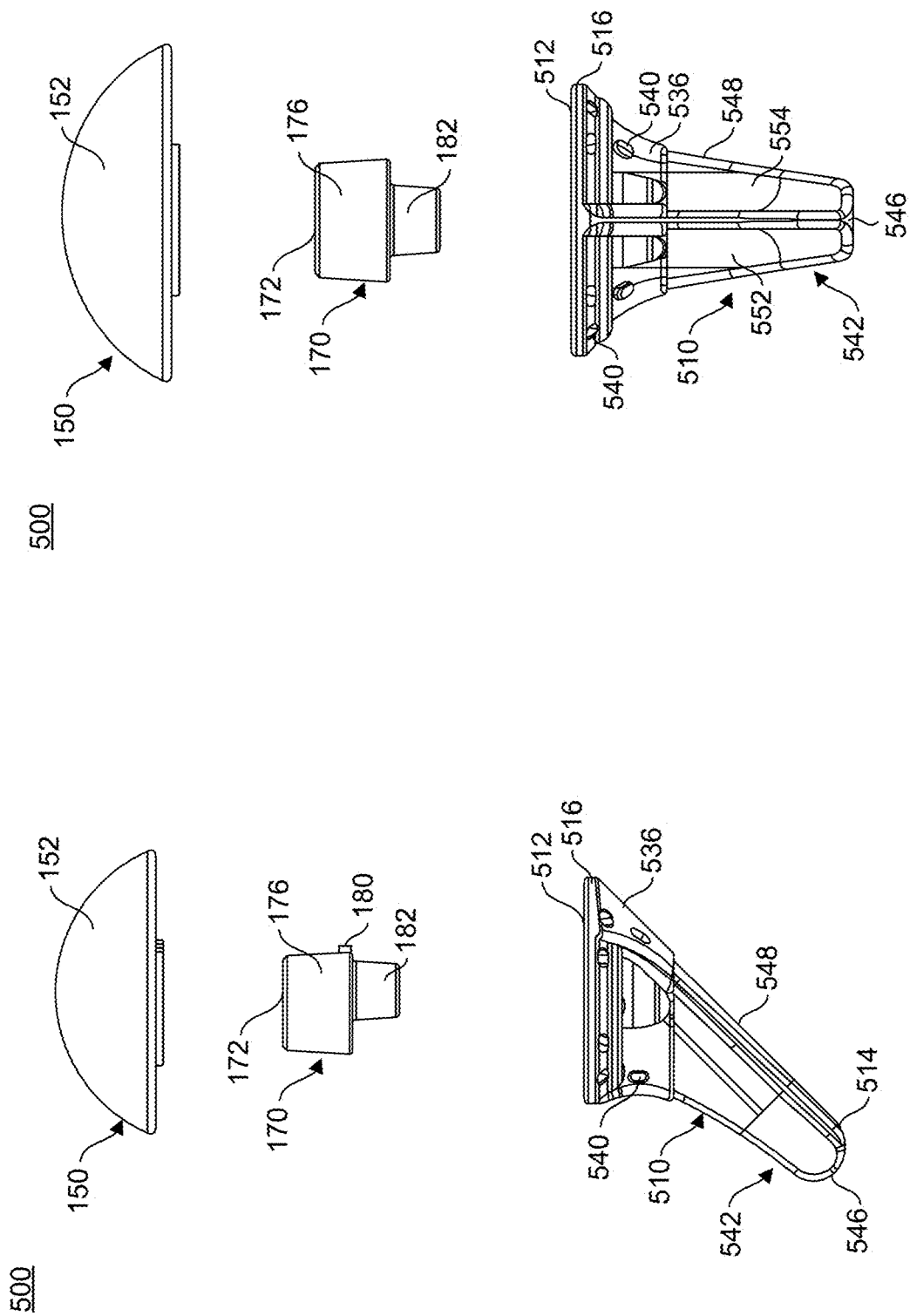

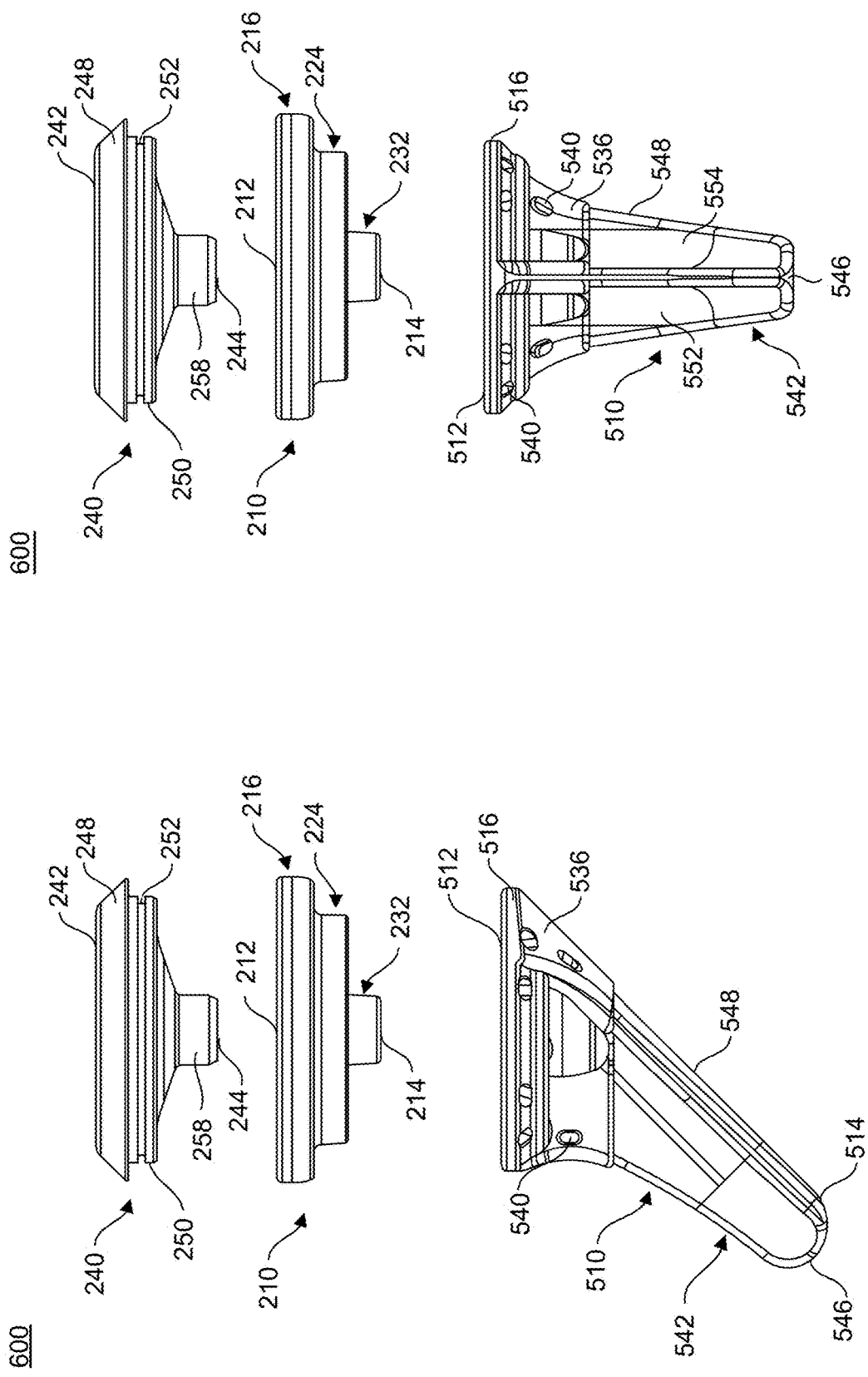

IMPLANTS, SYSTEMS AND METHODS OF USING THE SAME

CROSS-REFERENCE TO RELATED APPLICATION

This application is a continuation of U.S. patent application Ser. No. 16/799,057 filed Feb. 24, 2020 and entitled Implants, Systems and Methods of Using Same, which issues as U.S. Pat. No. 10,722,373 on Jul. 28, 2020, which is a continuation of PCT/US2019/043983 filed Jul. 29, 2019 and entitled Implants, Systems and Methods of Using Same, which claims priority benefit under 35 U.S.C. § 119(e) of U.S. provisional application No. 62/711,416 filed Jul. 27, 2018 and entitled Stemless Orthopedic Humeral Implant and U.S. Provisional Application No. 62/711,500 filed Jul. 28, 2018 and entitled Orthopedic Shoulder Implant, which are incorporated herein by reference in their entireties.

FIELD OF THE INVENTION

The present invention relates generally to general surgery, orthopedic implants used for replacing an articulation surface in a joint, such as shoulder prostheses. More specifically, but not exclusively, the present invention relates to shoulder prostheses with stemless humeral components and stemmed humeral components, as well as methods for using the same.

BACKGROUND OF THE INVENTION

Shoulder replacement is a surgical procedure in which all or part of the glenohumeral joint is replaced by a prosthetic implant. Such joint replacement surgery generally is conducted to relieve arthritis pain or fix severe physical joint damage.

Shoulder replacement surgery is an option for treatment of severe arthritis of the shoulder joint. Arthritis is a condition that affects the cartilage of the joints. As the cartilage lining wears away, the protective lining between the bones is lost. When this happens, painful bone-on-bone arthritis develops. Severe shoulder arthritis is quite painful, and it can cause restriction of motion. While this may be tolerated with some medications and lifestyle adjustments, there may come a time when surgical treatment is necessary.

There are a few major approaches to access the shoulder joint. The first is the deltopectoral approach, which saves the deltoid, but requires the subscapularis to be cut. The second is the trans deltoid approach, which provides a straight on approach at the glenoid. However, during this approach the deltoid is put at risk for potential damage.

Shoulder replacement, also known as shoulder arthroplasty or glenohumeral arthroplasty, was pioneered by the French surgeon Jules Emile Péan in 1893. His procedure consisted of physically smoothing the shoulder joint and implanting platinum and rubber materials. The next notable case in the evolution of shoulder replacement procedures was in 1955 when Charles Neer conducted the first hemiarthroplasty, essentially replacing only the humeral head, leaving the natural shoulder socket, or glenoid, intact. This procedure grew exponentially in popularity as time progressed; however, patients often developed cartilage loss on their glenoid surface as well, leading to pain and glenoid erosion. This prompted the development of a procedure to replace not only the humeral component, but the glenoid component as well.

Throughout the development of the procedures, it became well accepted that the rotator cuff muscles were essential to producing the best outcomes in terms of strength, range of motion, and a decrease in pain. In addition to this finding, physical constraints of the normal ball-and-socket anatomy of the shoulder limited most developments in one way or another. For example, a heavily constrained system limited range of motion and the inherent anatomy of the glenoid proved difficult to cement prosthetics and fixate components without fracturing it. These challenges and high rates of failure led to the development of the reverse total shoulder arthroplasty to overcome the limitations imposed by the natural shoulder anatomy.

The 1970s saw an exponential increase in surgical approaches using this methodology, and the number and variation of surgical techniques are many. However, in 1985 Paul Grammont emerged with a superior technique that is the basis for most reverse shoulder replacement procedures today.

In traditional total shoulder arthroplasty, the approach begins with separating the deltoid muscle from the pectoral muscles, facilitating access to the shoulder (glenohumeral) joint through a relatively nerve free passageway. The shoulder joint is initially covered by the rotator cuff muscles (subscapularis, supraspinatus, infraspinatus & teres minor) and the joint capsule (glenohumeral ligaments). Typically, a single rotator cuff muscle is identified and cut to allow direct access to the shoulder joint. At this point, the surgeon can remove the arthritic portions of the joint and then secure the ball and socket prostheses within the joint.

The development of safer, more effective techniques has led to increased use of reverse total shoulder arthroplasty. Reverse total shoulder arthroplasties are typically indicated when the rotator cuff muscles are severely damaged.

Generally, a stemless shoulder prosthesis includes a metaphysical fixation device for fixing the prosthesis to a resected humerus bone. The fixation device includes a base portion and anchoring means, with a humeral head being fixed to the base portion, for example through a taper or screw connection.

Unlike shoulder prostheses having a stem, also referred to as stemmed shoulder prostheses, stemless shoulder prostheses do not make use of the humeral canal in the diaphysis of the humerus. In other words, stemless shoulder prostheses do not rely on their fixation in said canal and an anchoring means extending deep into said canal is therefore not provided. This bears the advantage that it is in general not necessary to prepare the humeral canal for the insertion of the prosthesis and consequently bone is conserved.

Moreover, while conventional shoulder prosthetics used during shoulder arthroplasty adequately provide the patient with an increased range of motion, conventional shoulder prosthetics require insertion of a stem into the humeral canal of the humerus, thereby increasing the overall weight, size, and cost of the humeral component. Furthermore, because the surgeon is required to insert the stem of the humeral component into the humeral canal, the surgical procedure is somewhat complex, as the surgeon is first required to resect the proximal end of the humerus and subsequently ream the humeral canal prior to inserting the stem of the humeral component into the humeral canal. Increasing the complexity of the joint-replacement surgery increases the time in which the surgeon must spend in performing the procedure and therefore increases the overall cost of the procedure. Finally, requiring insertion of the stem into the humeral component results in additional bone removal, thereby increasing trauma and post-operative pain. It is further desirable to have a stemmed humeral implant that is adapted to follow the same surgical implant path as a stemless implant within the same product family.

What is needed in the art is a shoulder implant that improves upon prior art devices by providing design advantages that result in less bone loss, a simpler procedure, and greater initial and long-term implant fixation.

SUMMARY OF THE INVENTION

Aspects of the present invention provide shoulder prostheses with stemless humeral components and stemmed humeral components. The present invention also provides for methods for using the shoulder prostheses.

In one aspect, provided herein is an implant system that includes an anchor member, an articulating portion, and a coupling member with a first end and a second end. The articulating portion being coupled to the first end of the coupling member and the anchor member being coupled to the second end of the coupling member.

In another aspect, provided herein is an anchor member including a base, a circumferential groove, a central member and at least one support member. The base being positioned at a first end of the anchor member. The circumferential groove extending into the base from the first end of the anchor member. The central member positioned within the base and the circumferential groove. The at least one support member coupled to at least a portion of the central member at a first end and at least a portion of an interior surface of the base on a second end.

In yet another aspect, provided herein are surgical methods for inserting the implant systems.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which:

FIG. 23 is an exploded, side view of the implant system of FIG. 17, in accordance with an aspect of the present invention;

FIG. 24 is a side cross-sectional view of the implant system of FIG. 17 taken along line 24-24 in FIG. 18, in accordance with an aspect of the present invention;

FIG. 25 is a side view of a base for an embodiment of a stemless humeral implant, in accordance with an aspect of the present invention;

FIG. 26 is a side cross-sectional view of the base of FIG. 25 taken along line 26-26 in FIG. 30, in accordance with an aspect of the present invention;

FIG. 27 is a front view of the base of FIG. 25, in accordance with an aspect of the present invention;

FIG. 28 is a rear view of the base of FIG. 25, in accordance with an aspect of the present invention;

FIG. 47 is a medial view of the stemmed humeral implant of FIG. 45, in accordance with an aspect of the present invention;

FIG. 48 is a first side view of the stemmed humeral implant of FIG. 45, in accordance with an aspect of the present invention;

FIG. 59 is a second side view of the stemmed implant system of FIG. 45, in accordance with an aspect of the present invention;

FIG. 60 is a lateral view of the stemmed implant system of FIG. 45, in accordance with an aspect of the present invention;

FIG. 66 is an exploded side view of the stemmed implant system of FIG. 45, in accordance with an aspect of the present invention;

FIG. 67 is an exploded medial view of the stemmed implant system of FIG. 45, in accordance with an aspect of the present invention;

FIG. 79 is an exploded side view of the implant system of FIG. 68, in accordance with an aspect of the present invention;

FIG. 80 is an exploded medial view of the implant system of FIG. 68, in accordance with an aspect of the present invention;

DETAILED DESCRIPTION FOR CARRYING OUT THE INVENTION

Figure 1:
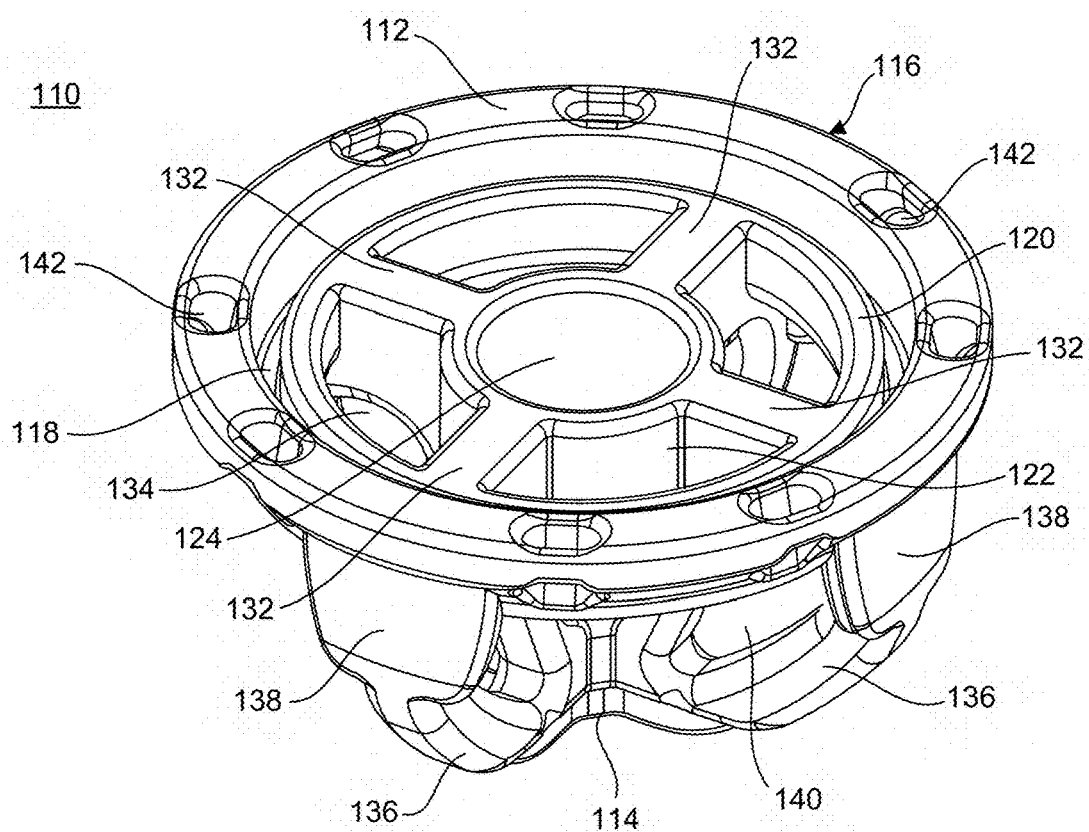
FIG. 1 is a first perspective view of an embodiment of a stemless humeral implant, in accordance with an aspect of the present invention.
Figure 2:
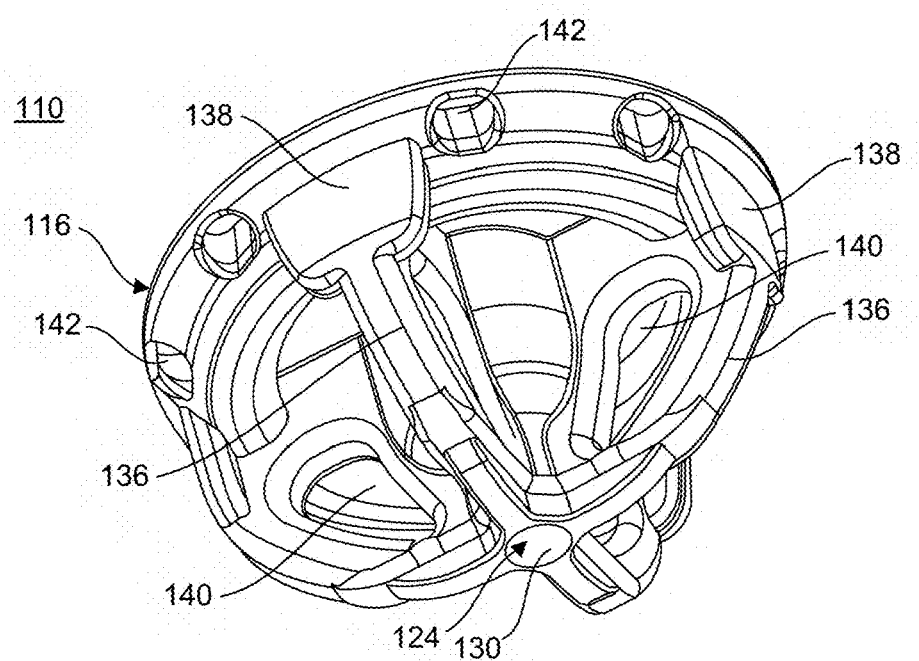
FIG. 2 is a second perspective view of the stemless humeral implant of FIG. 1, in accordance with an aspect of the present invention.
Figure 3:
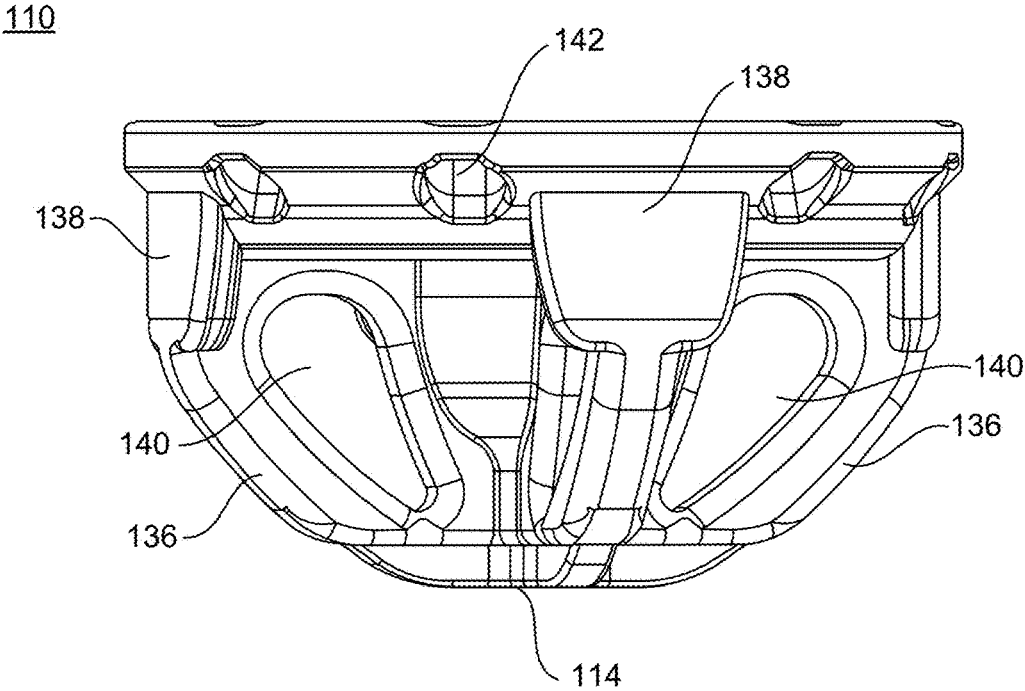
FIG. 3 is a first side view of the stemless humeral implant of FIG. 1, in accordance with an aspect of the present invention.
Figure 4:
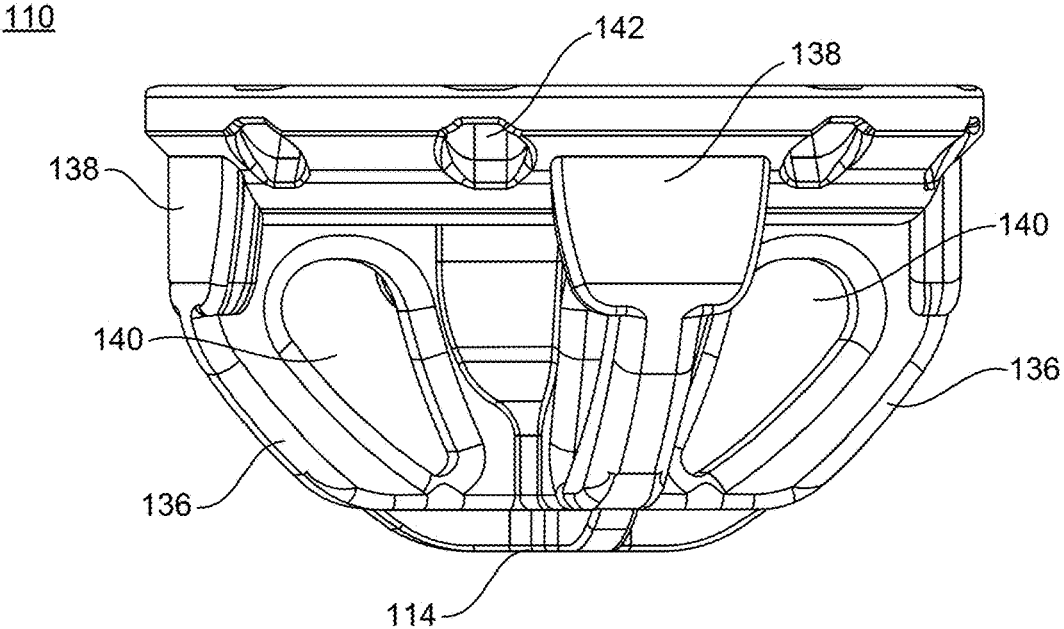
FIG. 4 is a second side view of the stemless humeral implant of FIG. 1, in accordance with an aspect of the present invention.

Generally stated, disclosed herein are shoulder prostheses with stemless humeral components and stemmed humeral components. Further, surgical methods for using the shoulder prostheses are discussed.

In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in the first figure of each embodiment.

Similarly, positions or directions may be used herein with reference to anatomical structures or surfaces. For example, as the current implants, devices, systems and methods are described herein with reference to use with the bones of the shoulder, the bones of the shoulder and upper arm may be used to describe the surfaces, positions, directions or orientations of the implants, devices, systems and methods. Further, the implants, devices, systems and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the implants, devices, systems and methods, and the aspects, components, features and the like thereof, described and/or illustrated herein may be changed, varied, modified, reconfigured or otherwise altered for use or association with another side of the body for a same or similar purpose without departing from the spirit and scope of the invention. For example, the implants, devices, systems and methods, and the aspects, components, features and the like thereof, described herein with respect to the right shoulder may be mirrored so that they likewise function with the left shoulder and vice versa. Further, the implants, devices, systems and methods, and the aspects, components, features and the like thereof, disclosed herein are described with respect to the shoulder for brevity purposes, but it should be understood that the implants, devices, systems and methods may be used with other bones of the body having similar structures, for example the lower extremity, and more specifically, with the bones of the ankle, foot, and leg.

Referring to the drawings, wherein like reference numerals are used to indicate like or analogous components throughout the several views, and with particular reference to FIGS. 1-8, there is illustrated a stemless humeral component or anchor 110 of a stemless implant system 100. The stemless implant system 100 includes a stemless humeral component or anchor 110, an articulating portion 150, and a coupling member 170. The humeral component 110 has a first end 112 and a second end 114. The first end 112 of the humeral component 110 has a first width and the second end of the humeral component 110 has a second width. The first width may be for example larger than the second width. The humeral component may include a base 116. The base 116 may include a recess or circumferential groove 118 extending into the base 116 from the first end 112 towards the second end 114. The groove 118 may be, for example, tapered as the groove 118 extends from a first end 112 into the base 116 of the anchor member 110, as shown in FIGS. 7, 8, 20 and 24. The recess 118 may form an interior lip 120 of the base 116. The base 116 may also be configured to mate out at the periphery when inserted into a patient.

With continued reference to FIGS. 1-16, the humeral component 110 may also include a central number 122 positioned within the base 116. The central member 122 may include a through hole 124 extending through the humeral component 110 from the first end 112 to the second end 114. The through hole 124 may include a first portion 126, a threaded portion 128, and a second portion 130. The first portion 126 may extend from the first end 112 toward the second end 114. The second portion 130 may extend from the second end 114 toward the first end 112. The threaded portion 128 may be positioned between the first portion 126 and the second portion 130. The first portion 126 may have, for example, a larger diameter than the second portion 130. The threaded portion 128 may have, for example, a diameter larger than the diameter of the second portion 130 and smaller than the diameter of the first portion 126.

Figure 5:
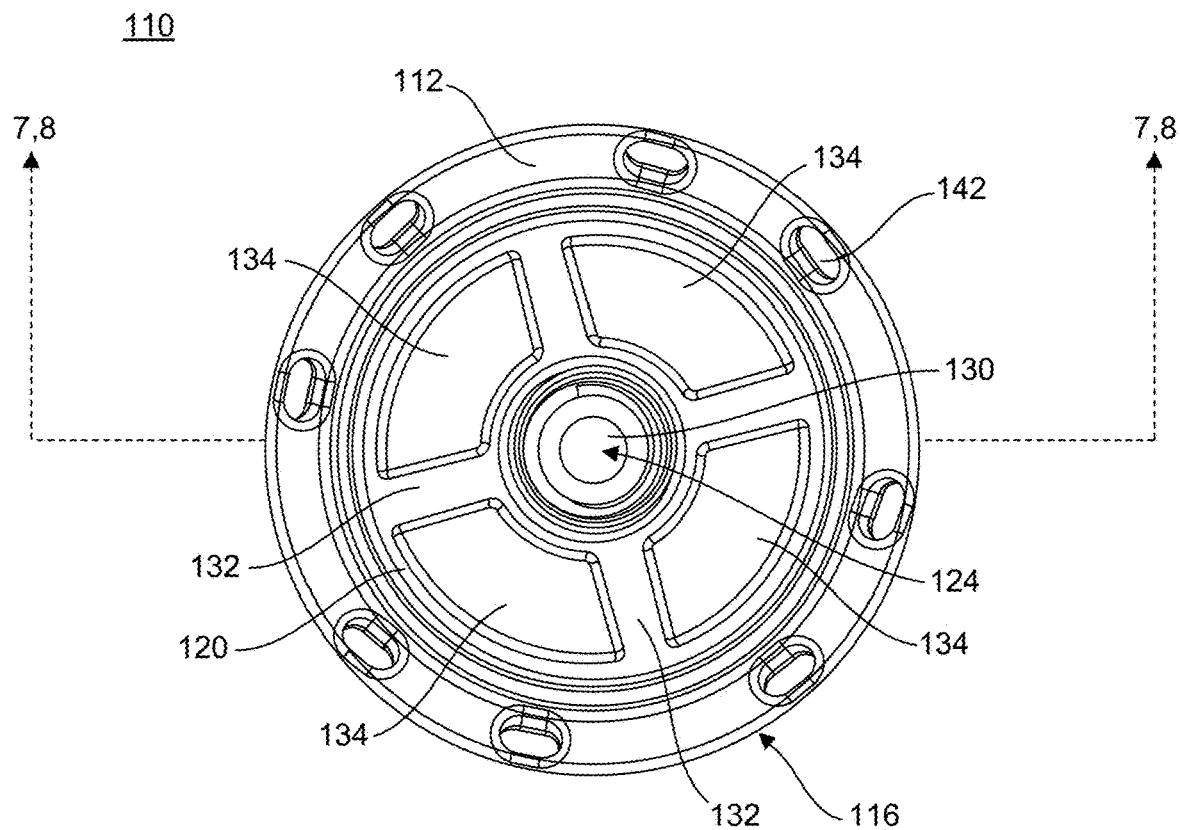
FIG. 5 is a top view of the stemless humeral implant of FIG. 1, in accordance with an aspect of the present invention.
Figure 6:
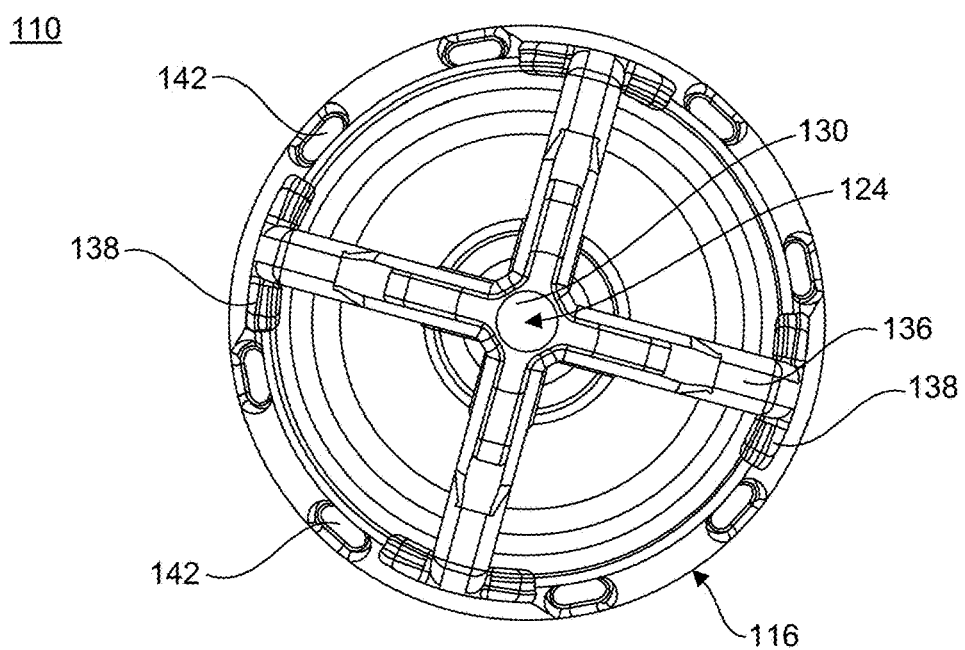
FIG. 6 is a bottom view of the stemless humeral implant of FIG. 1, in accordance with an aspect of the present invention.
Figure 7:
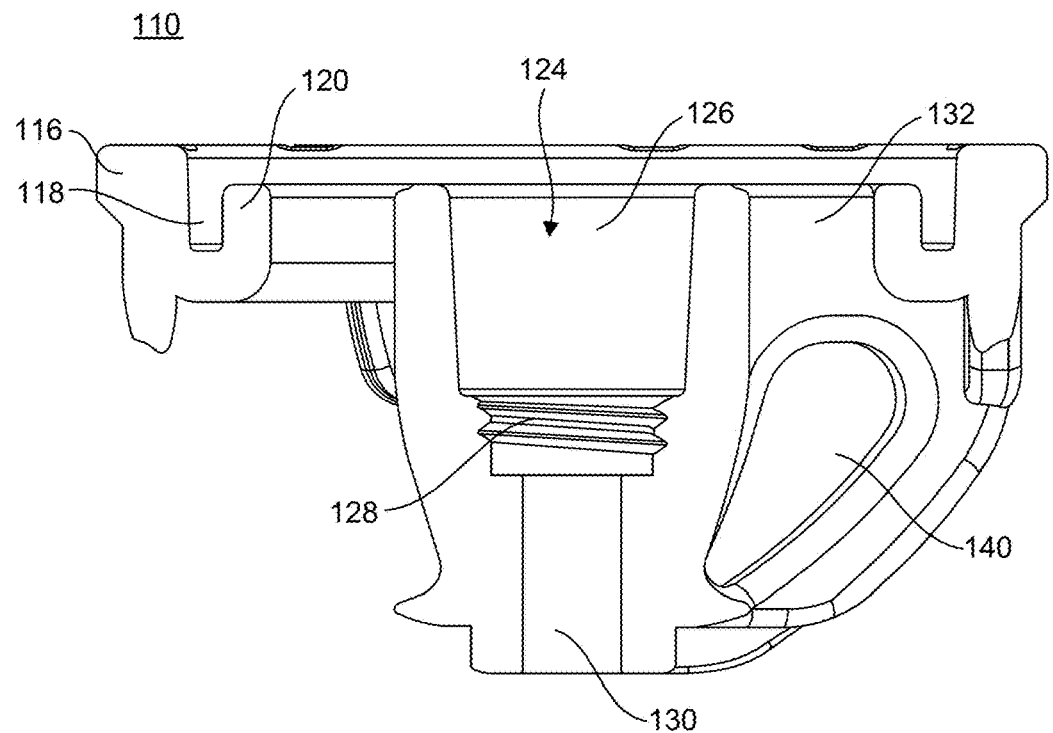
FIG. 7 is a side, cross-sectional view of the stemless humeral implant of FIG. 1 taken along line 7-7 in FIG. 5, in accordance with an aspect of the present invention.
Figure 8:
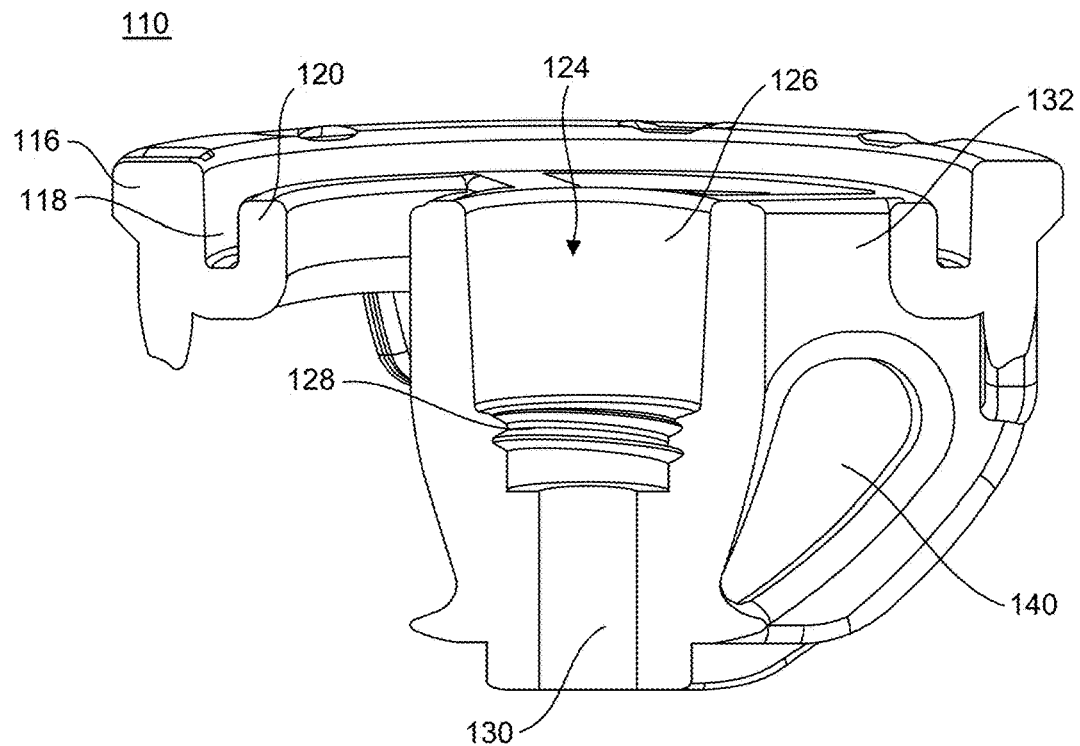
FIG. 8 is a perspective, cross-sectional view of the stemless humeral implant of FIG. 1 taken along line 8-8 in FIG. 5, in accordance with an aspect of the present invention.
Figure 9:
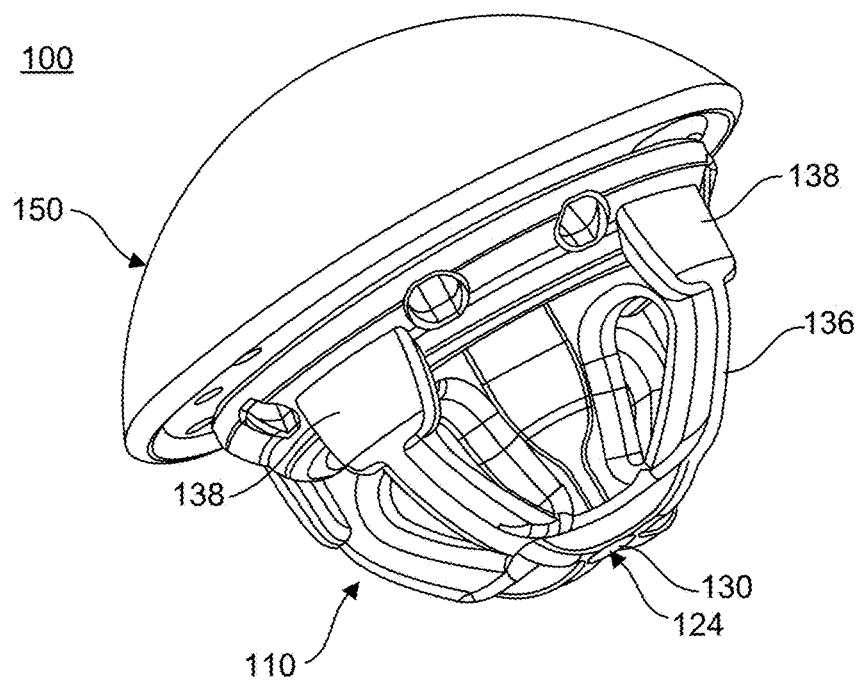
FIG. 9 is a first perspective view of an implant system including the stemless humeral implant of FIG. 1, in accordance with an aspect of the present invention.
Figure 10:
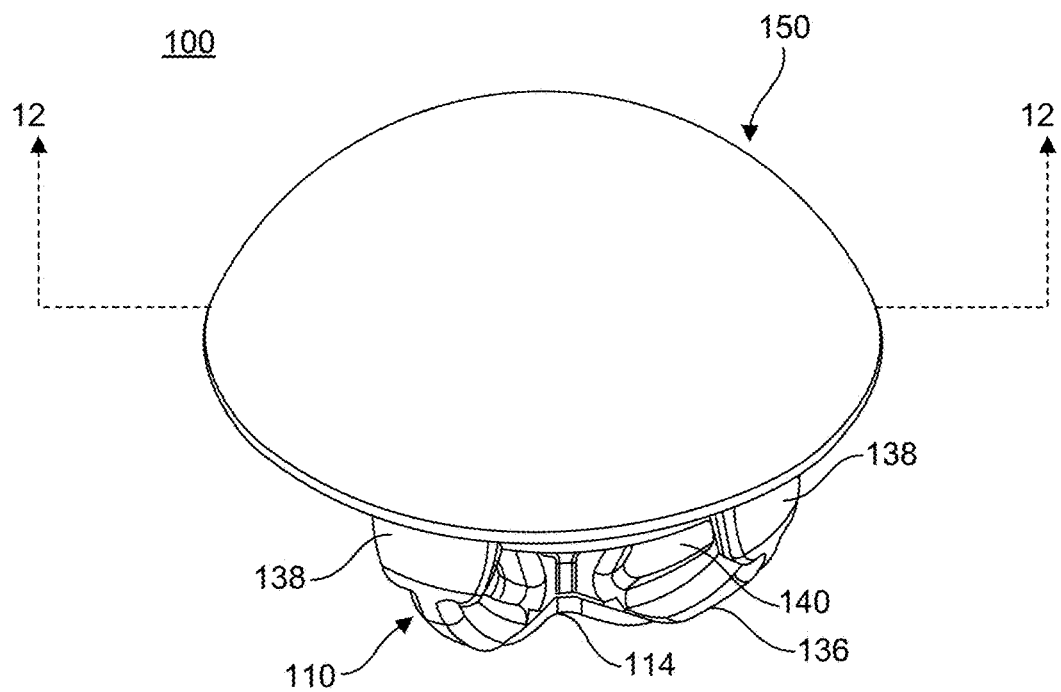
FIG. 10 is a second perspective view of the implant system of FIG. 9, in accordance with an aspect of the present invention.
Figure 11:
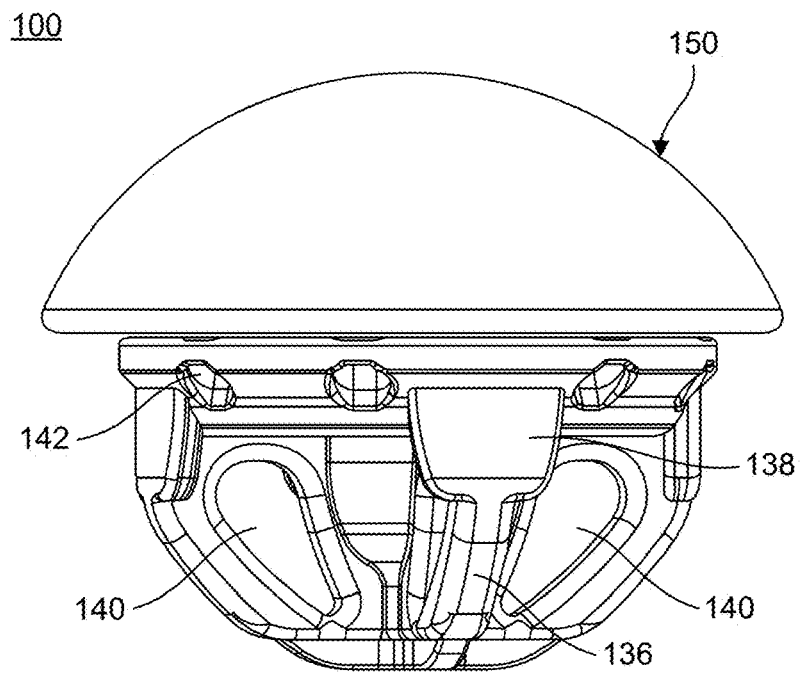
FIG. 11 is a side view of the implant system of FIG. 9 after removal of the guide pin, in accordance with an aspect of the present invention.
Figure 14:
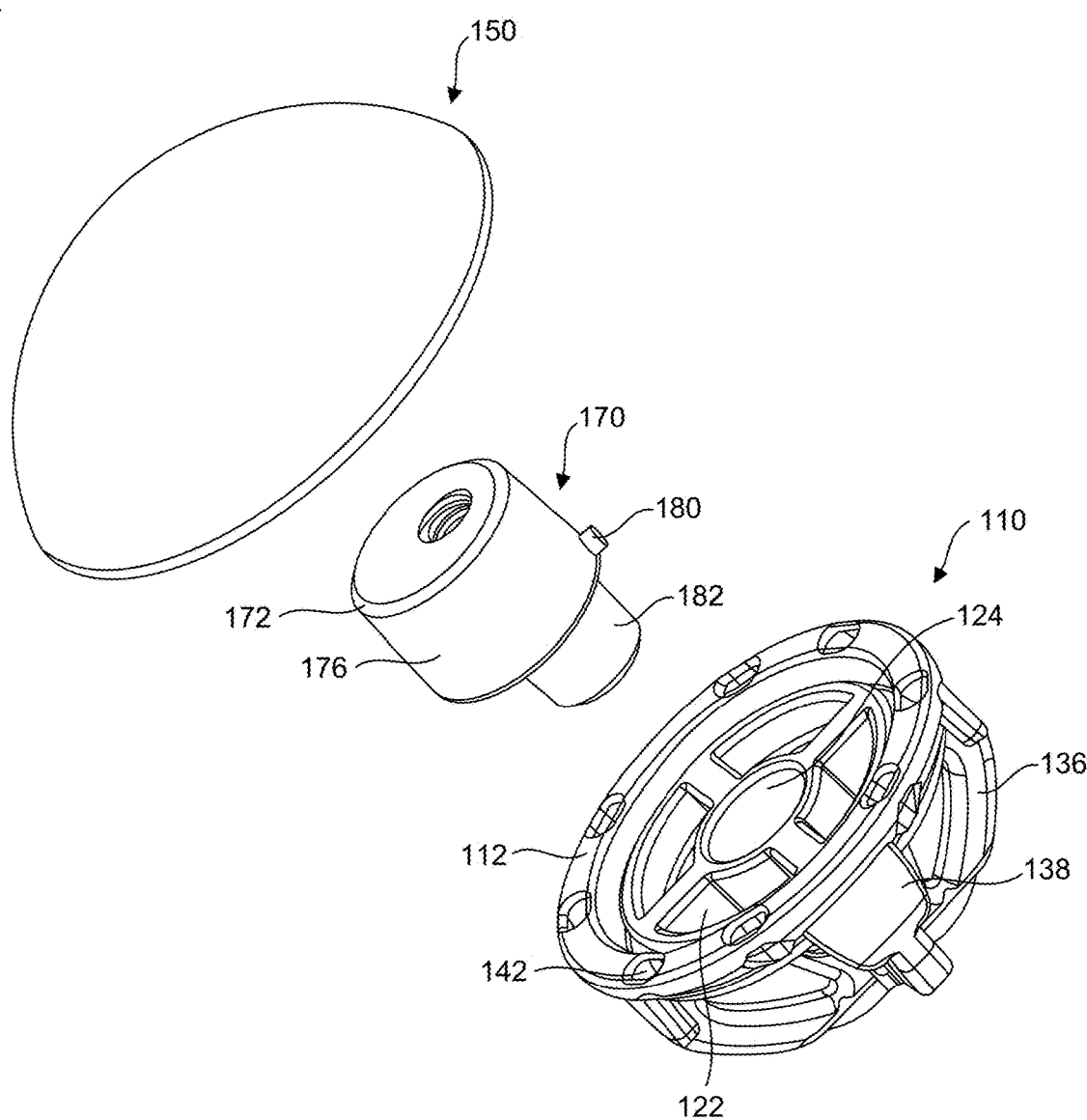
FIG. 14 is a second perspective, exploded view of the implant system of FIG. 9, in accordance with an aspect of the present invention.
Figure 16:
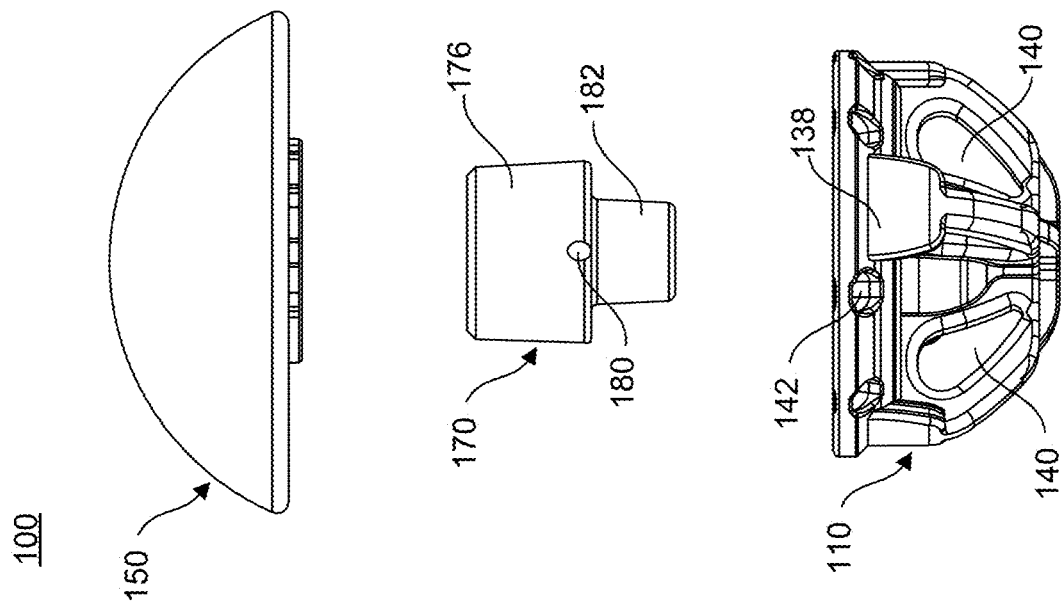
FIG. 16 is a second side, exploded view of the implant system of FIG. 9, in accordance with an aspect of the present invention.
Figure 15:
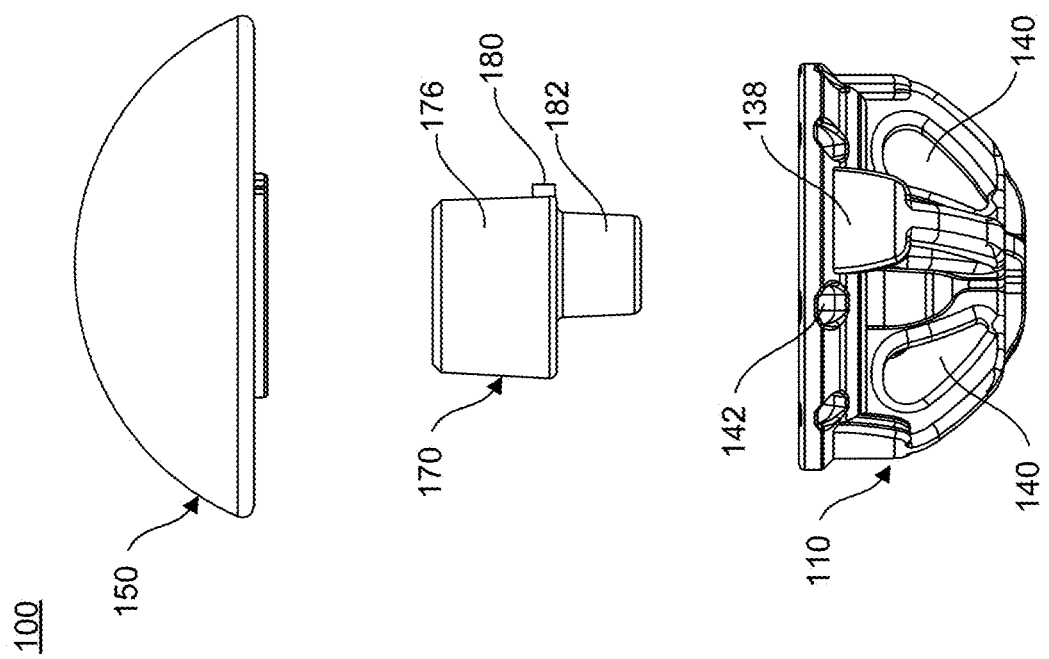
FIG. 15 is a first side, exploded view of implant system of FIG. 9, in accordance with an aspect of the present invention.
Figure 17:
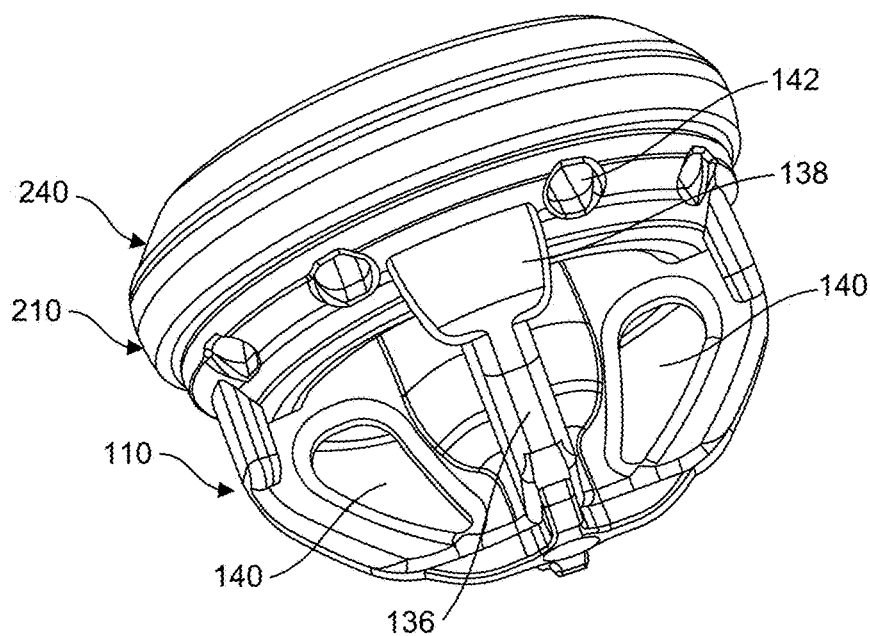
FIG. 17 is a first perspective view of another embodiment of an implant system, in accordance with an aspect of the present invention.
Figure 18:
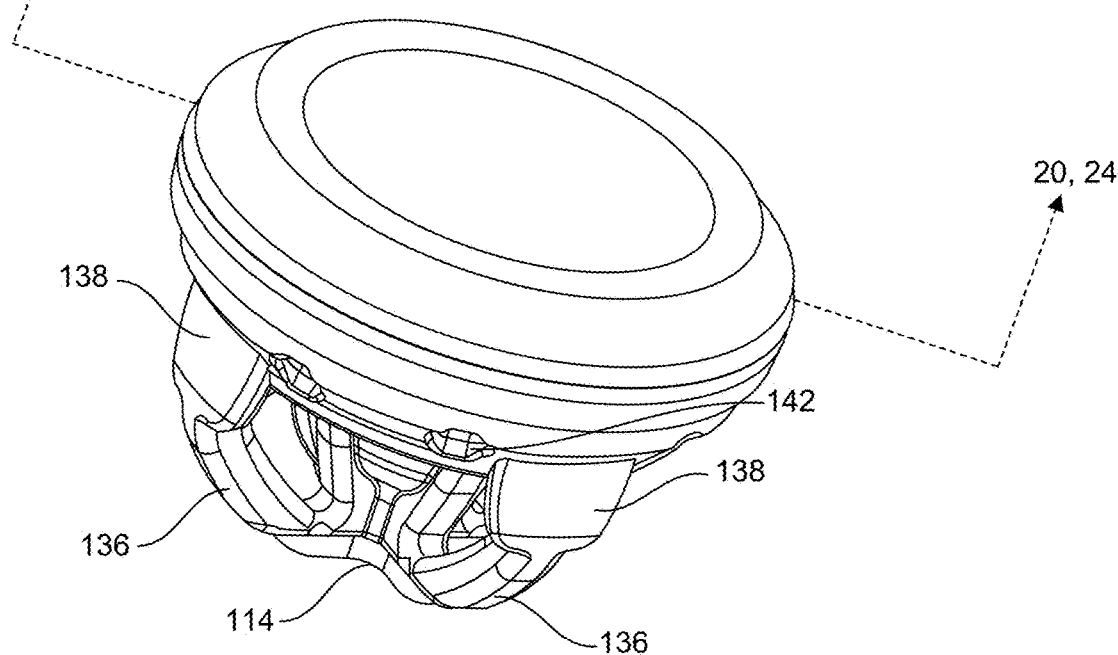
FIG. 18 is a second perspective view of the implant system of FIG. 17, in accordance with an aspect of the present invention.
Figure 19:
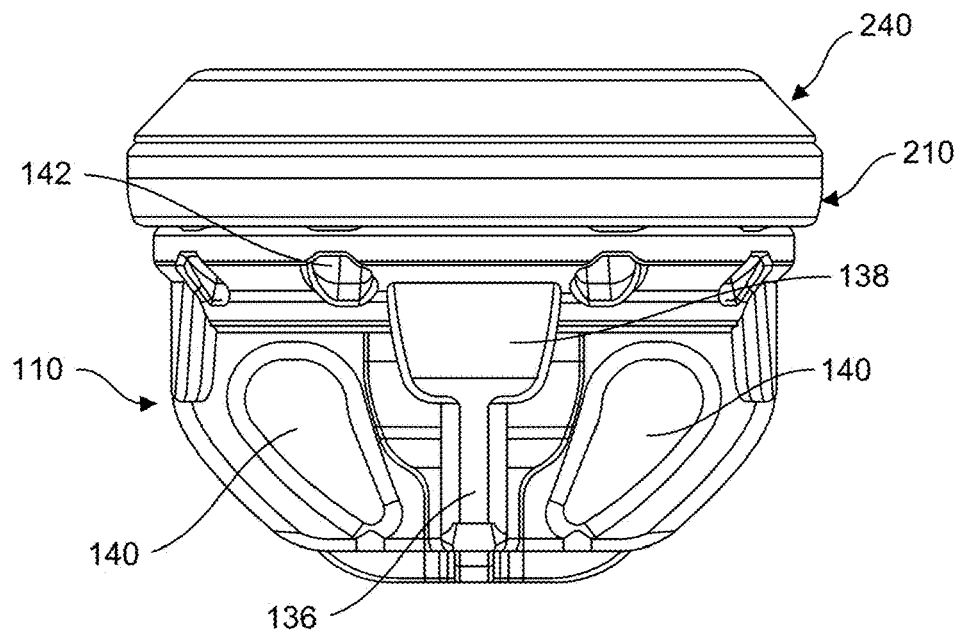
FIG. 19 is a side view of the implant system of FIG. 17, in accordance with an aspect of the present invention.

The humeral component 110 may also include arms or support members 132 extending between an exterior surface of the central number 122 and an interior surface of the lips 120 of the base 116, as shown in FIGS. 1-8 and 14. The base 116 of the humeral component 110 may also include windows or openings 134 extending through the base portion 116 from the first end 112 of the humeral component 110 toward the second end 114. The openings 134 may be, for example, positioned between each of the arms 132. As shown in FIGS. 1, 5, and 14, the humeral component 110 may include, for example, four arms. The base 116 may also include a plurality of fastener openings 142 extending through the base 116 from the first end 112 toward the second end 114. The plurality of openings 142 may be positioned between an exterior surface of the base 116 and the recess 118. The plurality of fastener openings 142 may be, for example, configured or sized and shaped to receive fasteners, such as, sutures and the like.

In addition, the humeral component 110 may include legs or extension members 136 extending away from a bottom surface of the base 116 toward the second end 114 of the humeral component 110. A first end of each leg 136 is coupled to the base 116 and the second end of each leg 136 is coupled to the exterior surface of the central member 122 at a distal end. The legs 136 may be, for example, curved or arced as they extend from a bottom surface of the base 116 to the second end 114 of the humeral component 110. Each leg 136 may be coupled to the base 116 and an arm 132 by a base member 138. The base members 138 may each have a width larger than the width of the coupled leg 136. The legs 136 may be, for example, equally spaced apart from each other circumferentially around the base 116 of the humeral component 110. A cutout 140 may extend through each leg 136 below or distal to a corresponding arm 132. The cutouts 140 may be, for example, position perpendicular to the openings 134.

Figure 12:
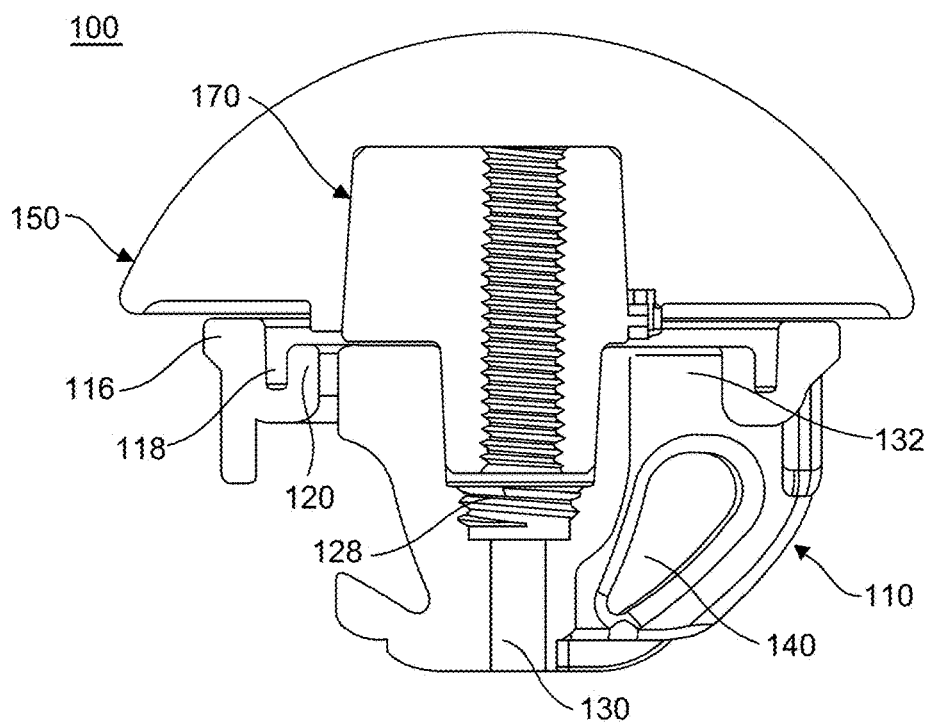
FIG. 12 is a cross-sectional view of the implant system of FIG. 9 taken along line 12-12 in FIG. 10, in accordance with an aspect of the present invention.
Figure 13:
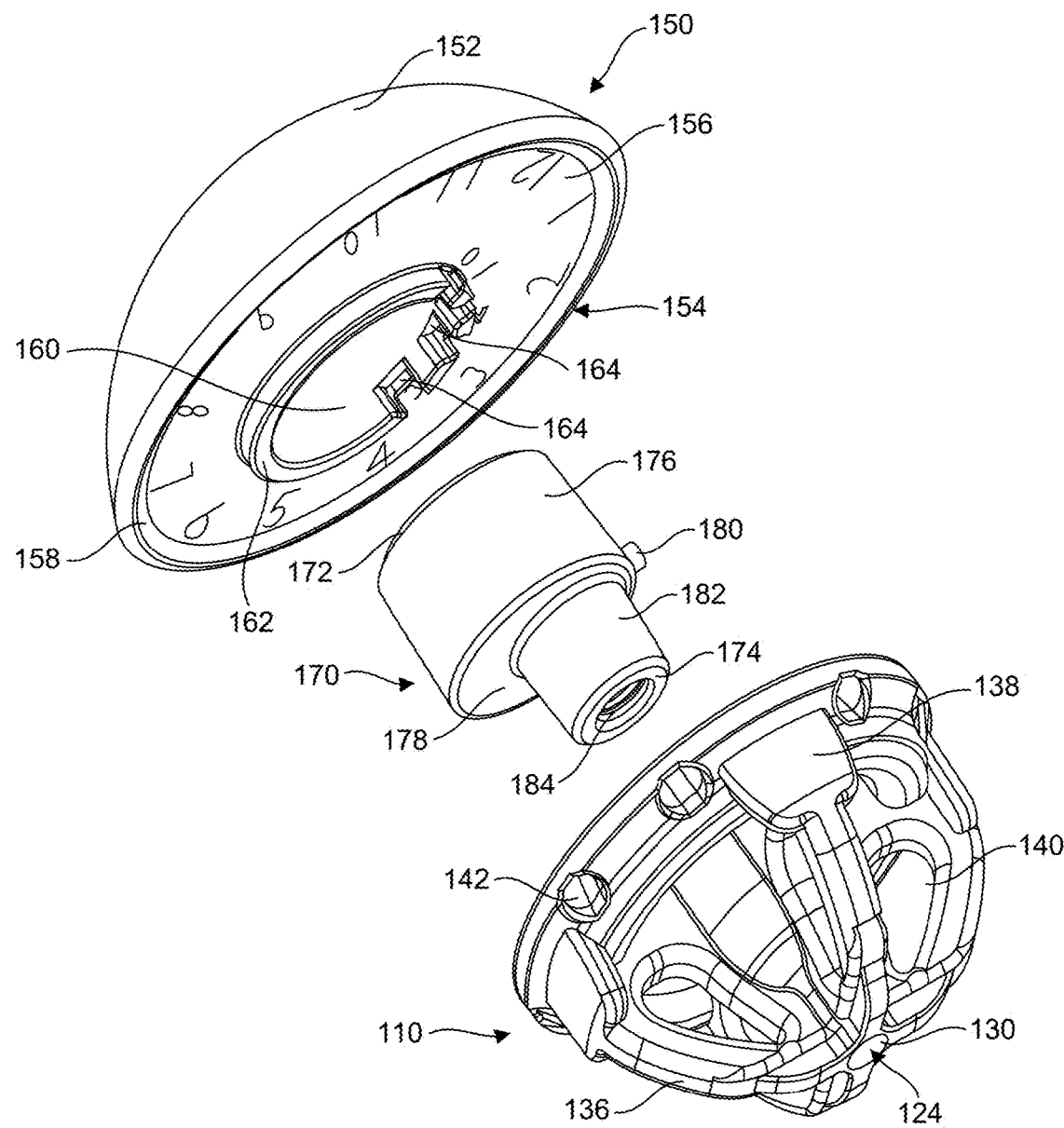
FIG. 13 is a first perspective, exploded view of the implant system of FIG. 9, in accordance with an aspect of the present invention.

Referring now to FIGS. 9-16, the orthopedic implant assembly or stemless implant system 100 is shown. As shown in FIGS. 12-16, the articulating portion 150 includes an articulating surface 152 and a coupling surface or bottom surface 154 positioned opposite the articulating surface 152. The articulating surface 152 is a convex articulating surface. The coupling surface 154 may include, for example, a recessed region 156 extending into the bottom surface 154 toward the articulating surface 152. The inset recessed region 156 forms an outer edge 158 surrounding the recessed region 156. The recessed region 156 may be, for example, sized and shaped to receive the base 116 of the stemless humeral component 110. The articulating portion 150 may also include an opening 160 extending into the articulating portion 150 from the bottom surface 154. A lip 162 may surround the opening 160, as shown in FIG. 13. The lip 162 may include at least one slot or anti-rotation slot 164 inset into the lip 162. The at least one slot 164 may be, for example, four slots 164.

With continued reference to FIGS. 9-16, the coupling member 170 may include a first end 132 and a second end 174 positioned opposite the first end 132. Coupling member 170 may include a first portion or base member 176 coupled to a second portion or extension number 182. The second portion 182 extends away from a bottom surface 178 of the base member 176. The first portion 176 may have a first diameter larger than a second diameter of the second portion 182. The coupling member 170 may also include, for example, an anti-rotation protrusion or protrusion 180 extending away from an exterior surface of the base member 176. The coupling member 170 may also include a through hole or threaded opening 184 extending through the coupling member 170 from the first end 172 to the second end 174.

Referring now to FIG. 12, a cross-section of an assembled stemless implant system 100 is shown. The first end 172 of the coupling member 170 is inserted into the opening 160 of the articulating portion 150. The alignment protrusion 180 may be, for example, aligned with at least one slot 164 and inserted into a slot 164 of the at least one slot 164 to prevent rotation of the articulating portion 150 with respect to the coupling member 170. The coupling member 170 may be coupled to the articulating portion 150, for example, with a fastener (not shown), a friction fit, such as, a taper fit, and alternative known methods for coupling articulating portion 152 and anchor 110. The base 116 of the humeral component 110 may be, for example, received within the recessed region 156 of the articulating portion 150, as shown is FIG. 12.

Referring now to FIGS. 17-24 and with continued reference to FIGS. 1-8, a reverse orthopedic implant assembly or a reverse stemless implant system 200 is shown. The reverse implant system 200 may have a first end 202 at a second end 204. The reverse implant system 200 may include, for example, a stemless humeral component or anchor 110, a spacer or coupling member 210, and a socket number 240. The humeral component 110 is as described with reference to FIGS. 1-8 and will not be described again here for brevity's sake.

Figure 20:
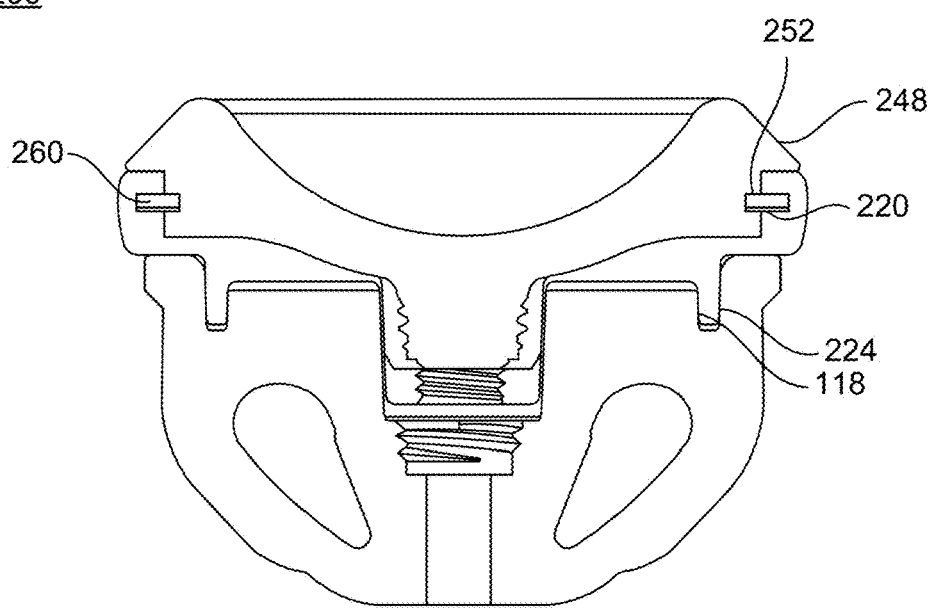
FIG. 20 is a cross-sectional view of the implant system of FIG. 17 taken along line 20-20 in FIG. 18, in accordance with an aspect of the present invention.
Figure 21:
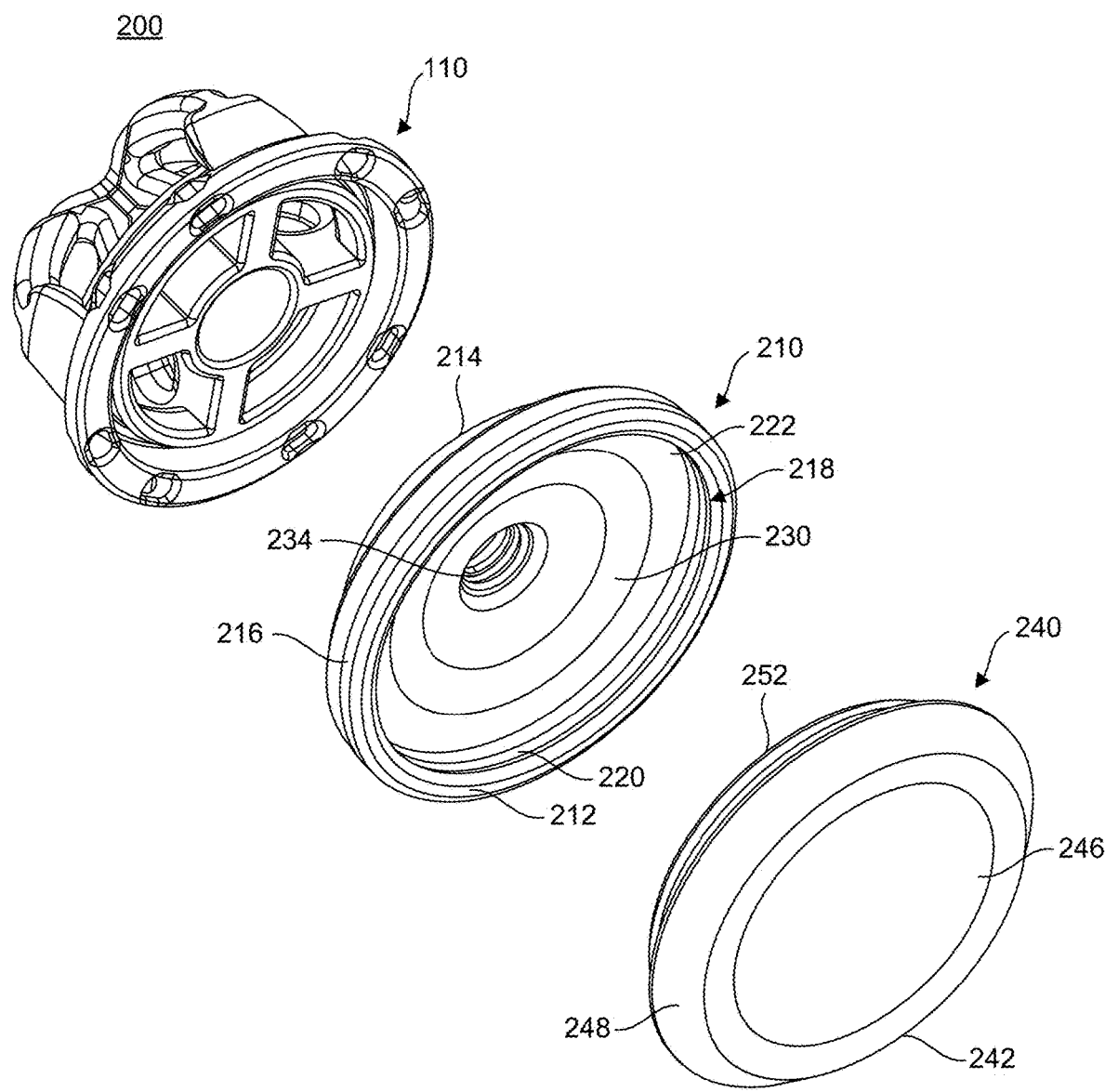
FIG. 21 is an exploded, first perspective view of the implant system of FIG. 17, in accordance with an aspect of the present invention.
Figure 22:
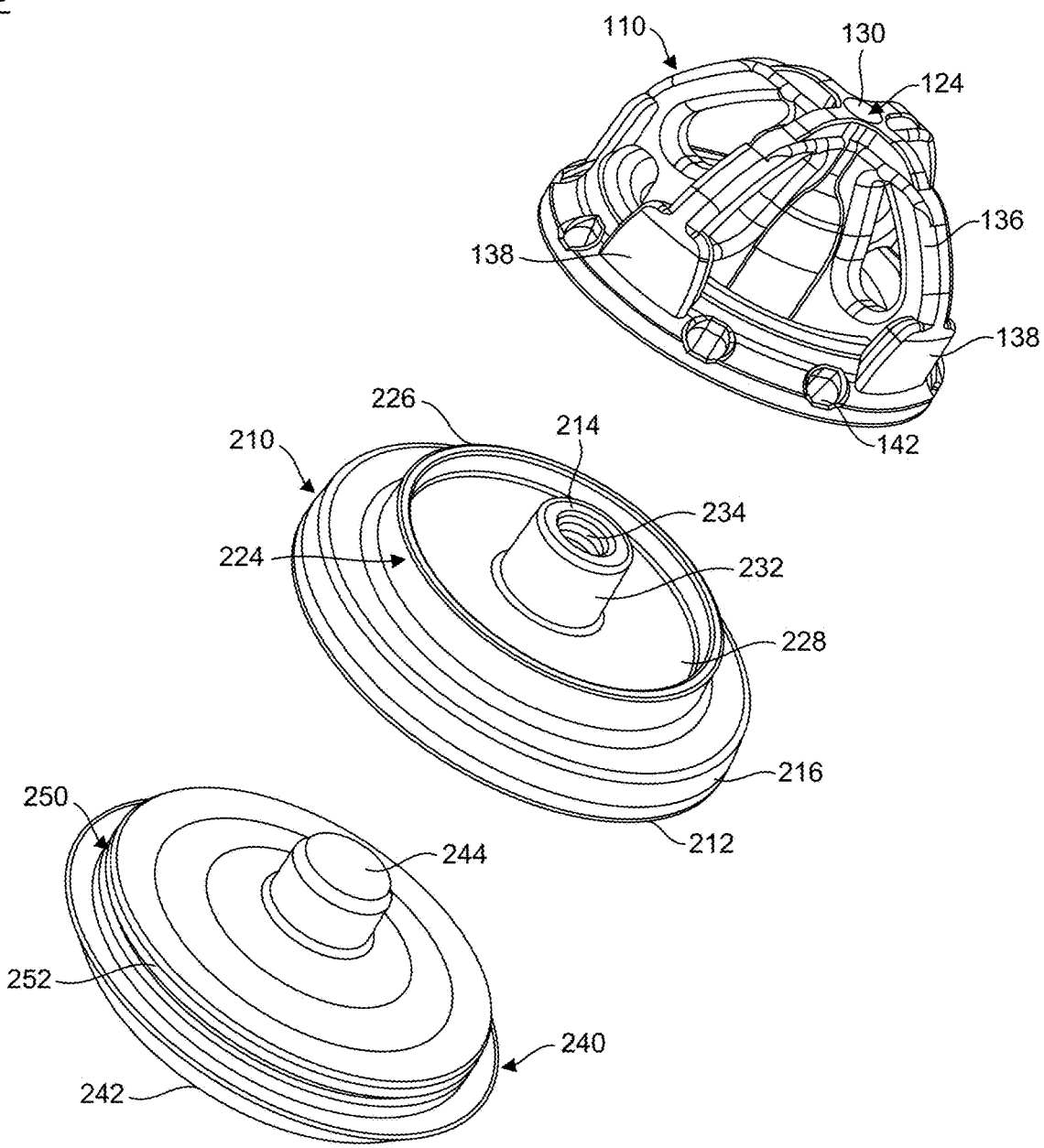
FIG. 22 is exploded, second perspective view of the implant system of FIG. 17, in accordance with an aspect of the present invention.
Figure 30:
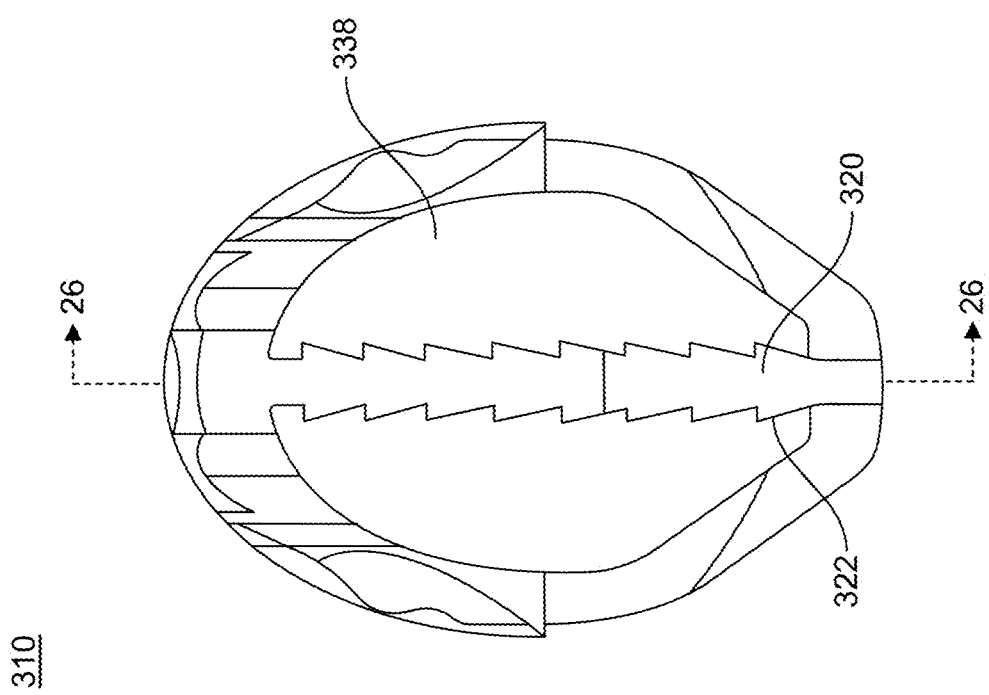
FIG. 30 is a top isometric view of the base of FIG. 25, in accordance with an aspect of the present invention.
Figure 29:
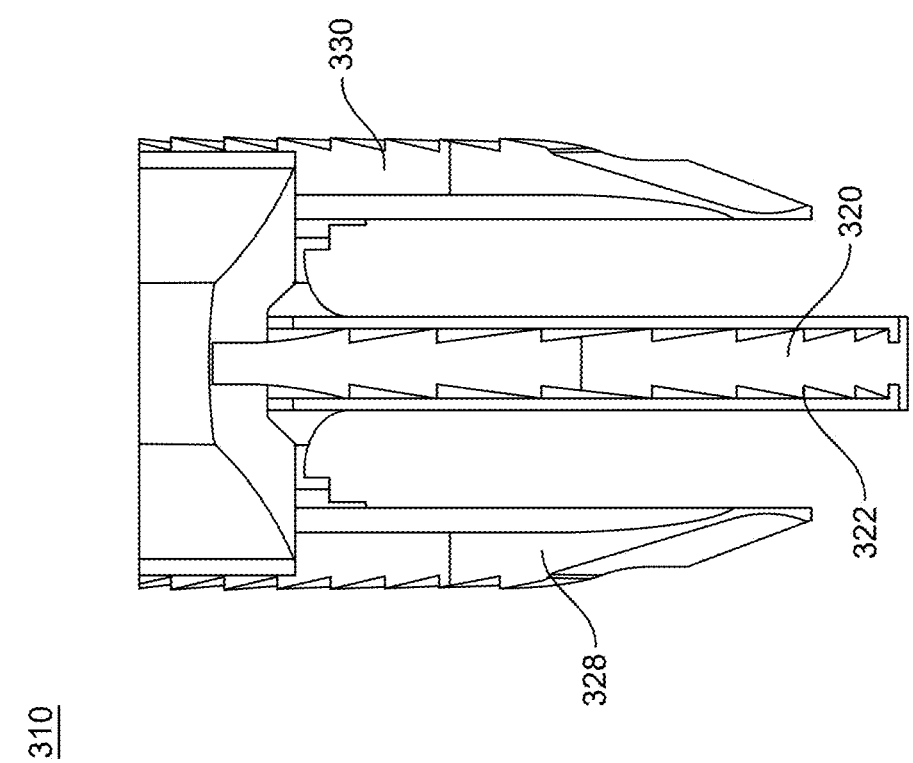
FIG. 29 is a front isometric view of the base of FIG. 25, in accordance with an aspect of the present invention.
Figure 31:
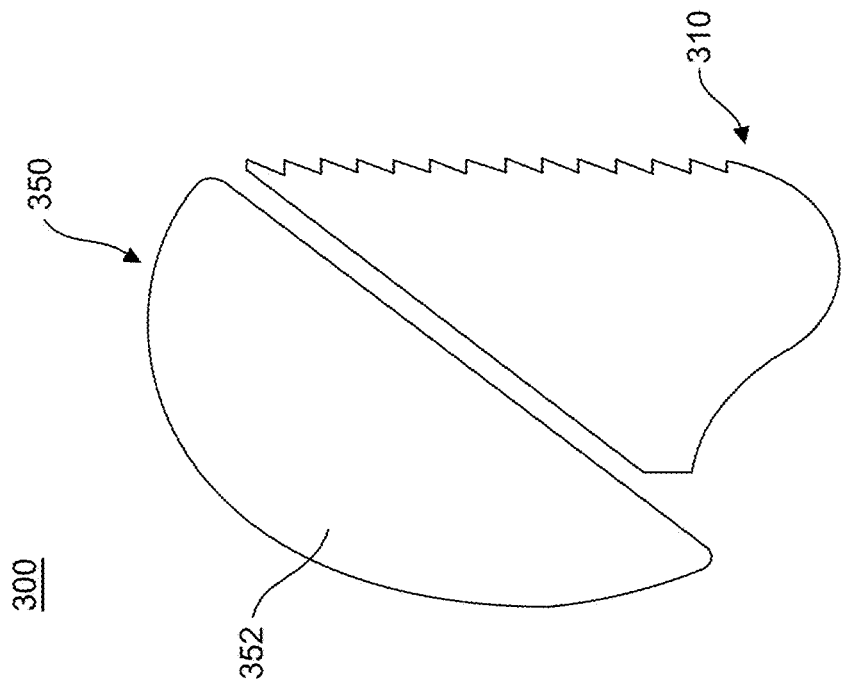
FIG. 31 is a side view of a stemless shoulder implant assembly including the base of FIG. 25, in accordance with an aspect of the present invention.
Figure 32:
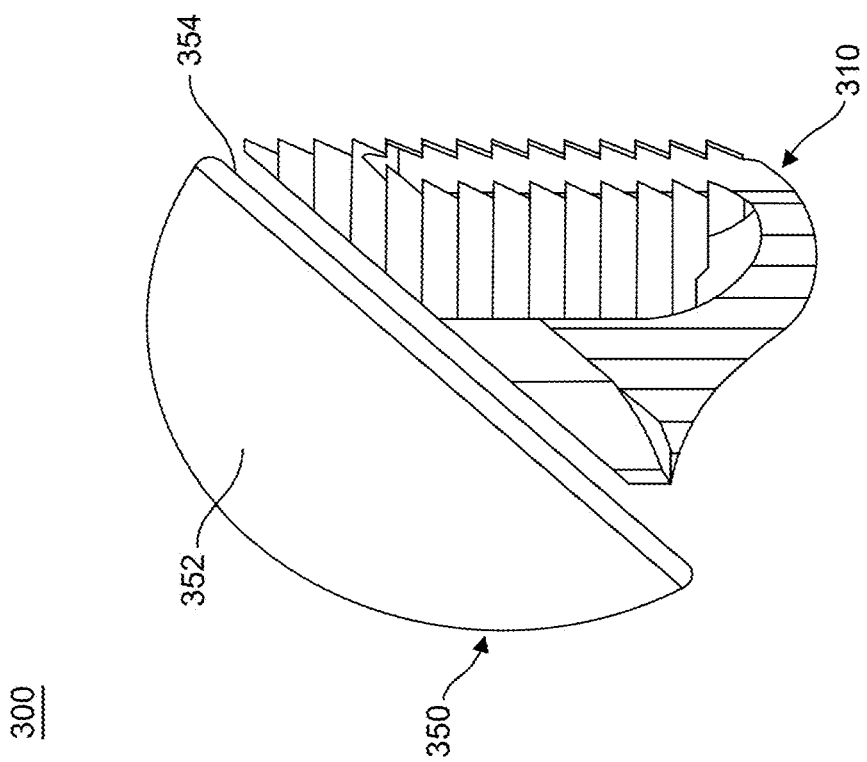
FIG. 32 is a side cross-sectional view of the stemless shoulder implant assembly of FIG. 31, in accordance with an aspect of the present invention.
Figure 34:
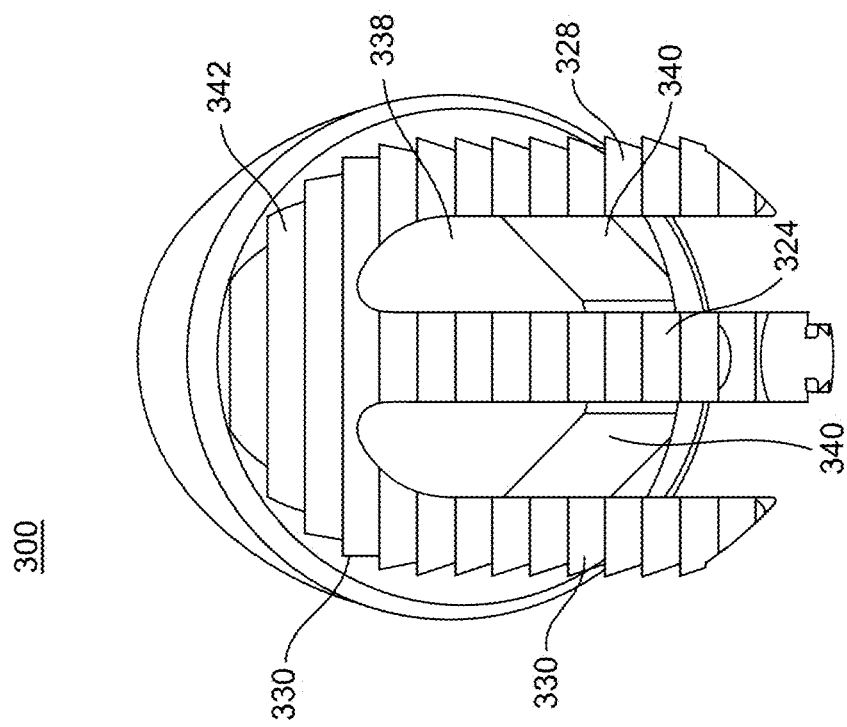
FIG. 34 is a rear view of the stemless shoulder implant assembly of FIG. 31, in accordance with an aspect of the present invention.
Figure 33:
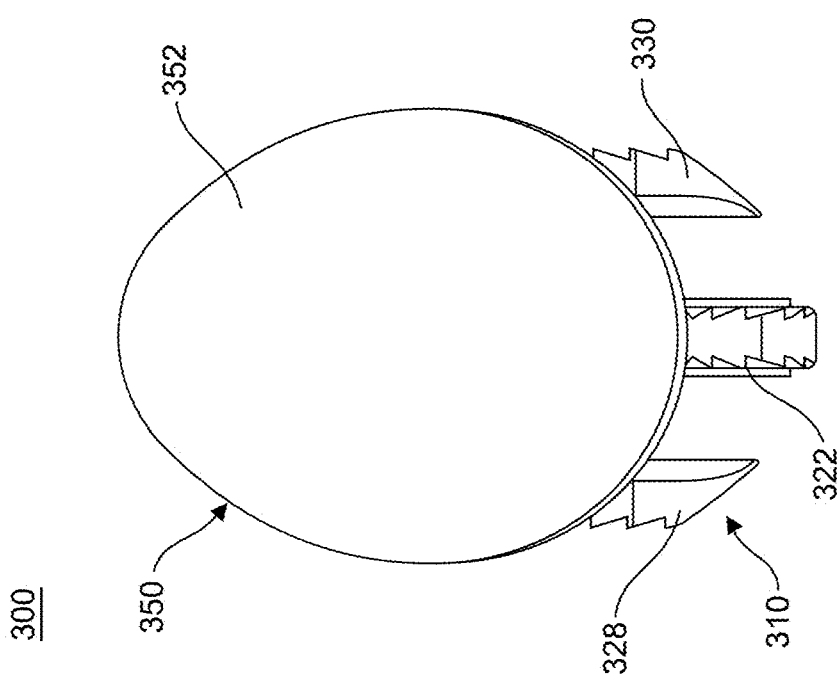
FIG. 33 is a front view of the stemless shoulder implant assembly of FIG. 31, in accordance with an aspect of the present invention.
Figure 36:
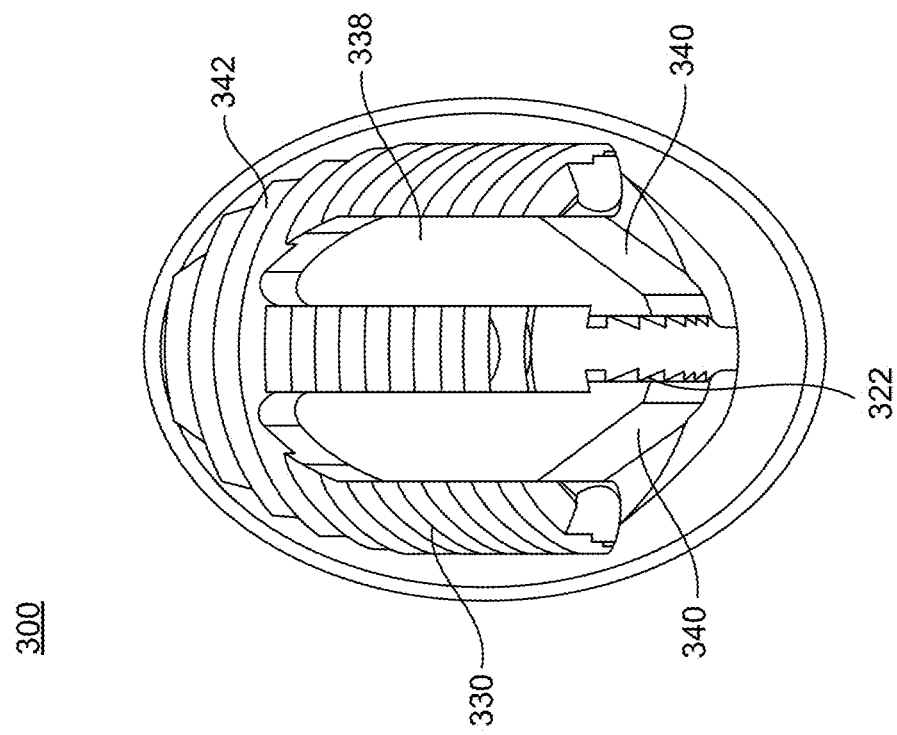
FIG. 36 is a bottom view of the stemless shoulder implant assembly of FIG. 31, in accordance with an aspect of the present invention.
Figure 35:
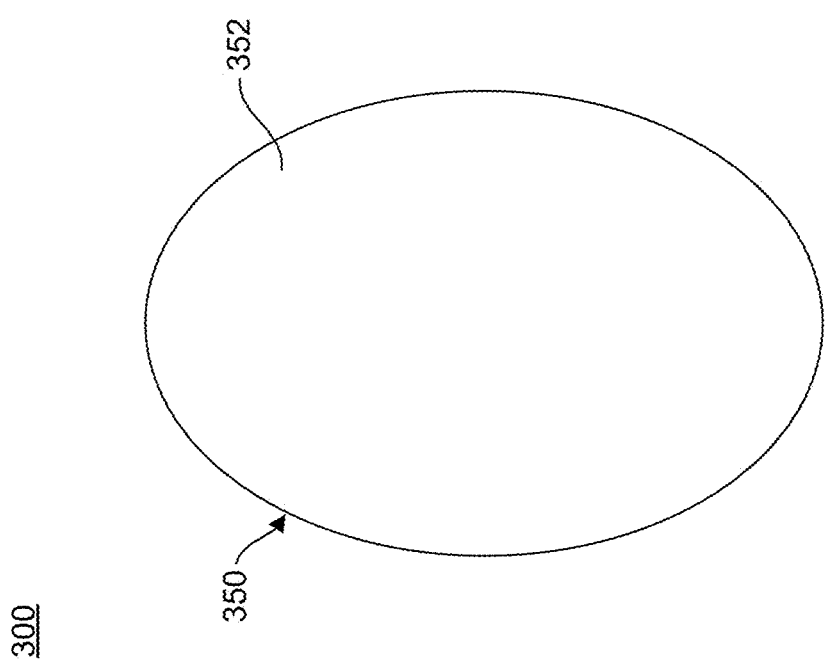
FIG. 35 is a top view of the stemless shoulder implant assembly of FIG. 31, in accordance with an aspect of the present invention.
Figure 38:
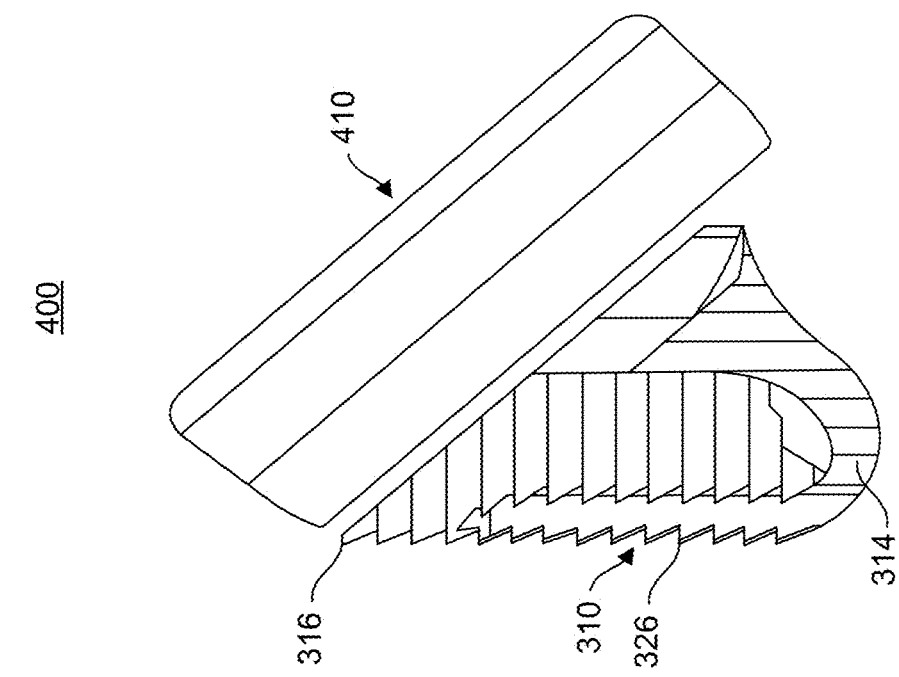
FIG. 38 is a side view of an embodiment of a reverse stemless shoulder implant assembly, in accordance with an aspect of the present invention.

As shown in FIGS. 20-24, the coupling member 210 includes a first end or upper surface 212 and a second end or lower surface 214. The coupling member 210 includes a base member 216, an extension number 224, and a protrusion or extension number 232. The extension member 224 extends away from a bottom surface of the base number 216 and the protrusion 232 extends away from the extension number 224. The base member 216 includes a recessed region 218 inset into the coupling member 210 from the first end 212 and forming an interior side wall surrounding the recessed region 218. The interior side wall may include, for example, a circumferential groove 220 extending from the recessed region 218 toward an exterior surface of the base member 216. The circumferential groove 220 may receive, for example, a coupling element 260, such as, an O-ring, as shown in FIG. 20. At least a portion of the recessed region 218 may be, for example, a flat surface 222 as best seen in FIGS. 20 and 24. The flat surface 222 may extend from the interior side wall toward a center of the base member 216.

Referring now to FIGS. 20 and 22-24, the extension number 224 includes a rim 226 extending away from a bottom surface of the base member 216. The rim 226 surrounds a bottom surface 228 of the extension member 224. The bottom surface 228 may be, for example, a flat surface for receiving the first end 112 of the humeral component 110. The top surface 230 of the extension member 224 may coupled to and extend from the flat surface 222 of the base number 216. The top surface 230 may be, for example, arced or curved as shown in FIGS. 20 and 24. The extension member 224 may also be, for example, tapered as the extension member 224 extends away from the bottom surface of the base member 216, as shown in FIGS. 20 and 24. The extension member 224 may be used, for example, to secure the spacer 210 to the anchor member 110 in the reverse implant system 200.

The protrusion or extension member 232 extends away from the bottom surface 228 to the second end 214, as shown in FIGS. 20 and 22-24. The protrusion 232 may include a through hole or threaded opening 234 extending through the protrusion 232 from the second end 214 to the top surface 230, as best seen in FIG. 24.

With continued reference to FIGS. 20-24, the socket member 240 includes a first end or upper surface 242 and a second end or lower surface 244. The first end 242 includes an articulating surface 246 recessed into the socket member 240. The first end 242 also includes a tapered edge 248 extending circumferentially around the socket member 240, as shown in FIGS. 19, 20, 23 and 24. The socket member 240 also includes an engagement protrusion 250 extending away from the tapered edge 248. The engagement protrusion 250 may be, for example, inset from the outermost portion of the tapered edge 248. The engagement protrusion 250 may include a circumferential groove 252. The circumferential groove 252 of the socket member 240 may align with the circumferential groove 220 of the coupling member 210 when the socket member 240 is inserted into the coupling member 210. The circumferential groove 252 of the socket member 240 may be configured to receive a coupling member 260, such as, an O-ring. The socket member 240 may also include a bottom surface 254. The bottom surface 254 may include a flat portion and an arced or curved portion 256. The socket member 240 may also include a protrusion or stem 258 extending away from the bottom surface 254. The curved portion 256 may extend between the flat portion of the bottom surface 254 and the protrusion 258. The protrusion 258 may be, for example, configured or sized and shaped to engage the through hole 234 of the coupling member 210.

As shown in FIGS. 17-20, the implant system 200 may be assembled by inserting the protrusion 232 of the coupling member 210 into the through hole 124 of the humeral component 110 and the extension number 224 of the coupling member 210 into the interior of the base 116. In addition, the protrusion 258 of the socket member 240 may be inserted into the through hole 234 of the coupling member 210 and the engagement protrusion 250 may engage the recessed region 218 of the coupling member 210. An O-ring 260 or like coupling member may be positioned within the circumferential groove 220 of the coupling member 210 and the 42 circumferential groove 252 of the socket member 242 secure the socket member 242 the coupling member 210. Finally, a fastener (not shown) may be inserted into the through hole 124 of the humeral component 110 and engage the threaded opening 234 of the coupling member 210 to secure the humeral component 110 to the coupling member 210.

Figure 37:
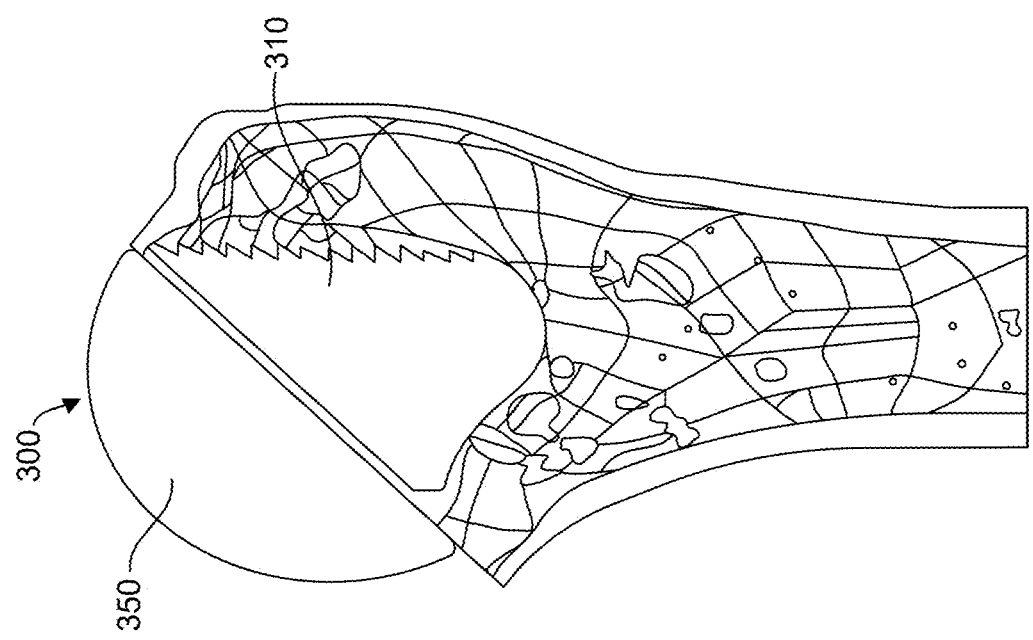
FIG. 37 is a side, cross-sectional view of the stemless shoulder implant assembly of FIG. 31 implanted in a bone, in accordance with an aspect of the present invention.
Figure 40:
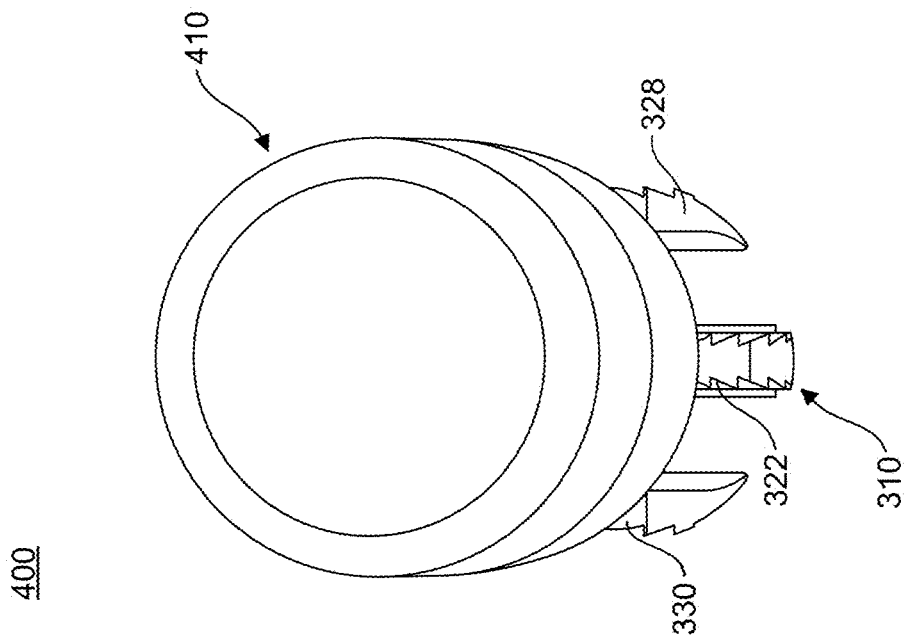
FIG. 40 is a front view of the reverse stemless shoulder implant assembly of FIG. 38, in accordance with an aspect of the present invention.
Figure 39:
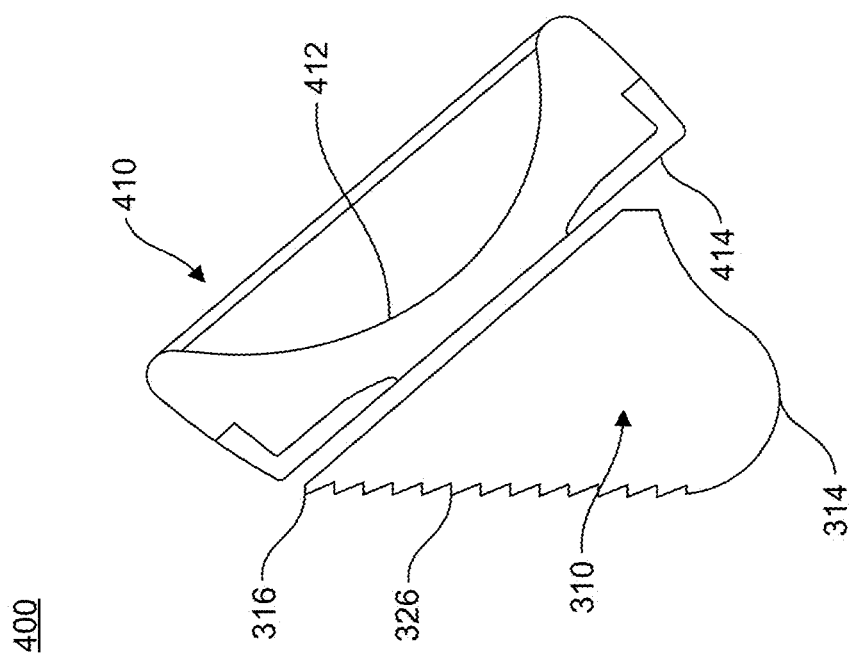
FIG. 39 is a side cross-sectional view of the reverse stemless shoulder implant assembly of FIG. 38, in accordance with an aspect of the present invention.
Figure 42:
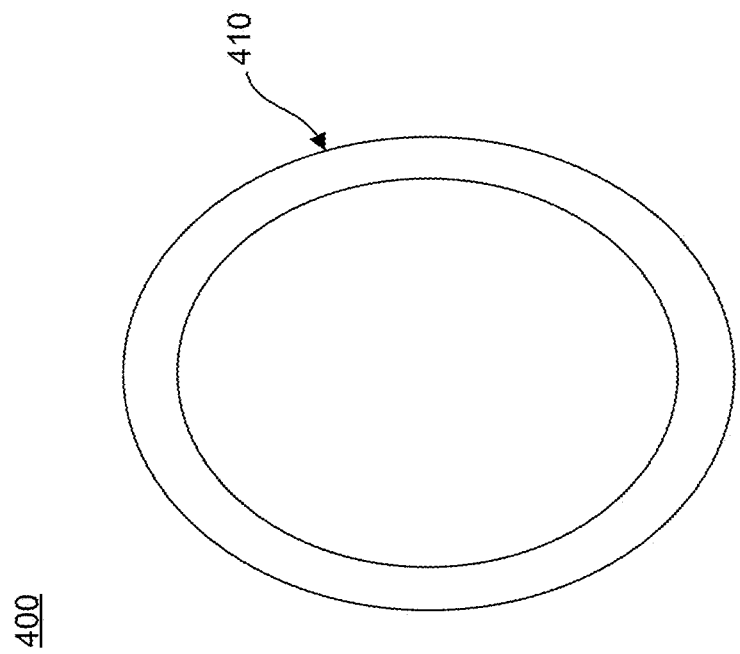
FIG. 42 is a top view of the reverse stemless shoulder implant assembly of FIG. 38, in accordance with an aspect of the present invention.
Figure 41:
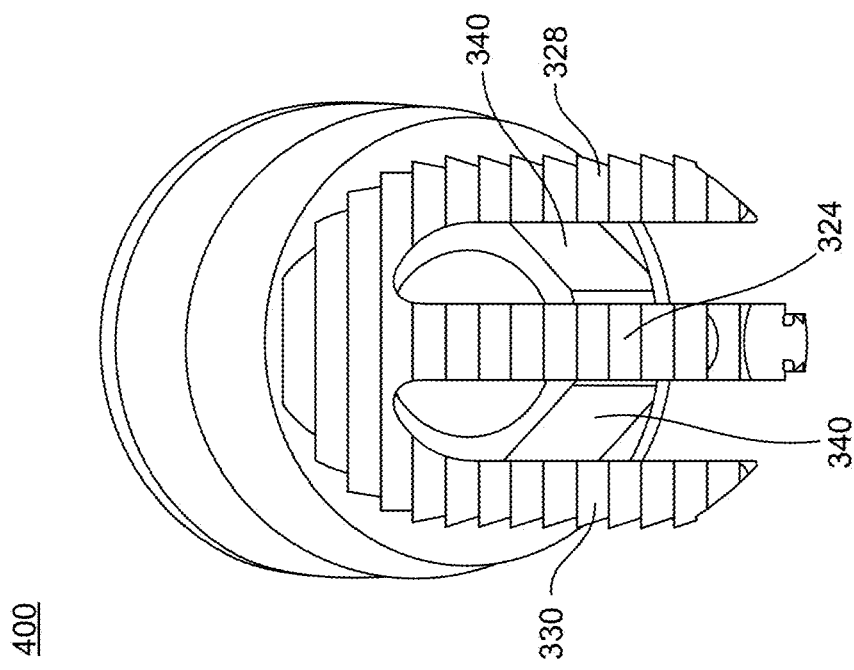
FIG. 41 is a rear view of the reverse stemless shoulder implant assembly of FIG. 38, in accordance with an aspect of the present invention.

Referring first collectively to FIGS. 25-37, another orthopedic implant assembly or stemless implant system 300 is shown. FIGS. 25-30 show multiple views of an anchor or humeral component 310 for use in the orthopedic implant assembly 300. The anchor 310 is adapted to be inserted into a humeral bone, as shown in FIG. 37. The anchor 300 generally includes a base 312, a first or central keel 320, a second or rear keel 324, a third or medial keel 328, and a fourth or lateral keel 332. The base 312 may be disposed at a constant angle, for example, ranging from 125 degrees to 155 degrees and more preferably about 135 degrees, relative to each keel 320, 324, 328, 332. Each keel 320, 324, 328, 332 may be, for example, co-planar with the axis of insertion. The axis of insertion may be, for example, approximately 45 degrees from the top surface of the base 116 and may be in-line with the canal.

With continued reference to FIGS. 25-30, the base 312 of the anchor 310 has the shape of a low-profile cylinder with an open center 338 and a pair of flattened forward panels 340, as best shown in FIG. 27. As further illustrated in FIGS. 25-30, the base 312 has a proximal upper surface 342 and an opposing distal bone contacting surface 344.

As also shown in FIGS. 25-30, the anchor 310 further includes central keel 320. The central keel 320 extends across the diameter of the open center 338 of base 312. The central keel 320 further extends from the bone contacting surface 344 of the base 312 in a direction opposite the proximal surface 342 such that the central keel 320 has a first length. Importantly, the central keel 320 has a first length such that when implanted into a humeral bone the central keel 320 does not, for example, extend into the diaphysis of the bone. However, the central keel 320 and the base 312 are designed to engage the bone to achieve sufficient short and long term fixation.

The central keel 320 has a first length of not more than 45 millimeters and preferably not more than 40 millimeters. In the most preferred embodiment, the central keel 320 has a length of not more than 35 millimeters. In addition, the central keel 320 may have a length of not more than 30 millimeters. The rear keel 324, the medial keel 328, and the lateral keel 332 have lengths no greater than the length of central keel 320. Moreover, in the preferred embodiment, each keel 324, 328, 332 has a constant cross-sectional shape and volume between an initial bone insertion taper at a distal end 316 and the bone contacting surface 344 at a proximal end 314.

Referring still to FIGS. 25-30, the central keel 320 further includes a plurality of bone rasping fins 322 that extend from the central keel 320. The fins 322 are preferably disposed vertically along the exterior length of the central keel 320. The fins 322 may extend directly or at an angle from the central keel 320. Each fin 322 may be of any desired shape useful in being inserted into the bone.

Returning to FIGS. 25-30, the rear keel 324 extends from the bone contacting surface 344 of the base 312 in a direction opposite the proximal surface 342 of the base 312 and generally parallel to the central keel 320. The rear keel 324 includes a plurality of bone engaging fins 326 that extend from the rear keel 324. The fins 326 are preferably disposed horizontally, perpendicular to the exterior length of the central keel 320. The fins 326 may extend directly or at an angle from the central rear keel 320. Each fin 326 may be of any desired shape useful in being retained in a bone.

With continued reference to FIGS. 25-30, the anchor 310 further includes the medial keel 328. The medial keel 328 extends from the bone contacting surface 344 of the base 312 in a direction opposite the proximal surface 342 of the base 312 and generally parallel to the central keel 320. The medial keel 328 also includes a plurality of bone engaging fins 330 that extend from the medial keel 328. The fins 330 are preferably disposed horizontally, perpendicular to the exterior length of the medial keel 328. The fins 330 may extend directly or at an angle from the medial keel 328. Each fin 330 may be of any desired shape useful in being retained in a bone.

Referring again to FIGS. 25-30, the lateral keel 332 extends from the bone contacting surface 344 of the base 312 in a direction opposite the proximal surface 342 of the base 312 and generally parallel to the central keel 320. The lateral keel 332 includes a plurality of bone engaging fins 334 that extend from the lateral keel 332. The fins 334 are preferably disposed horizontally, perpendicular to the exterior length of the lateral keel 332. Fins 334 may extend directly or at an angle from lateral keel 332. Each fin 334 may be of any desired shape useful in being retained in a bone.

Figure 44:
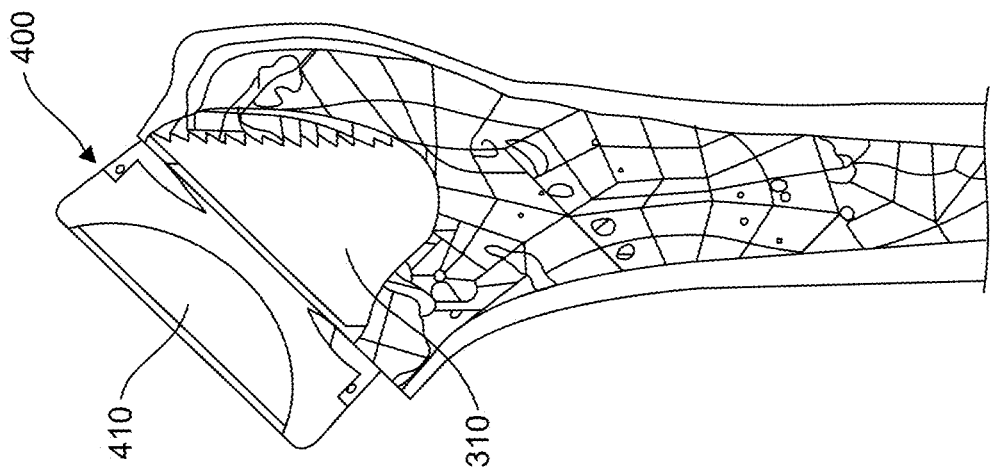
FIG. 44 is a side, cross-sectional view of the reverse stemless shoulder implant assembly of FIG. 38 implanted in a bone, in accordance with an aspect of the present invention.
Figure 43:
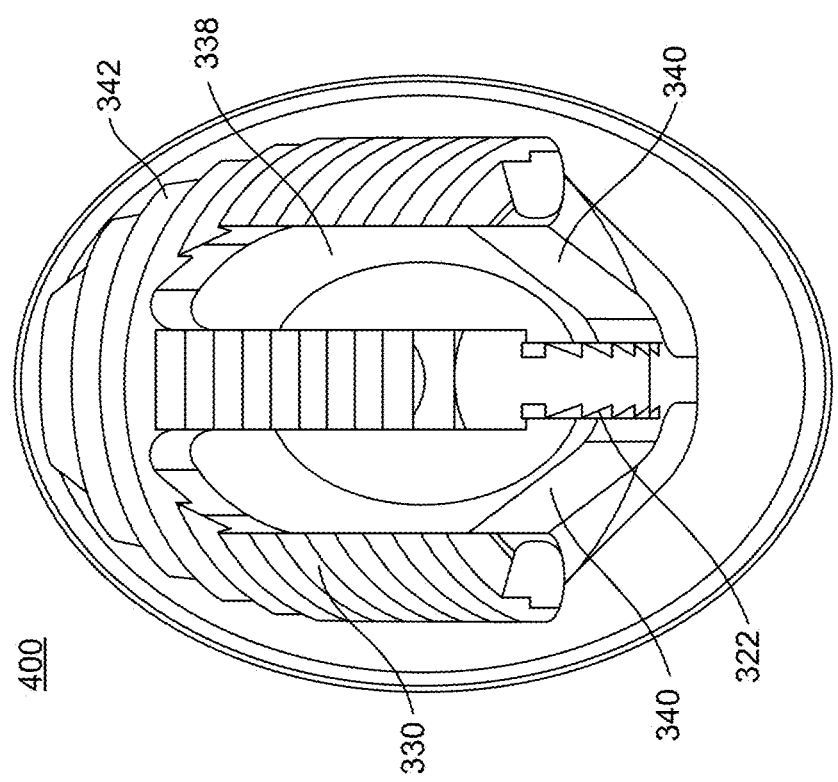
FIG. 43 is a bottom view of the reverse stemless shoulder implant assembly of FIG. 38, in accordance with an aspect of the present invention.
Figure 45:
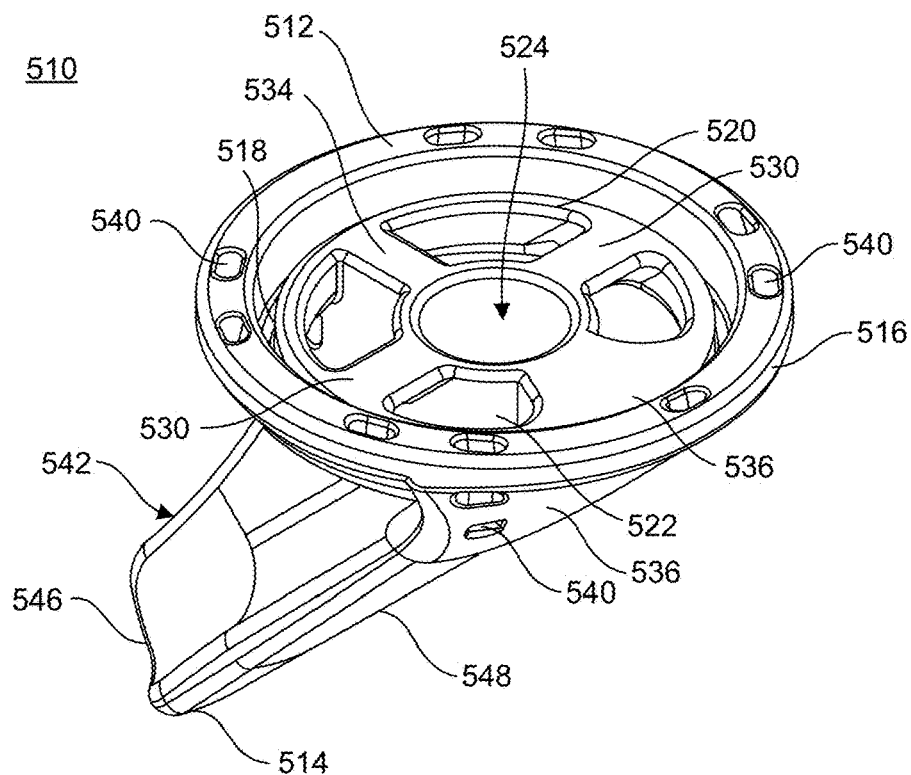
FIG. 45 is a first perspective view of an embodiment of a stemmed humeral implant, in accordance with an aspect of the present invention.
Figure 46:
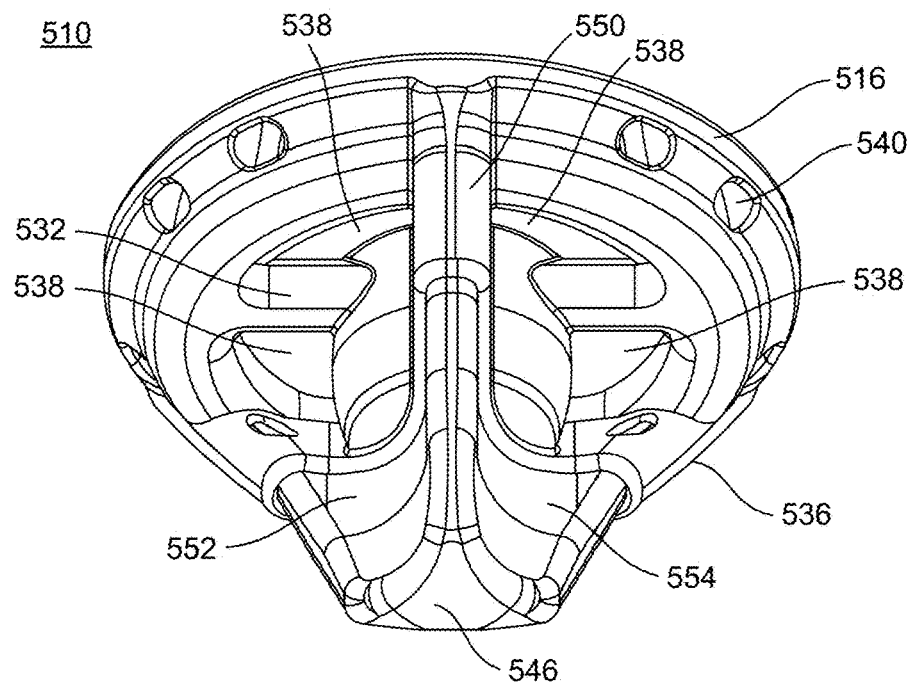
FIG. 46 is a second perspective view of the stemmed humeral implant of FIG. 45, in accordance with an aspect of the present invention.

Referring now to FIGS. 38-44 and with continued reference to FIGS. 25-30, there is shown several views of a shoulder implant assembly 300 including anchor 310 attached to a humeral head 350. The humeral head 350 is a common component of its type having a convex outer articular surface 352 and an anchor engaging surface 354. The humeral head 350 is attached to the anchor 310 by common mechanical means, for example, a coupling member. FIG. 44 shows the implant 300 inserted in a humeral bone.

Referring now to FIGS. 38-44, there is shown several views of a reverse shoulder implant assembly 400 including the anchor 310 attached to the articular component 410. The articular component 410 is a common component of its type having a concave outer articular surface 412 and an anchor engaging surface 354. The articular component 410 is attached to the anchor 310 by common mechanical means, for example, a coupling member. FIG. 44 shows the implant 400 inserted in a humeral bone.

Advantageously, the finned shape and short keel length allow the anchor 310, the implant 300, or the implant 400 to be inserted vertically into a resected humeral bone without significant preparation. Indeed, only a punch is needed prior to inserting the anchor 310 into the bone.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Figure 53:
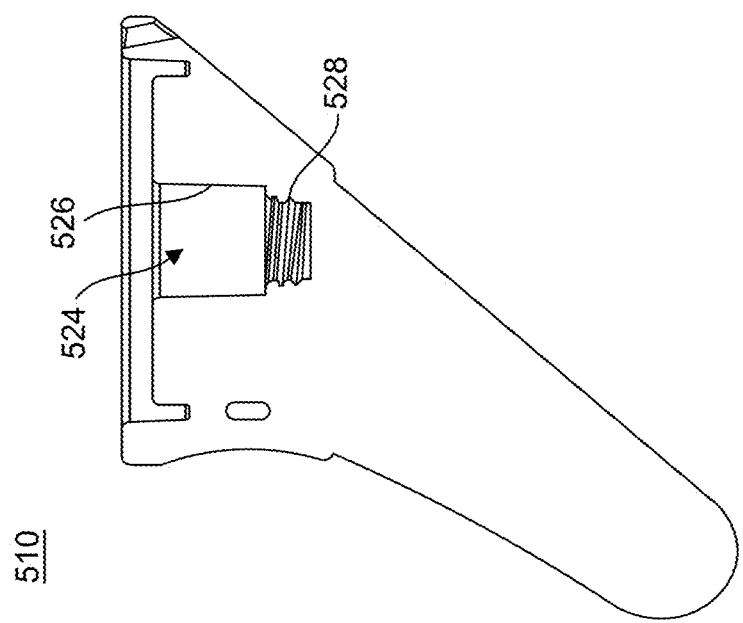
FIG. 53 is a cross-sectional view of the stemmed humeral implant of FIG. 45 taken along line 53-53 in FIG. 51, in accordance with an aspect of the present invention.
Figure 55:
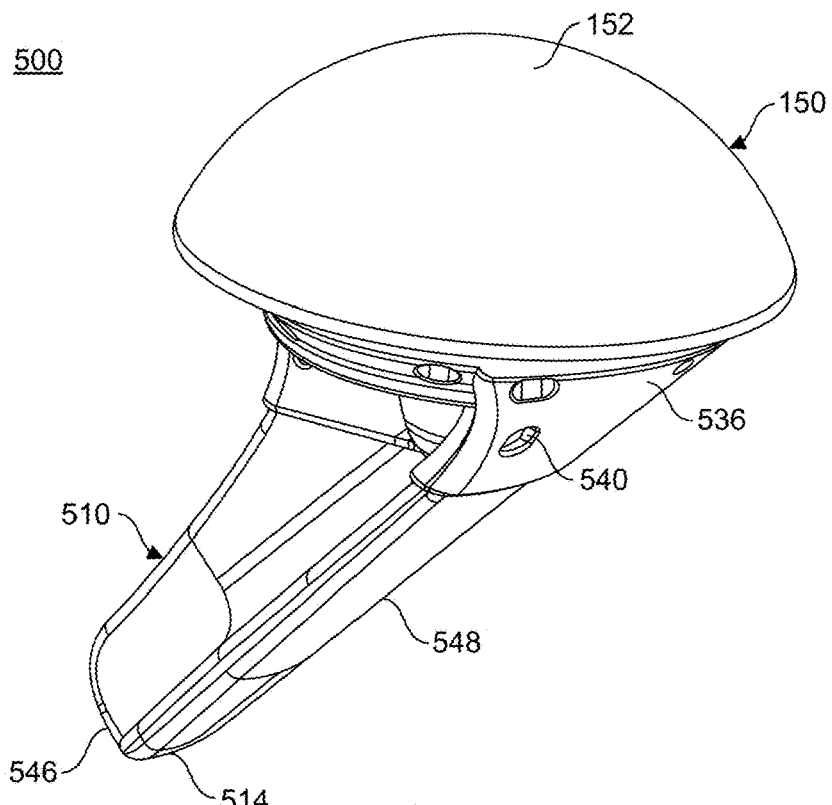
FIG. 55 is a first perspective view of a stemmed implant system including the stemmed humeral implant of FIG. 45, in accordance with an aspect of the present invention.
Figure 56:
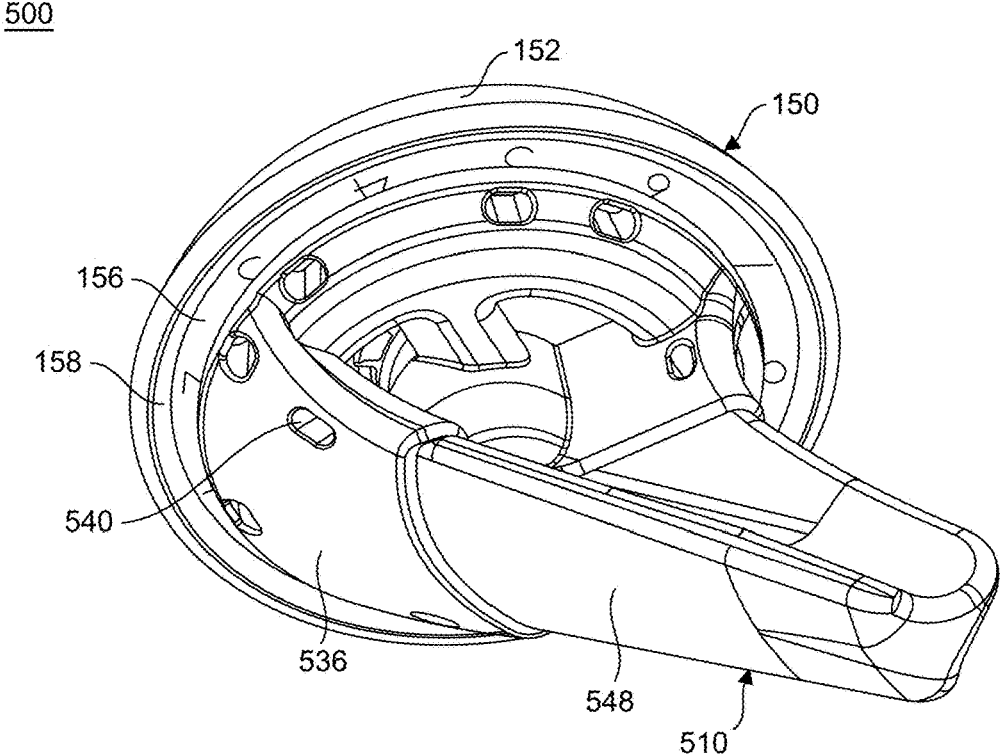
FIG. 56 is a second perspective view of the stemmed implant system of FIG. 45, in accordance with an aspect of the present invention.
Figure 57:
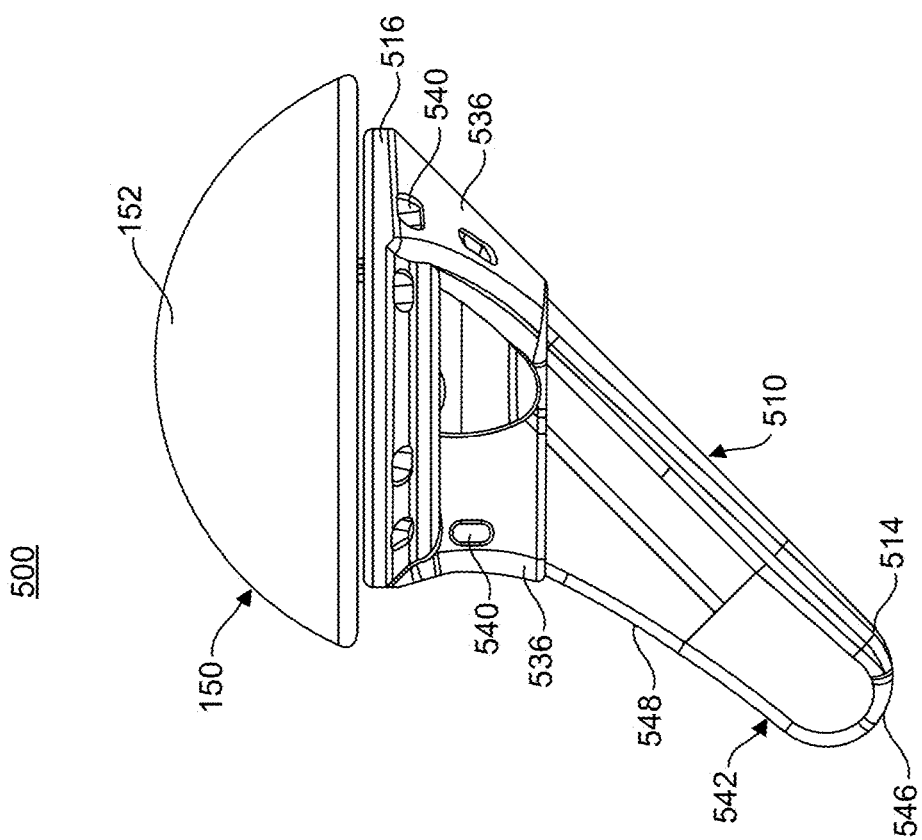
FIG. 57 is a first side view of the stemmed implant system of FIG. 45, in accordance with an aspect of the present invention.
Figure 58:
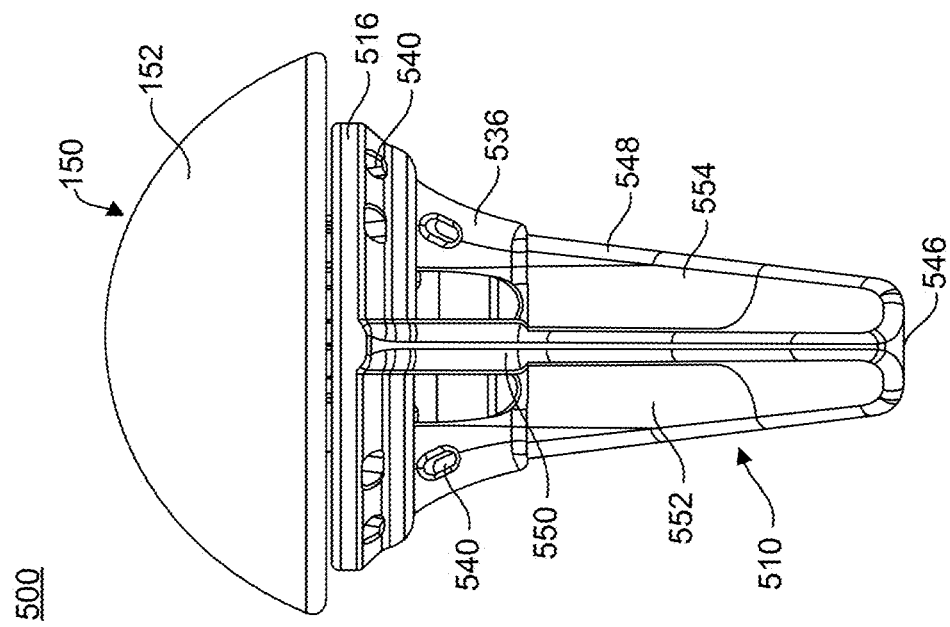
FIG. 58 is a medial view of the stemmed implant system of FIG. 45, in accordance with an aspect of the present invention.
Figure 61:
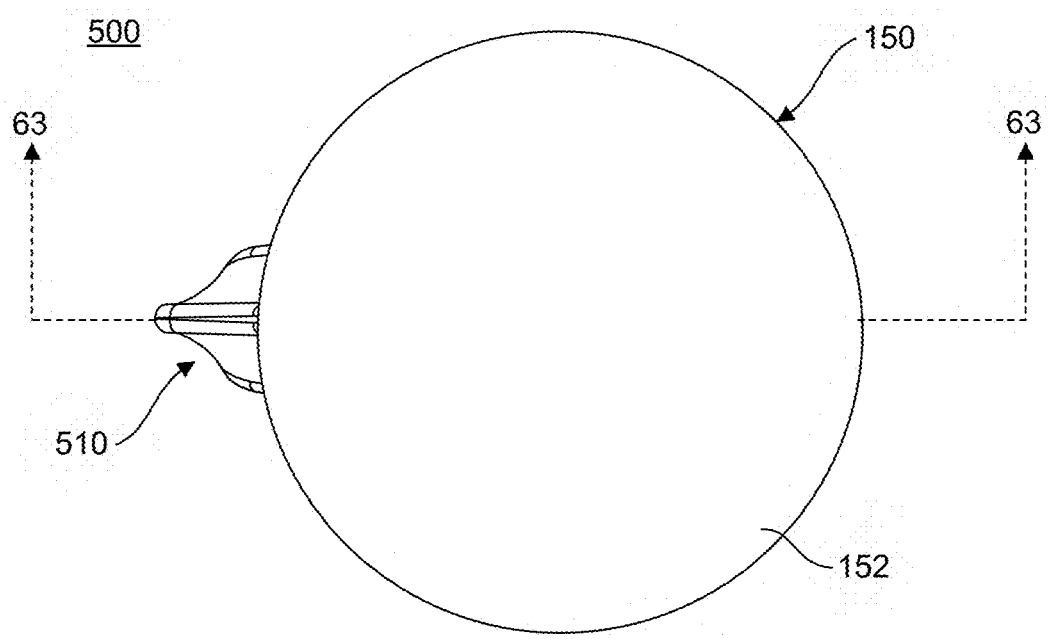
FIG. 61 is a top view of the stemmed implant system of FIG. 45, in accordance with an aspect of the present invention.
Figure 62:
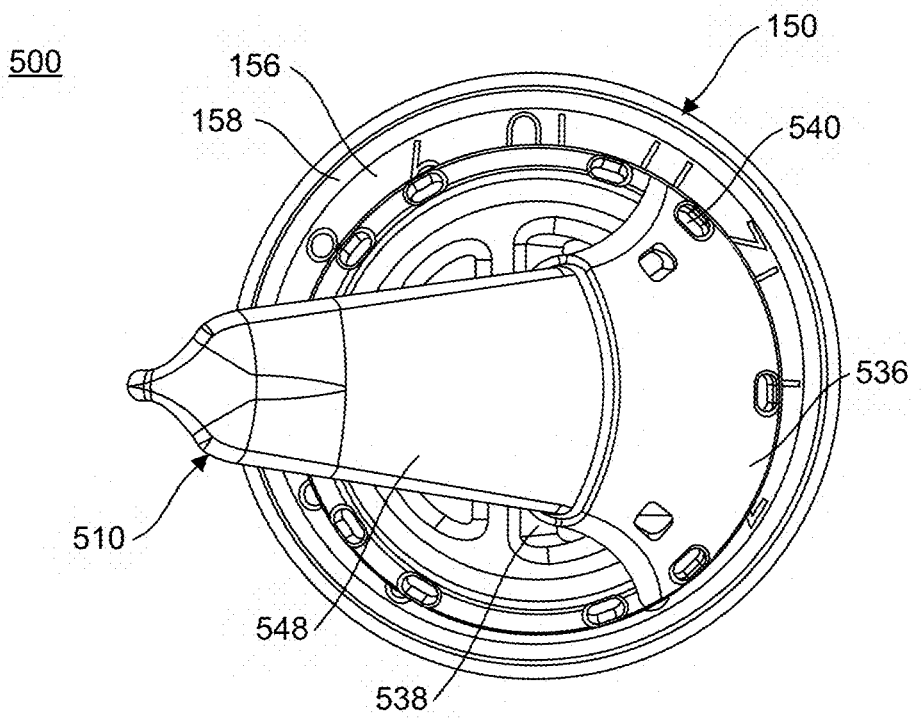
FIG. 62 is a bottom view of the stemmed implant system of FIG. 45, in accordance with an aspect of the present invention.
Figure 63:
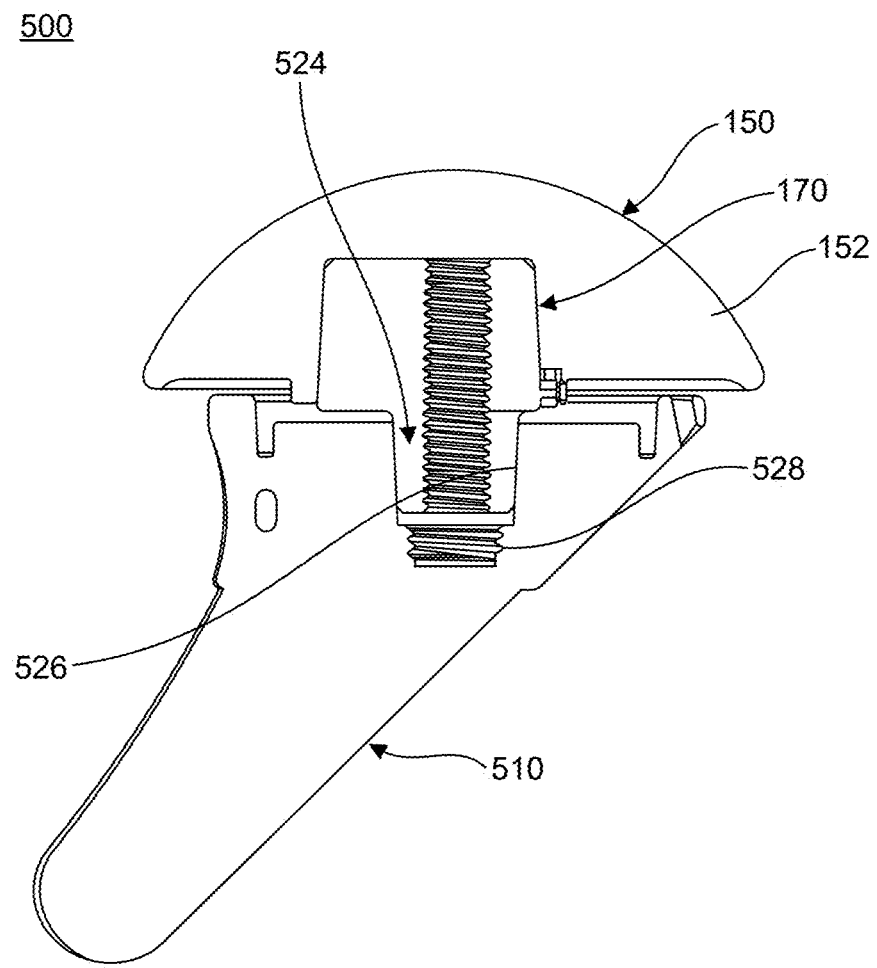
FIG. 63 is a cross-sectional view of the stemmed implant system of FIG. 45 taken along line 63-63 in FIG. 61, in accordance with an aspect of the present invention.
Figure 65:
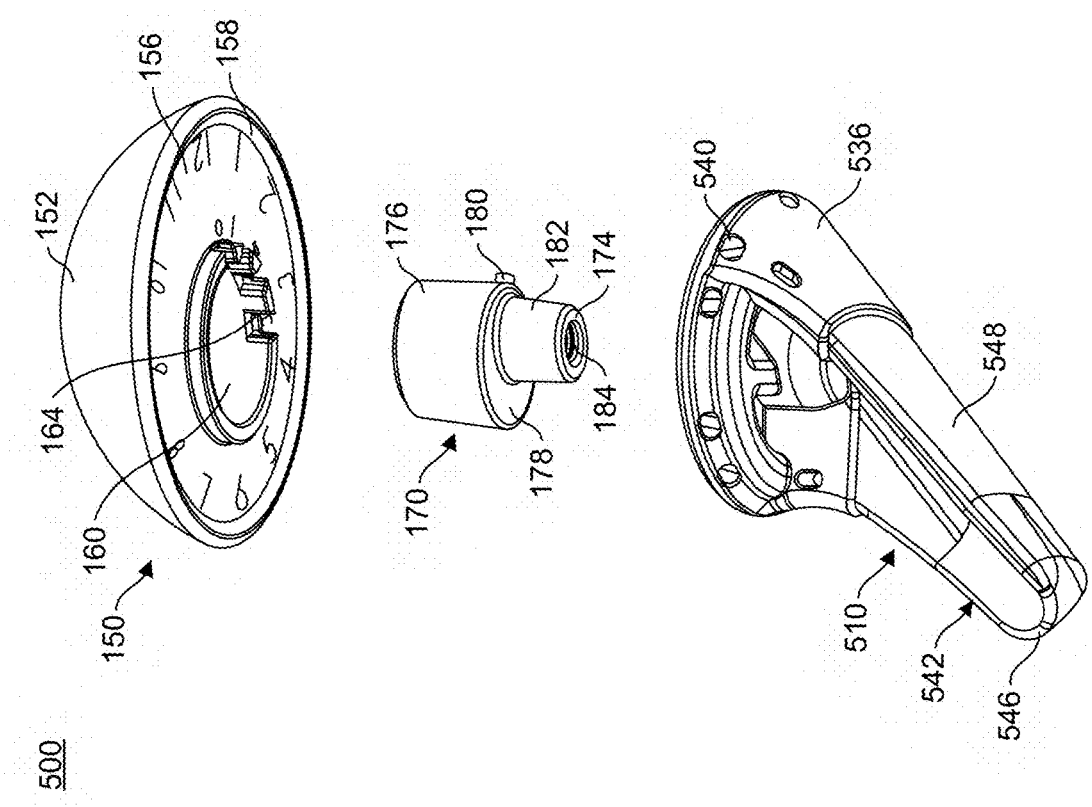
FIG. 65 is an exploded second perspective view of the stemmed implant system of FIG. 45, in accordance with an aspect of the present invention.
Figure 64:
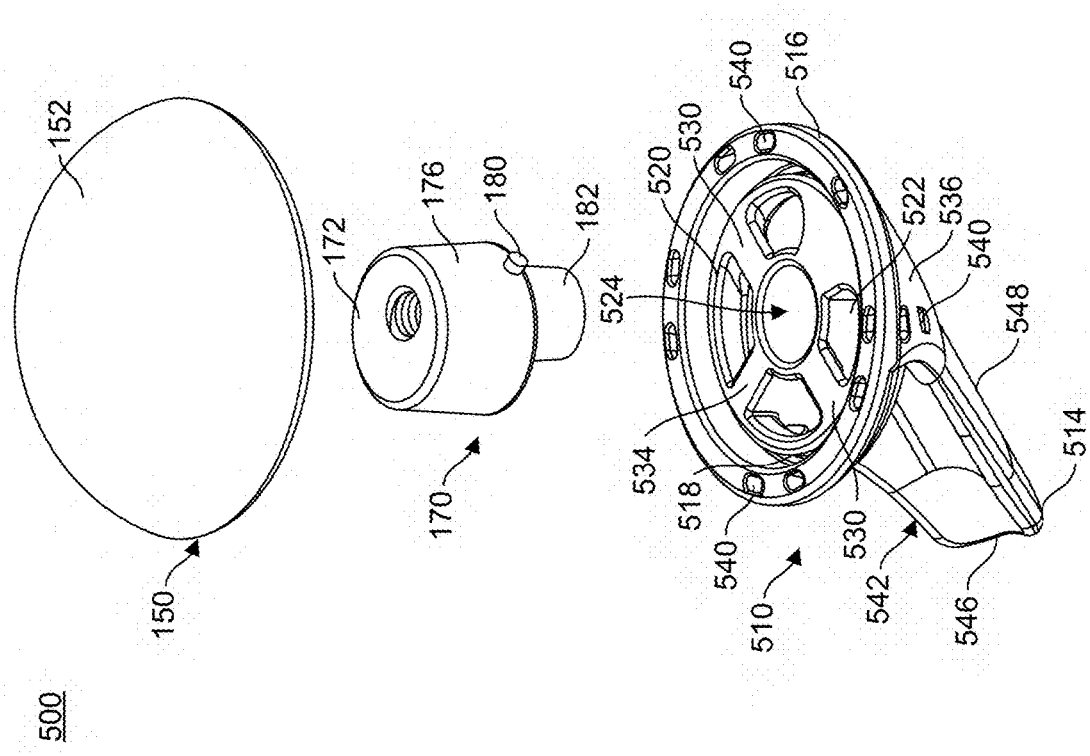
FIG. 64 is an exploded first perspective view of the stemmed implant system of FIG. 45, in accordance with an aspect of the present invention.
Figure 69:
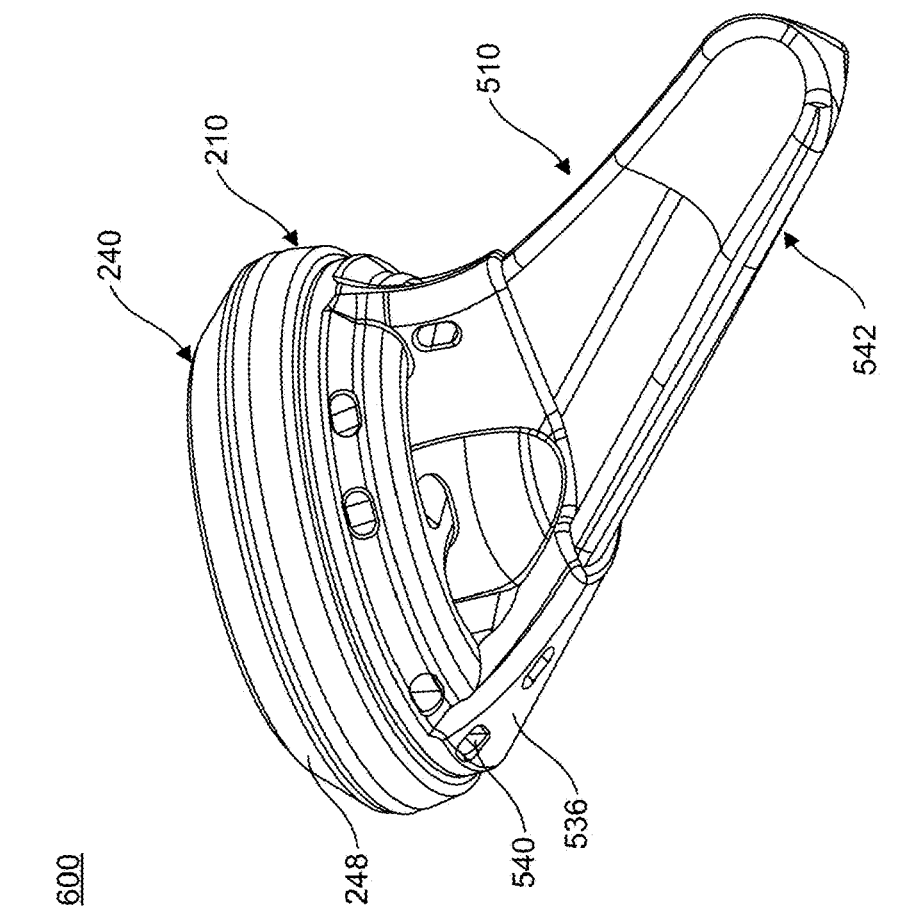
FIG. 69 is a second perspective view of the implant system of FIG. 68, in accordance with an aspect of the present invention.
Figure 68:
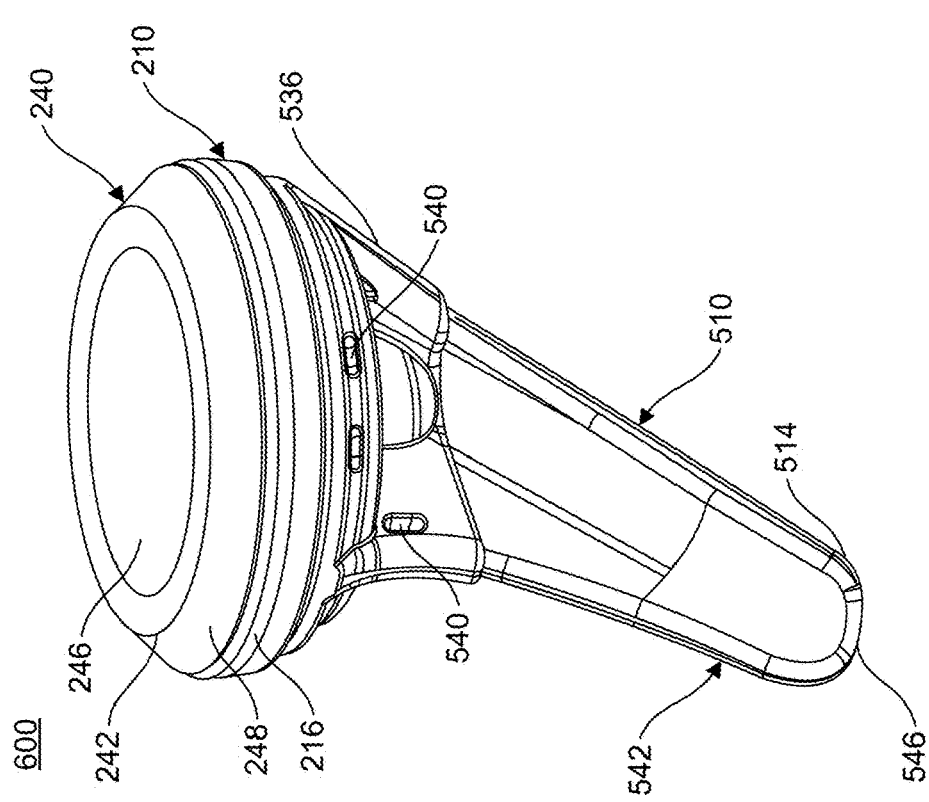
FIG. 68 is a first perspective view of another embodiment of an implant system, in accordance with an aspect of the present invention.
Figure 71:
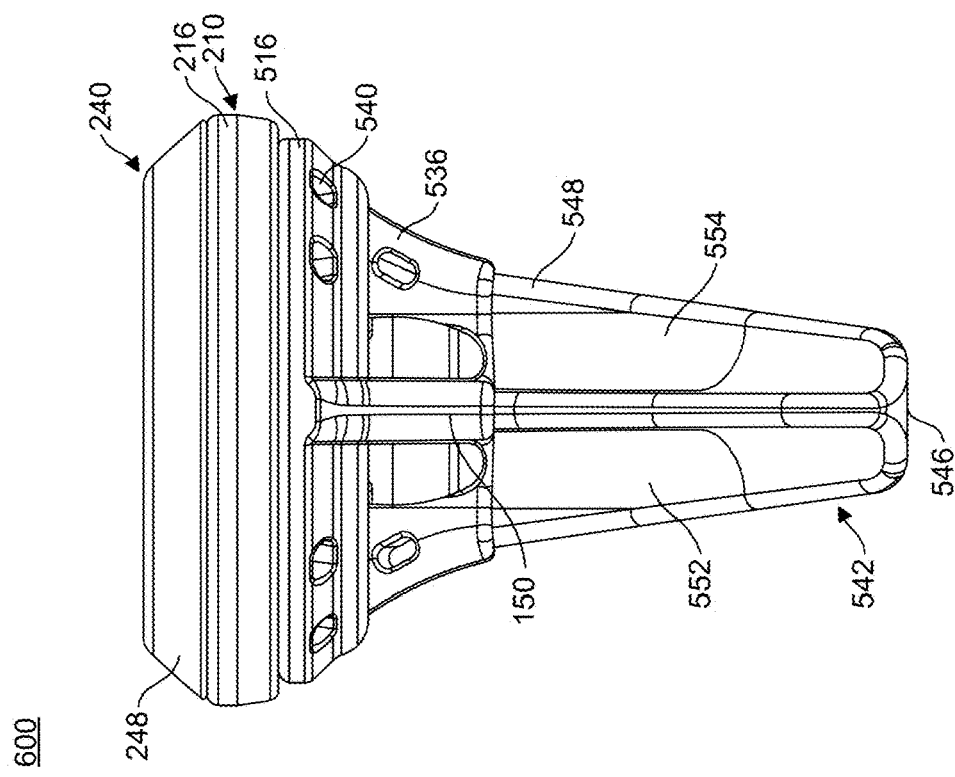
FIG. 71 is a medial view of the implant system of FIG. 68, in accordance with an aspect of the present invention.
Figure 70:
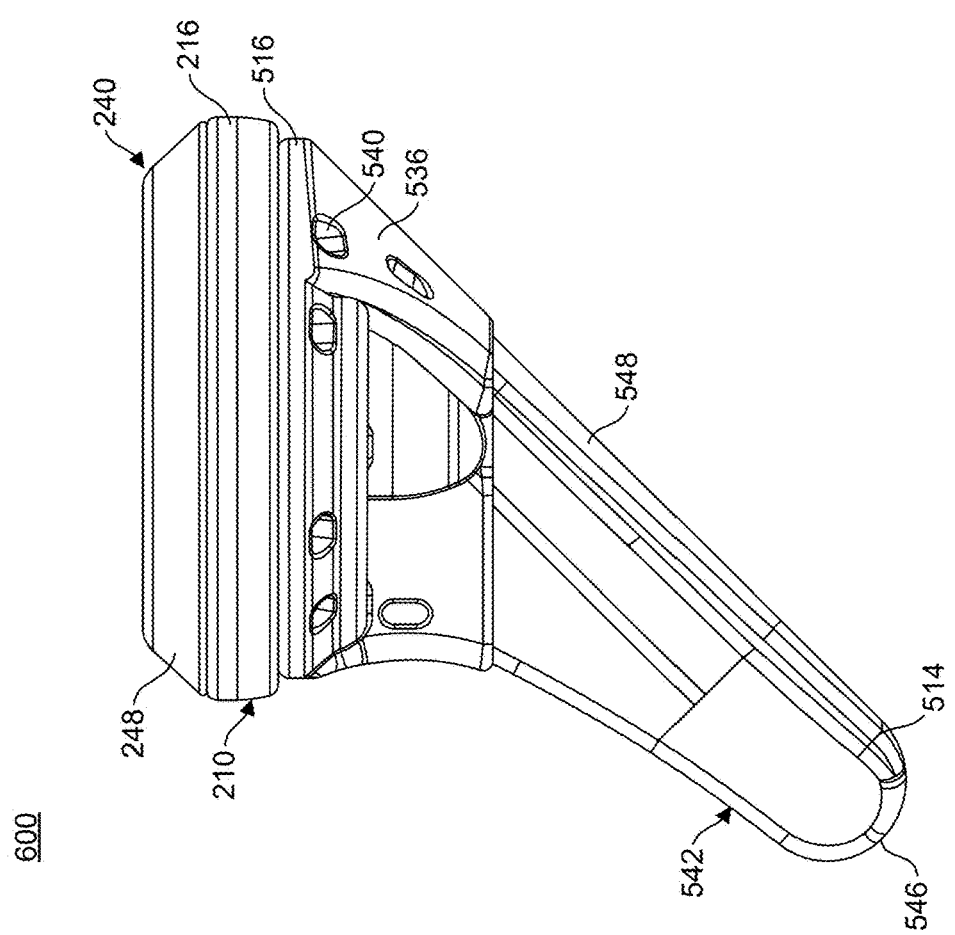
FIG. 70 is a first side view of the implant system of FIG. 68, in accordance with an aspect of the present invention.
Figure 73:
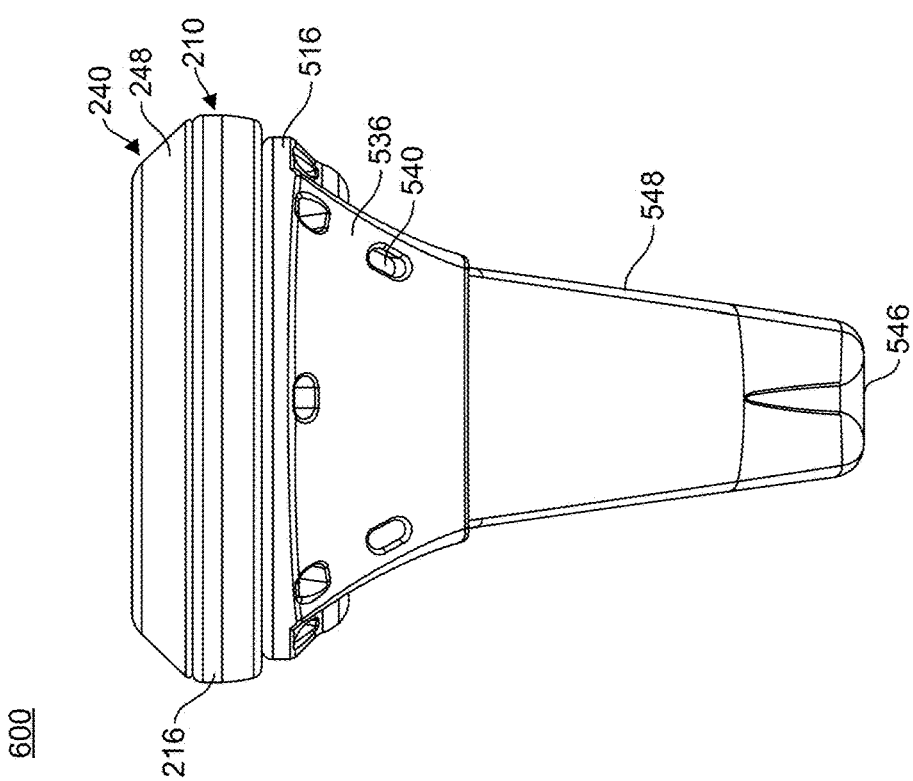
FIG. 73 is a lateral view of the implant system of FIG. 68, in accordance with an aspect of the present invention.
Figure 72:
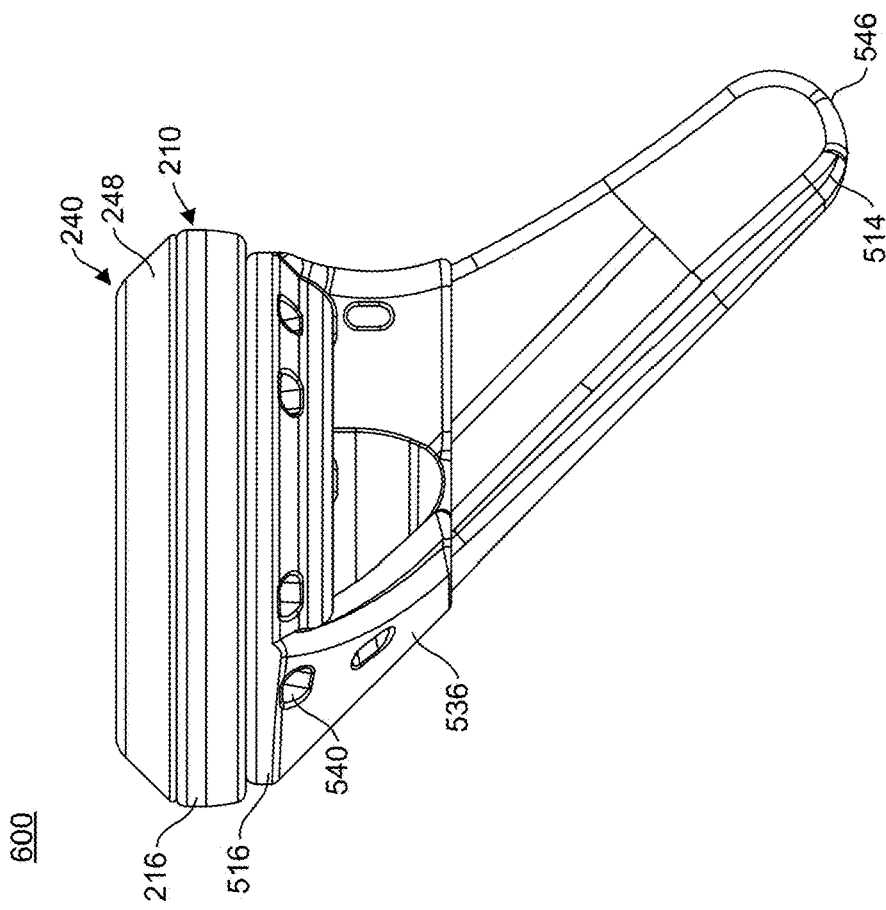
FIG. 72 is a second side view of the implant system of FIG. 68, in accordance with an aspect of the present invention.
Figure 74:
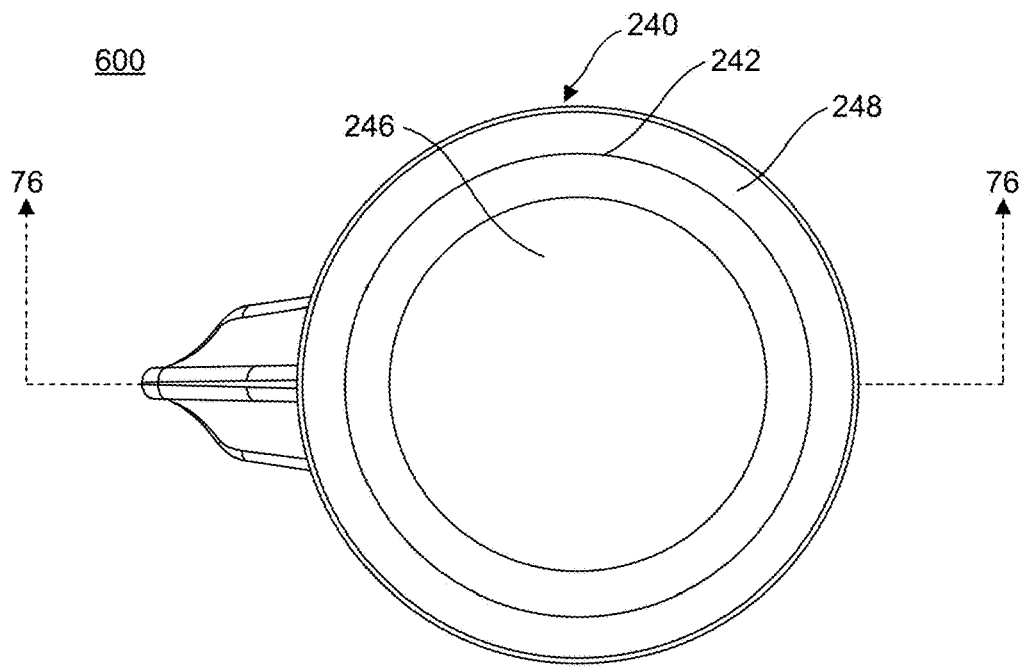
FIG. 74 is a top view of the implant system of FIG. 68, in accordance with an aspect of the present invention.
Figure 75:
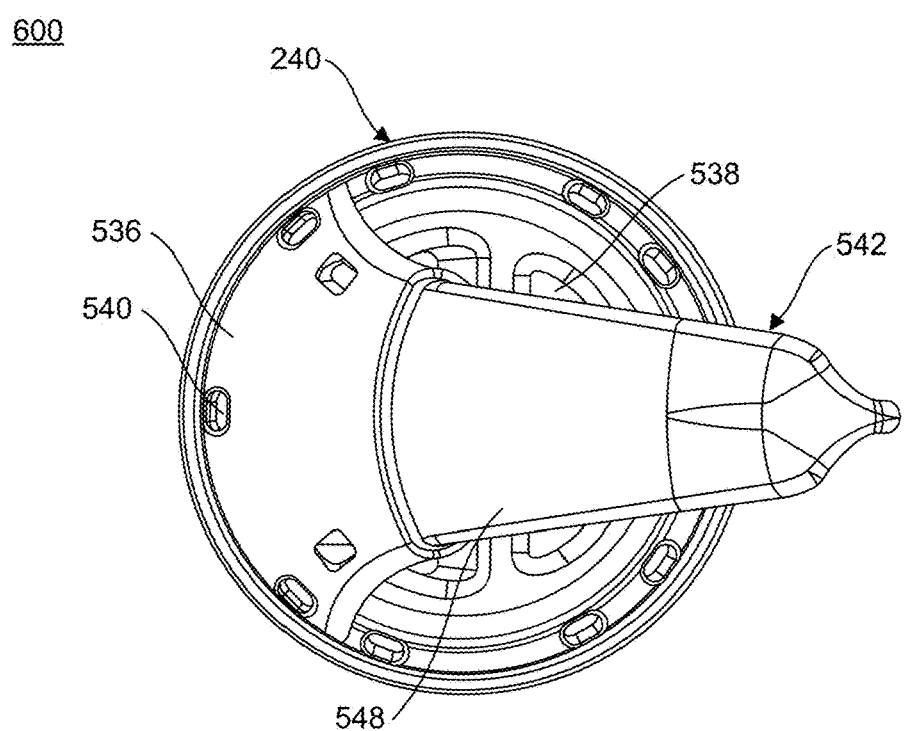
FIG. 75 is a bottom view of the implant system of FIG. 68, in accordance with an aspect of the present invention.
Figure 76:
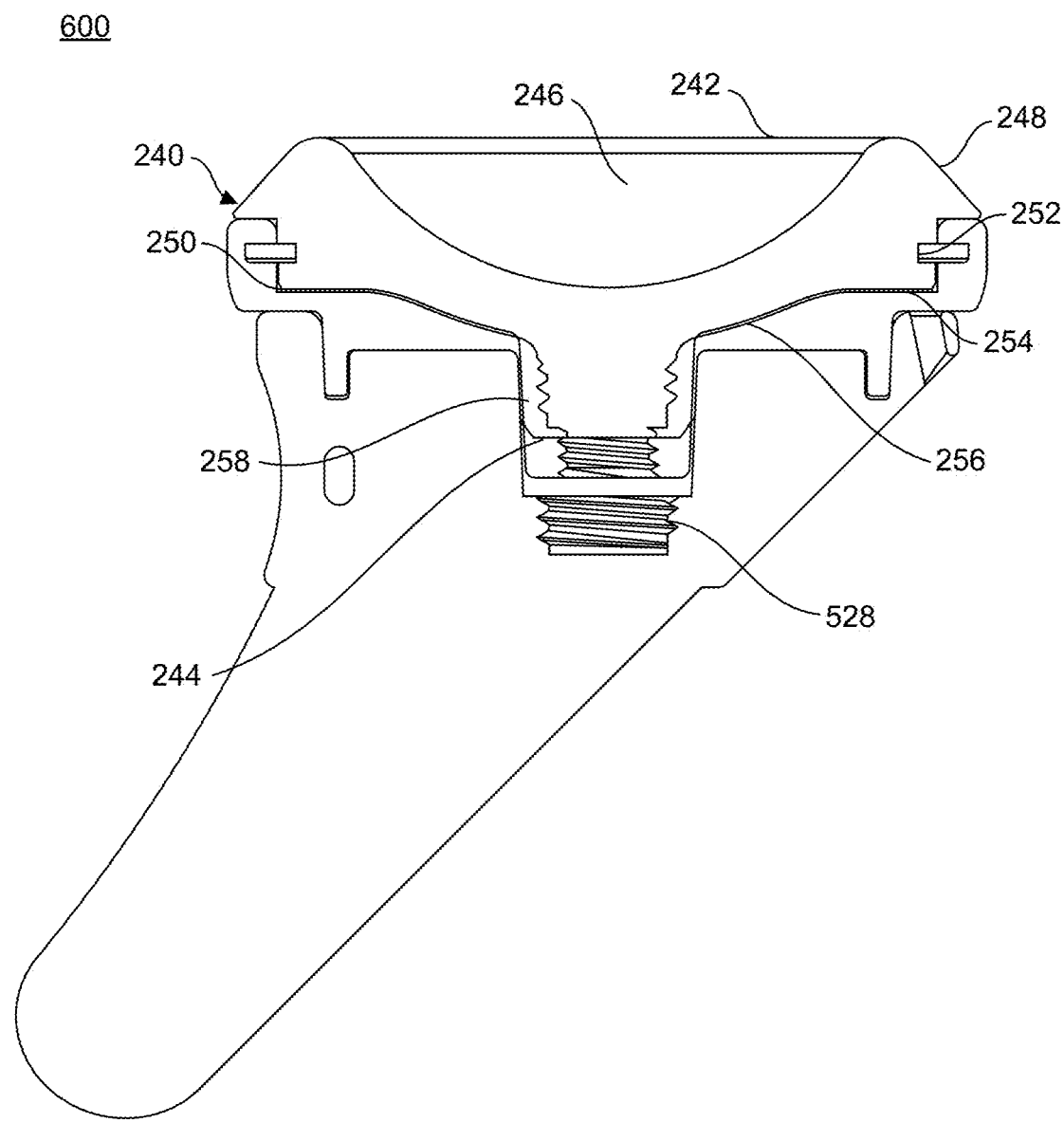
FIG. 76 is a cross-sectional view of the implant system of FIG. 68 taken along line 76-76 in FIG. 74, in accordance with an aspect of the present invention.
Figure 78:
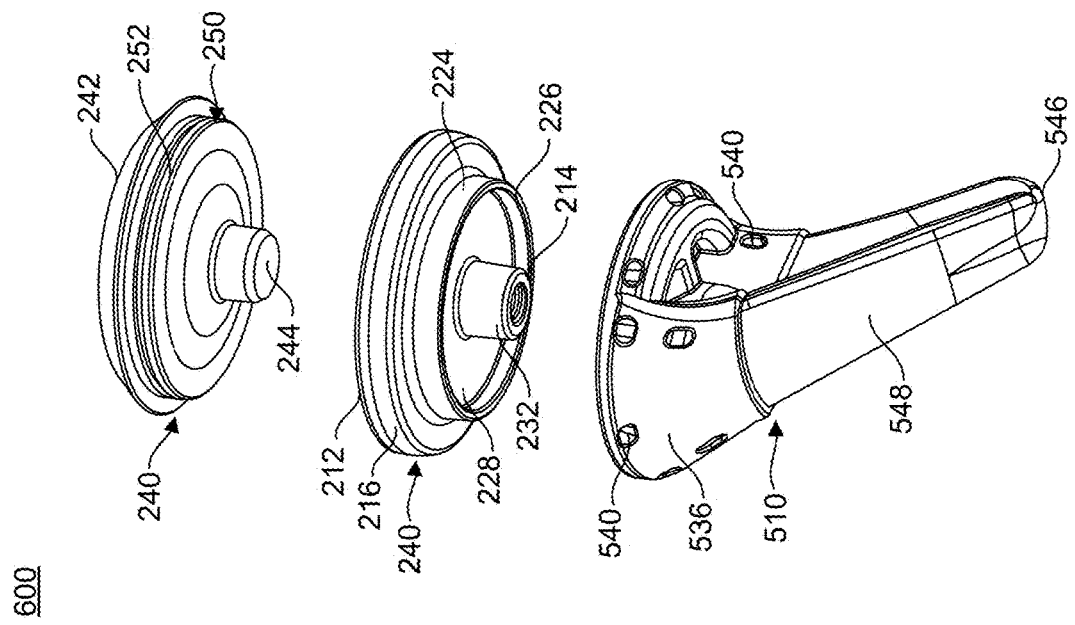
FIG. 78 is an exploded second perspective view of the implant system of FIG. 68, in accordance with an aspect of the present invention.
Figure 77:
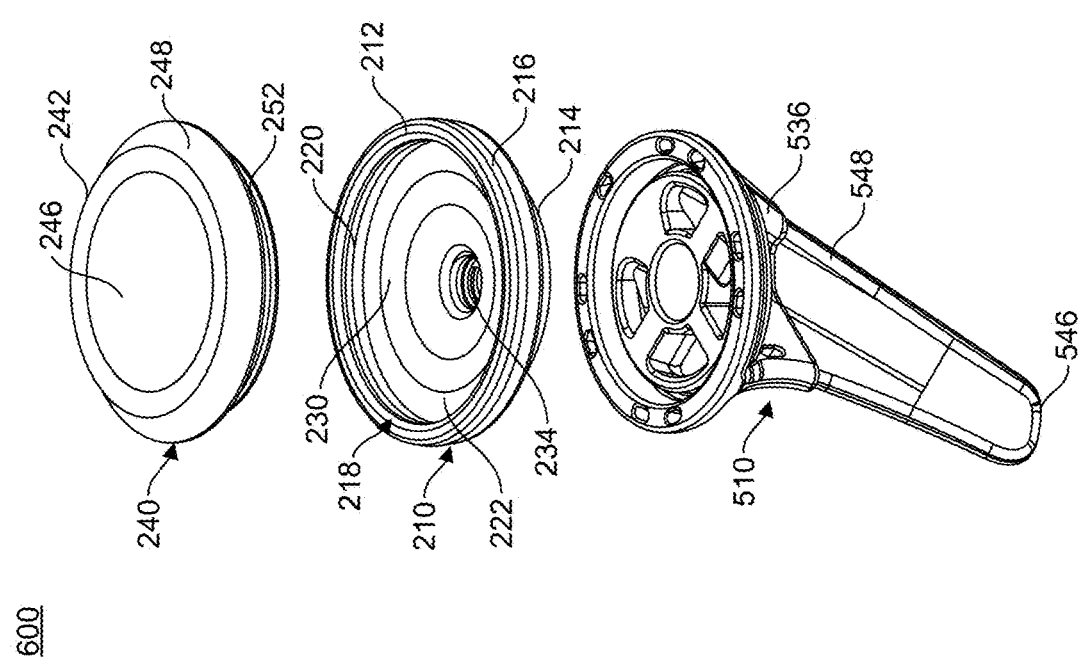
FIG. 77 is an exploded first perspective view of the implant system of FIG. 68, in accordance with an aspect of the present invention.
Figure 82:
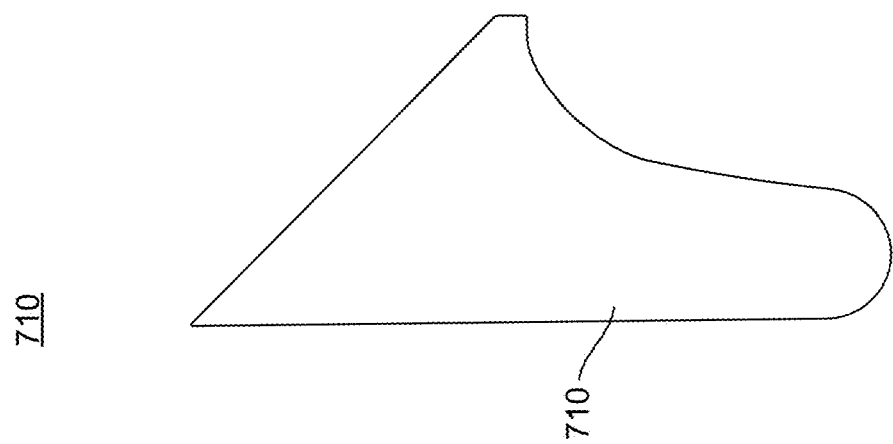
FIG. 82 is a side cross-sectional view of the humeral stem of FIG. 81, in accordance with an aspect the present invention.
Figure 81:
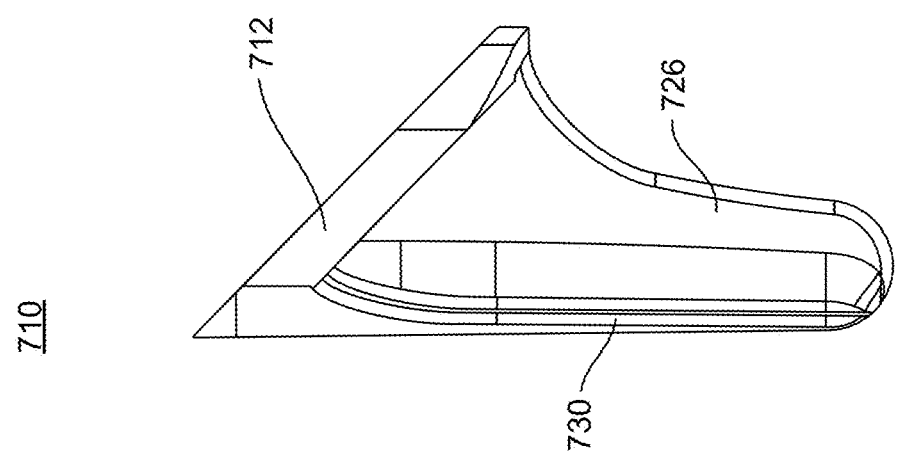
FIG. 81 is a side view of an embodiment of a humeral stem, in accordance with an aspect of the present invention.
Figure 84:
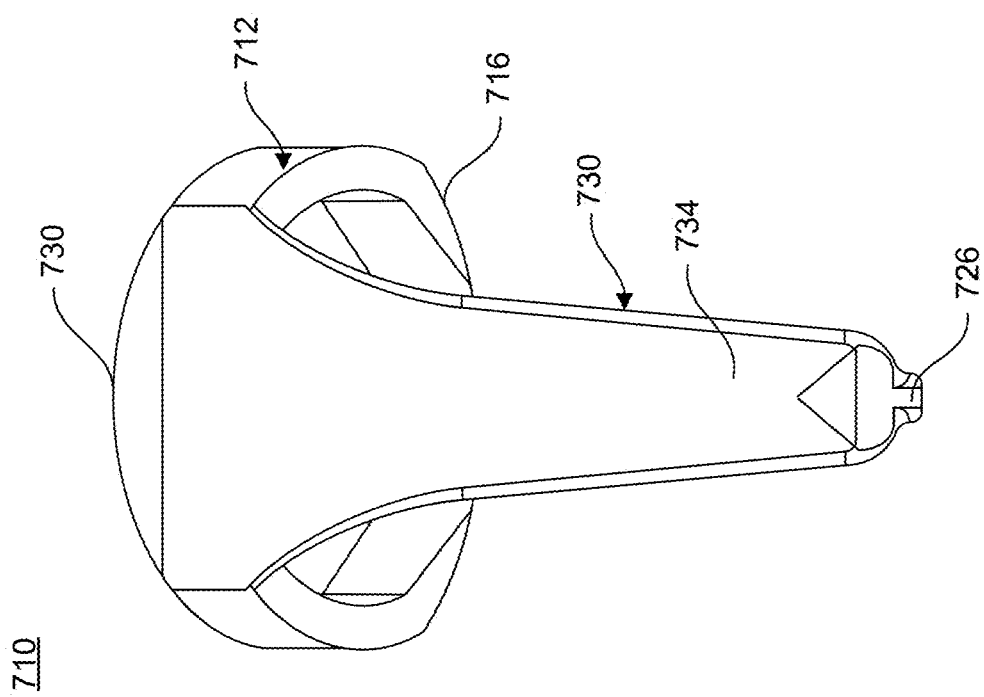
FIG. 84 is a lateral isometric view of the humeral stem of FIG. 81, in accordance with an aspect the present invention.
Figure 83:
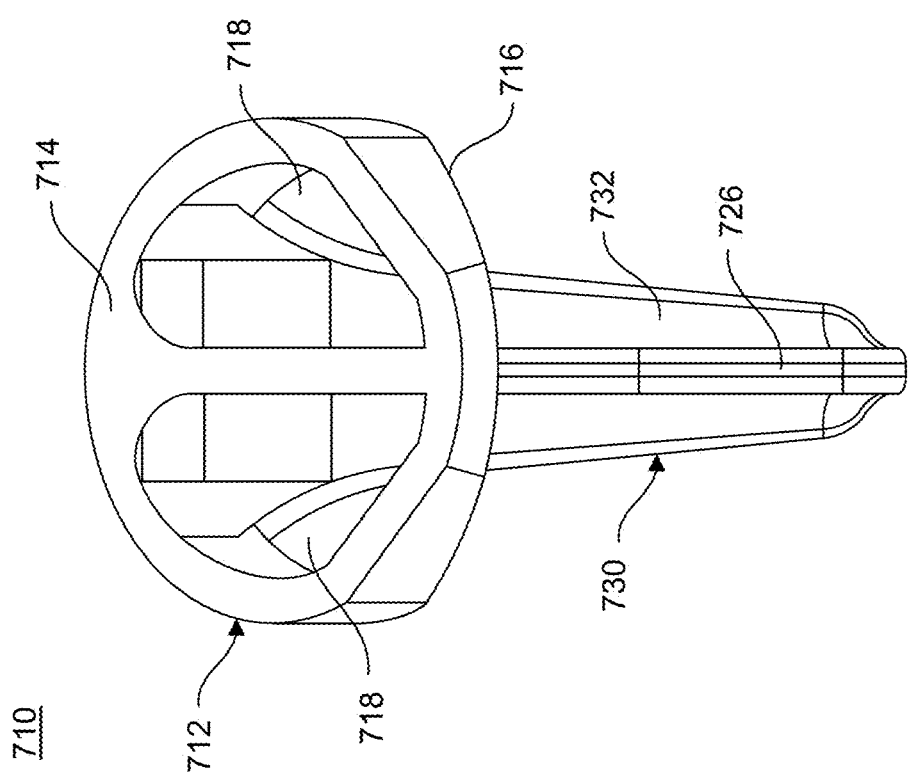
FIG. 83 is a medial isometric view of the humeral stem of FIG. 81, in accordance with an aspect the present invention.
Figure 86:
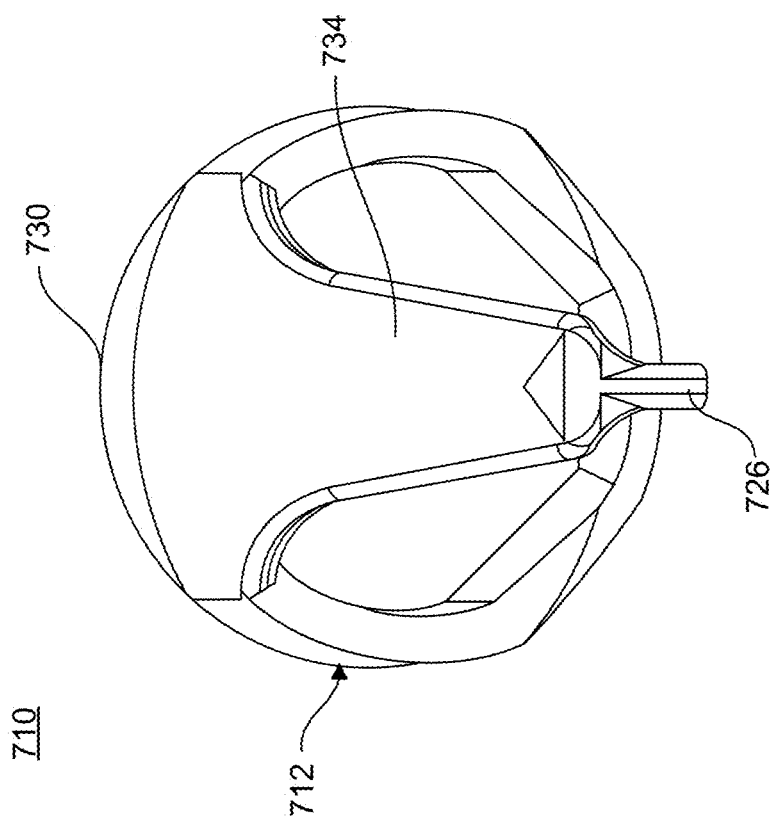
FIG. 86 is a bottom isometric view of the humeral stem of FIG. 81, in accordance with an aspect the present invention.
Figure 85:
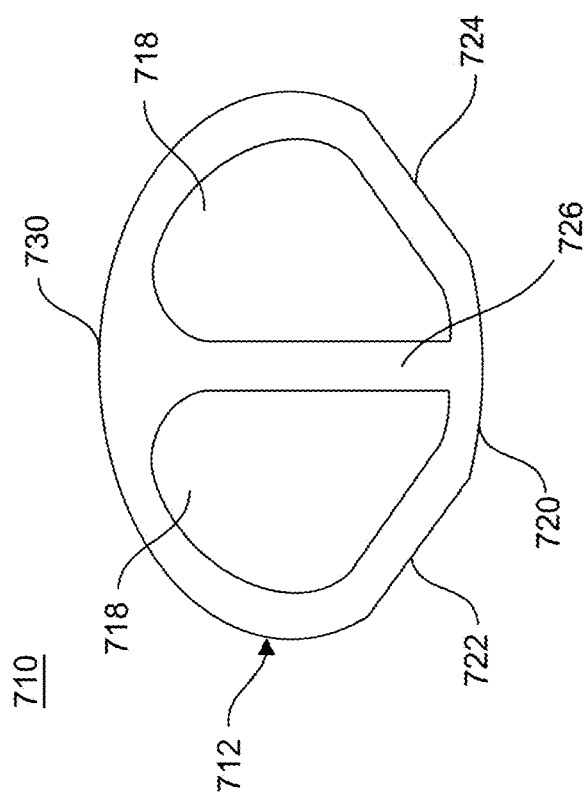
FIG. 85 is a top isometric view of the humeral stem of FIG. 81, in accordance with an aspect the present invention.
Figure 88:
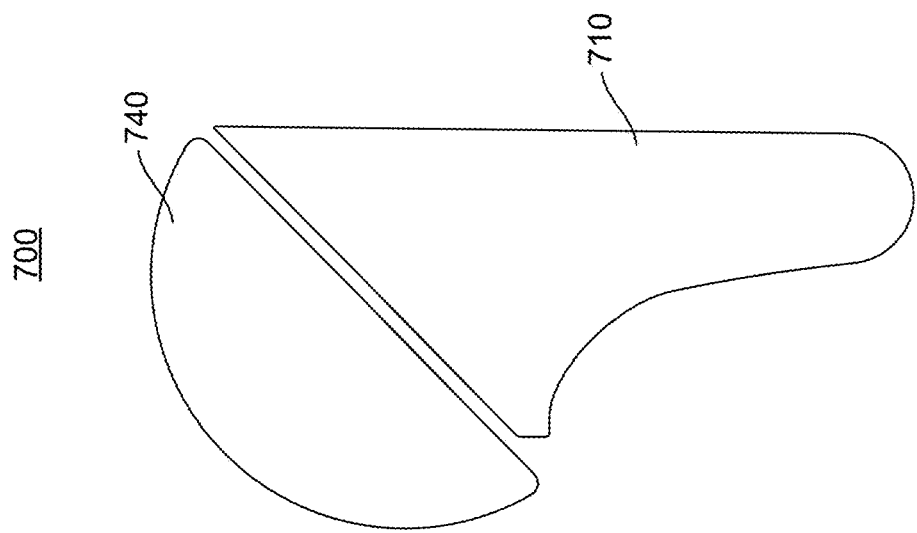
FIG. 88 is a side cross-sectional view of the shoulder implant assembly of FIG. 87, in accordance with an aspect of the present invention.
Figure 87:
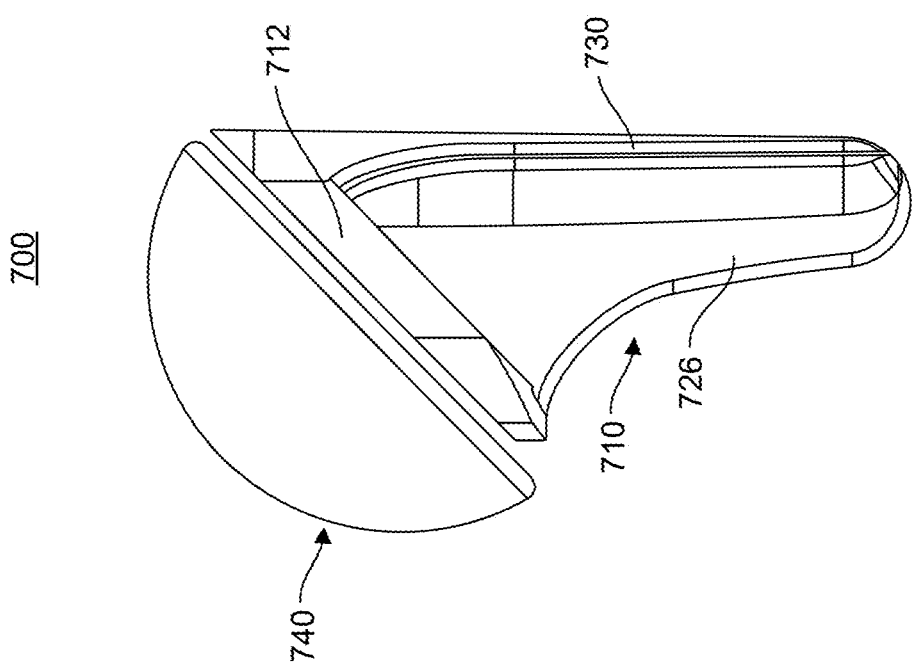
FIG. 87 is a side view of an embodiment of a shoulder implant assembly including the humeral stem of FIG. 81, in accordance with an aspect the present invention.
Figure 90:
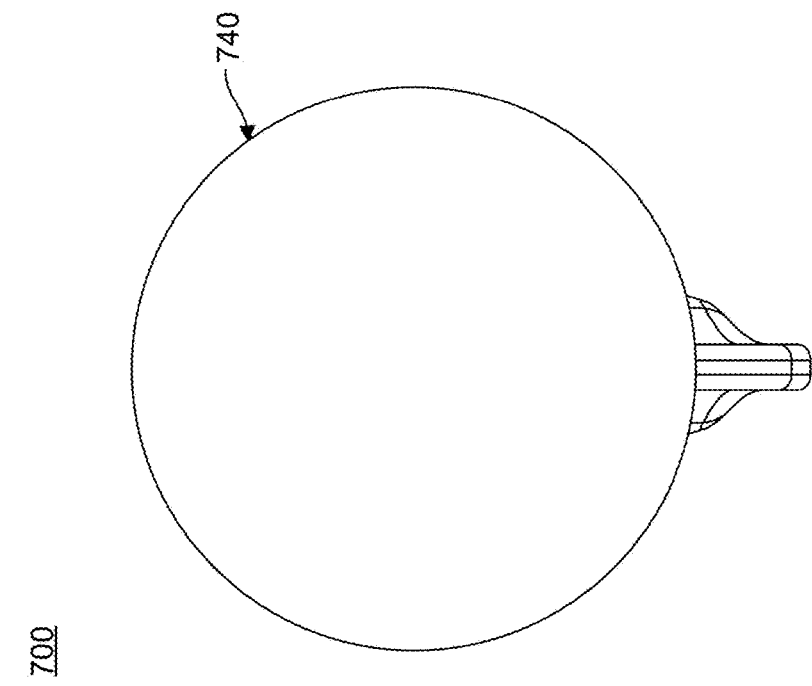
FIG. 90 is a top isometric view of the shoulder implant assembly of FIG. 87, in accordance with an aspect of the present invention.
Figure 89:
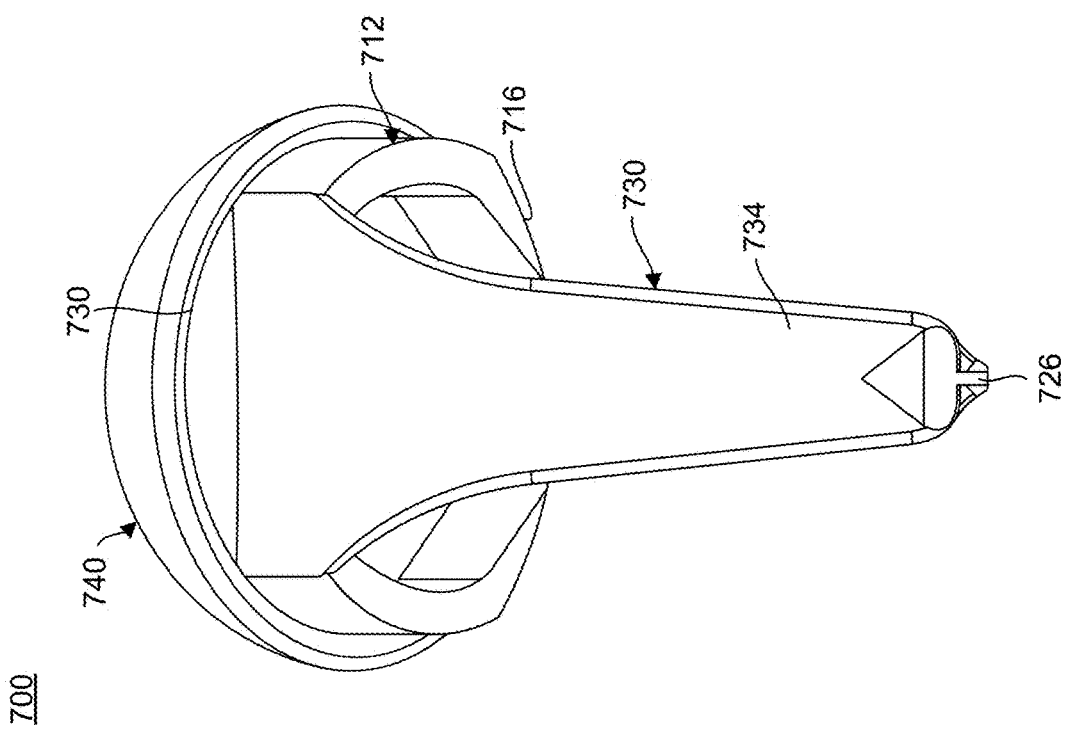
FIG. 89 is a lateral view of the shoulder implant assembly of FIG. 87, in accordance with an aspect of the present invention.
Figure 92:
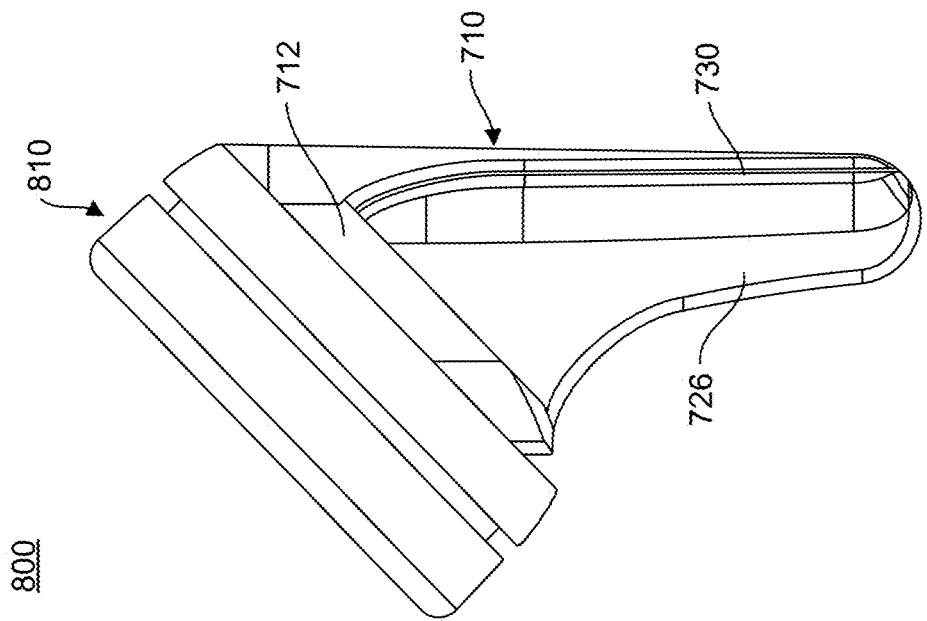
FIG. 92 is a side view of another reverse shoulder implant assembly, in accordance with an aspect of the present invention.
Figure 91:
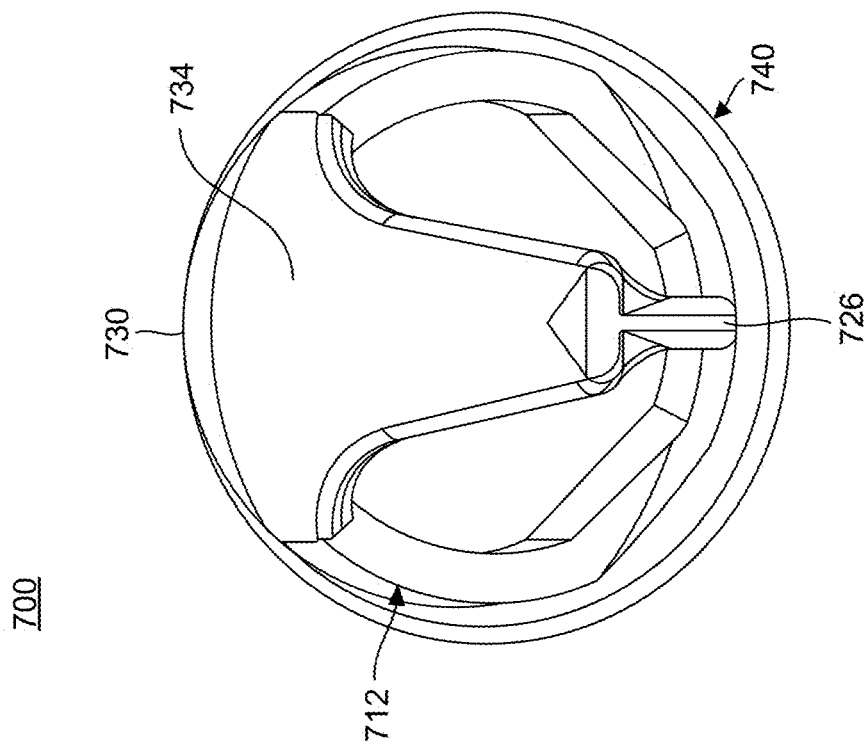
FIG. 91 is a bottom isometric view of the shoulder implant assembly of FIG. 87, in accordance with an aspect of the present invention.
Figure 94:
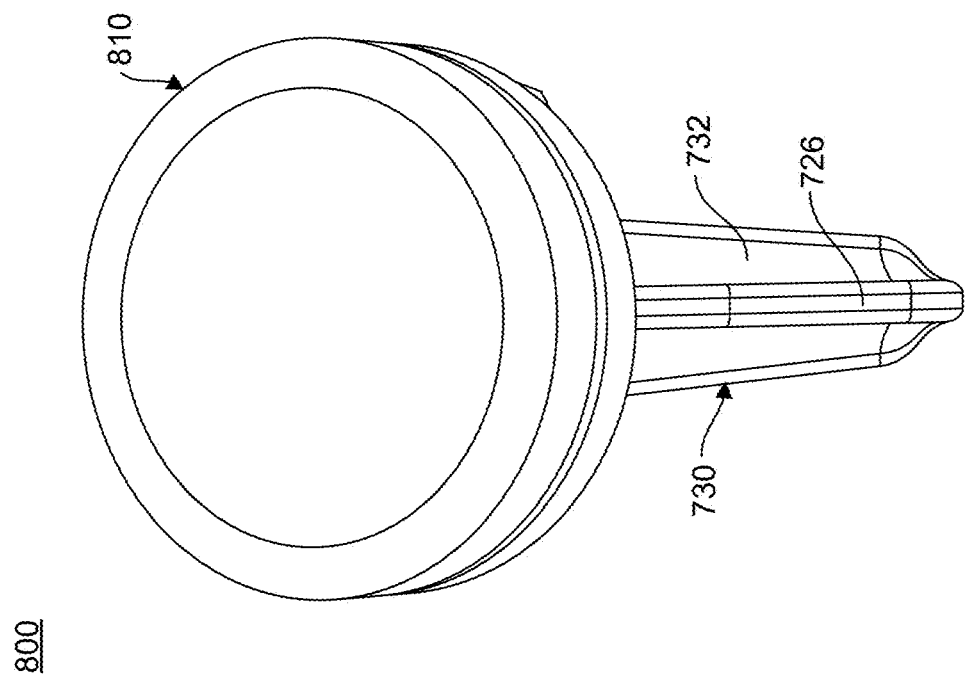
FIG. 94 is a medial view of the reverse shoulder implant assembly of FIG. 92, in accordance with an aspect of the present invention.
Figure 93:
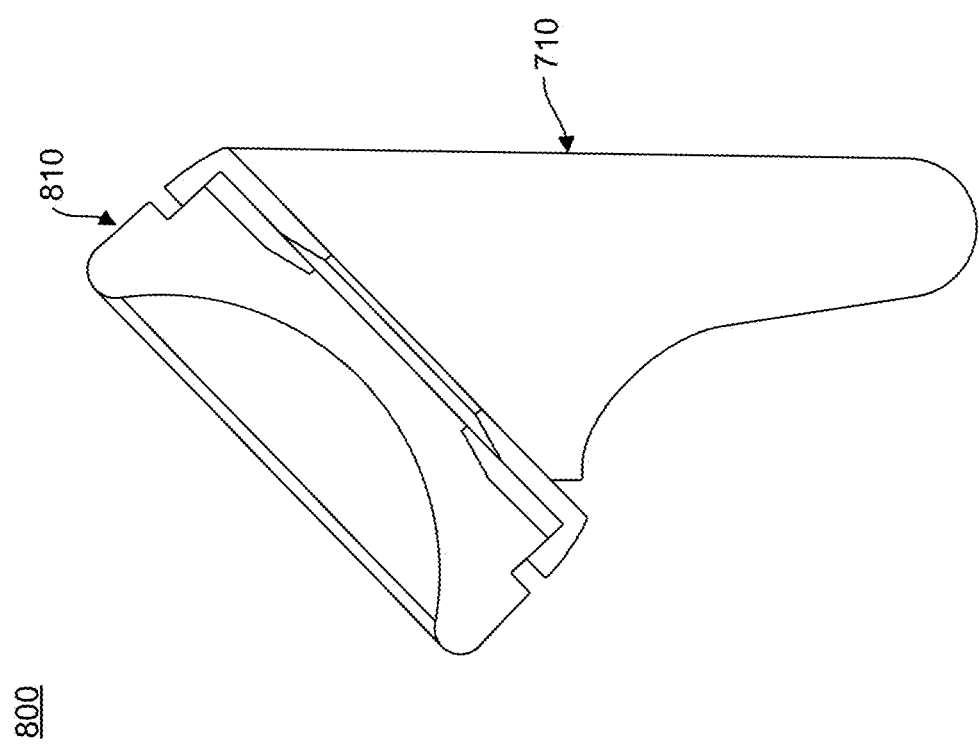
FIG. 93 is a side cross-sectional view of the reverse shoulder implant assembly of FIG. 92, in accordance with an aspect of the present invention.
Figure 96:
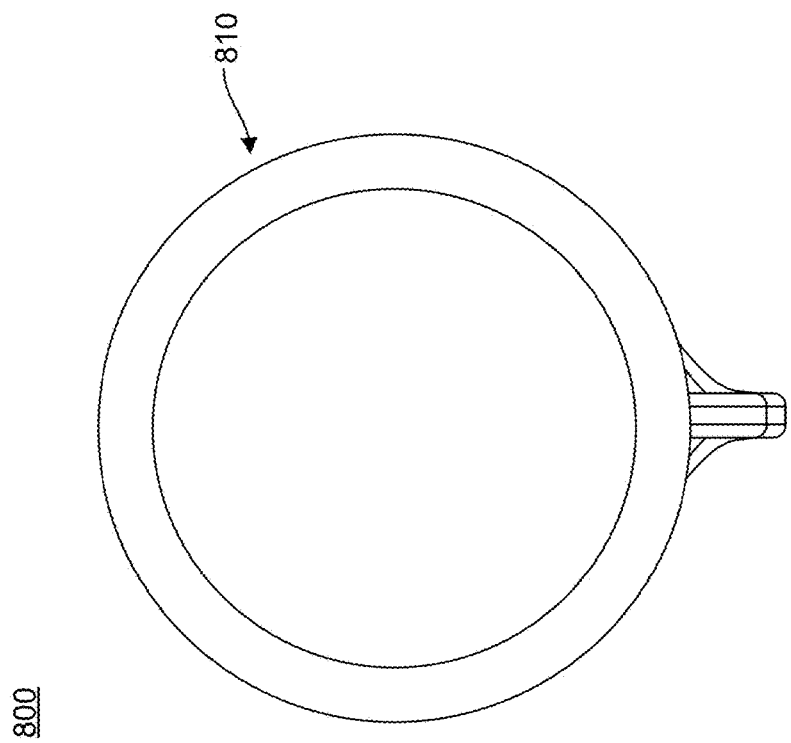
FIG. 96 is a top isometric view of the reverse shoulder implant assembly of FIG. 92, in accordance with an aspect of the present invention.
Figure 95:
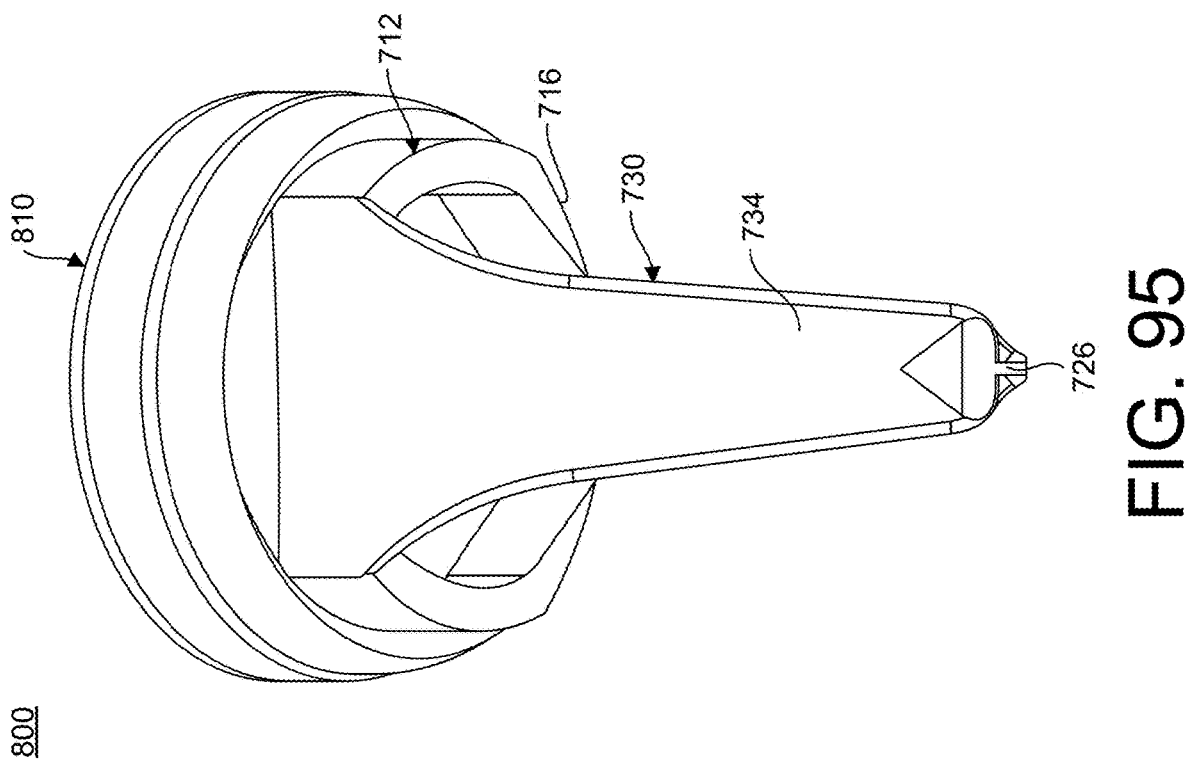
FIG. 95 is a lateral view of the reverse shoulder implant assembly of FIG. 92, in accordance with an aspect of the present invention.
Figure 98:
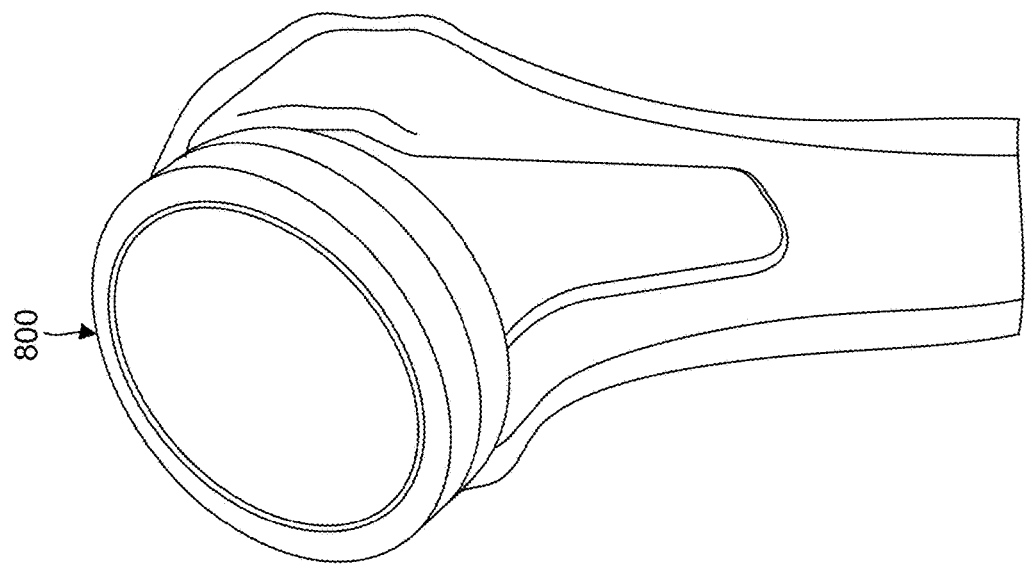
FIG. 98 is a first isometric view of the reverse shoulder implant assembly of FIG. 92 implanted in a bone, in accordance with an aspect of the present invention.
Figure 97:
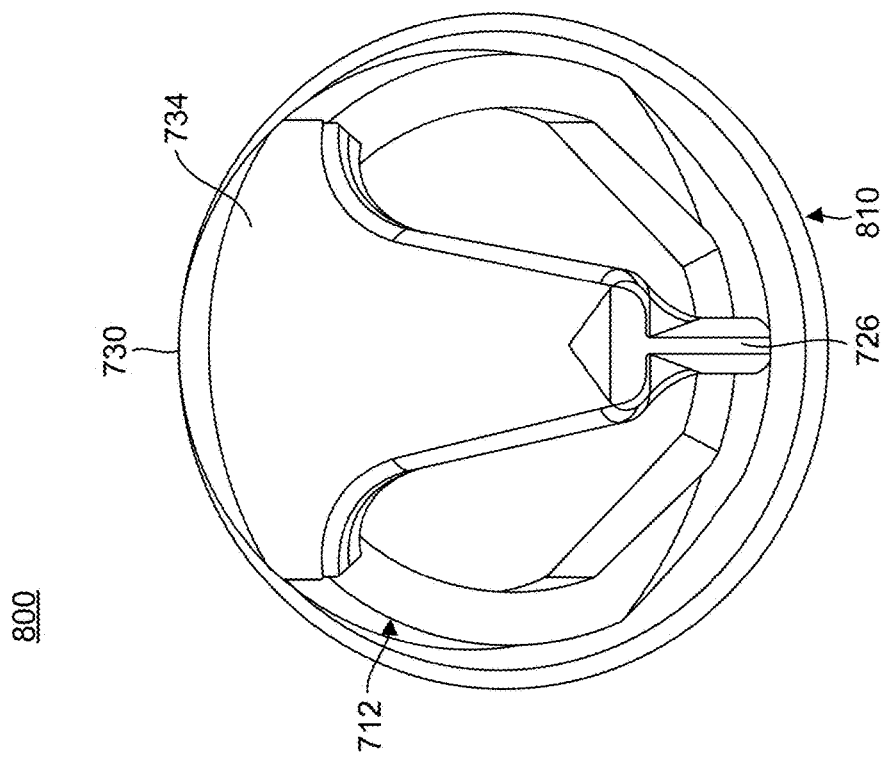
FIG. 97 is a bottom isometric view of the reverse shoulder implant assembly of FIG. 92, in accordance with an aspect of the present invention.
Figure 100:
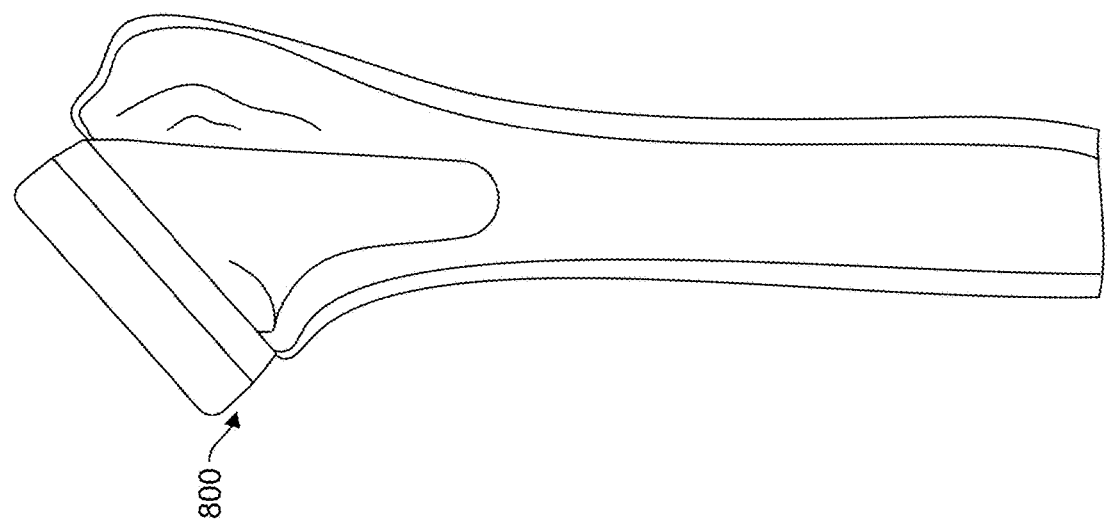
FIG. 100 is a side view of the reverse shoulder implant assembly of FIG. 92 implanted in a bone, in accordance with an aspect of the present invention.
Figure 99:
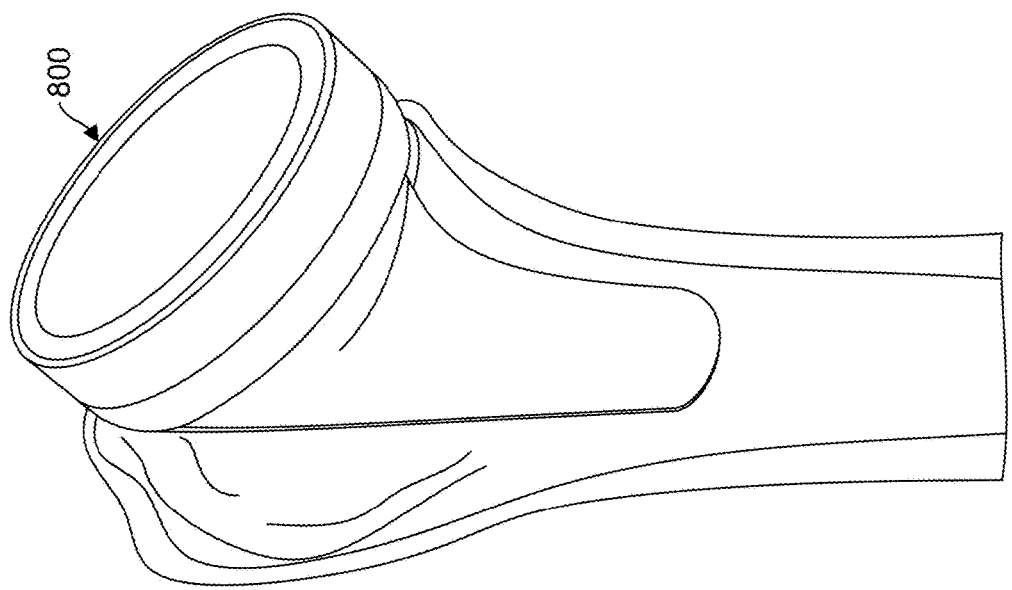
FIG. 99 is a second isometric view of the reverse shoulder implant assembly of FIG. 92 implanted in a bone, in accordance with an aspect of the present invention.
Figure 102:
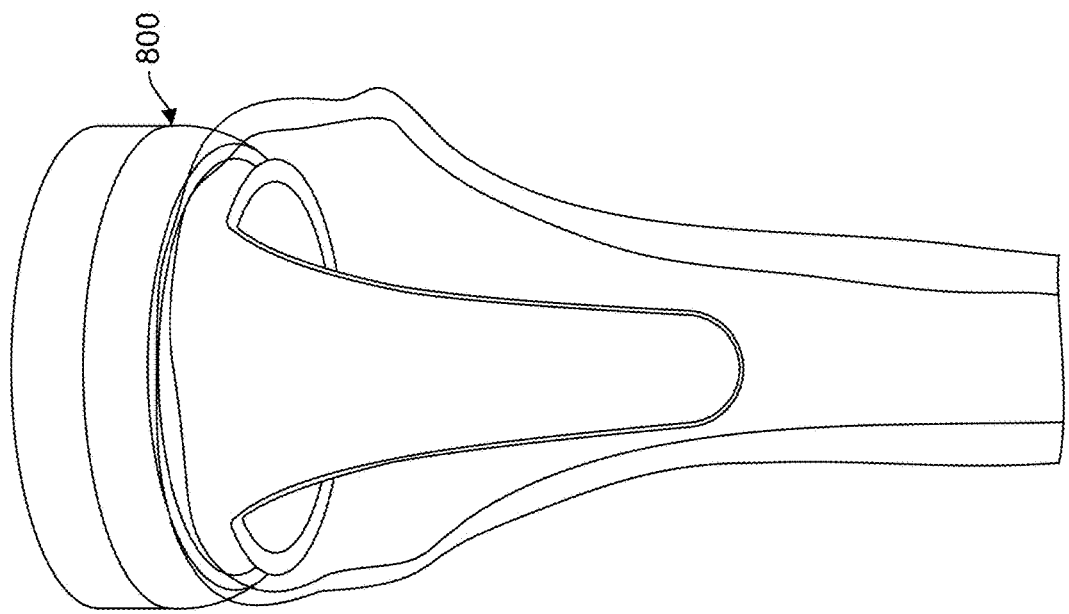
FIG. 102 is a lateral view of the reverse shoulder implant assembly of FIG. 92 implanted in a bone, in accordance with an aspect of the present invention.
Figure 101:
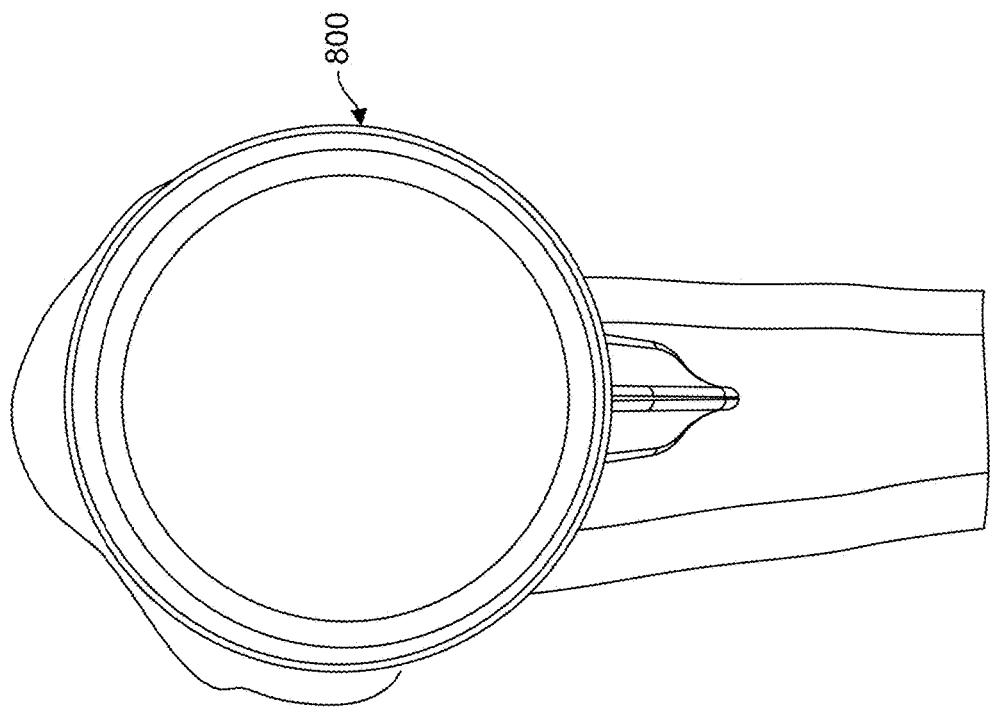
FIG. 101 is a medial view of the reverse shoulder implant assembly of FIG. 92 implanted in a bone, in accordance with an aspect of the present invention.

Referring now to FIGS. 55-67, an orthopedic implant system or stemmed implant system 500 is shown. This stemmed implant system 500 may include a stem component 510, an articulating portion 150 and a coupling member 170. The articulating portion 150 and the coupling member 170 are as described above with reference to implant system 100 and will not be described again here for brevity's sake. As shown in FIGS. 45-54, the stem component 510 may include a first end 512 and a second end 514. The stem component 510 may include a plate or base 516 and a stem 542. The base 516 may have a large ring or surface area to assist with fixation, for example, the base 516 may contact cancellous bone to provide better support for the implant 500. The base 516 may include a recess or circumferential groove 518 extending into the base 516 from the first end 512. The groove 518 may be, for example, tapered as the groove 518 extends from a first end 512 into the base 516 of the anchor member 510, as shown in FIGS. 63 and 76. The circumferential groove 518 forms an interior lip 520 positioned within the base 516. The base 516 may also include a central member 522 with an opening 524 extending into the central member 522, as shown in FIG. 53. The opening 524 may include a first portion or first wall portion 526 and a threaded portion 528. The first portion 526 may extend from the first end 512 of the stem component 510 toward the second end 514. The threaded portion 528 may be positioned at a bottom of the opening 524. The diameter of the threaded portion 528 may be, for example, smaller than the diameter of the first portion 526.

Figure 50:
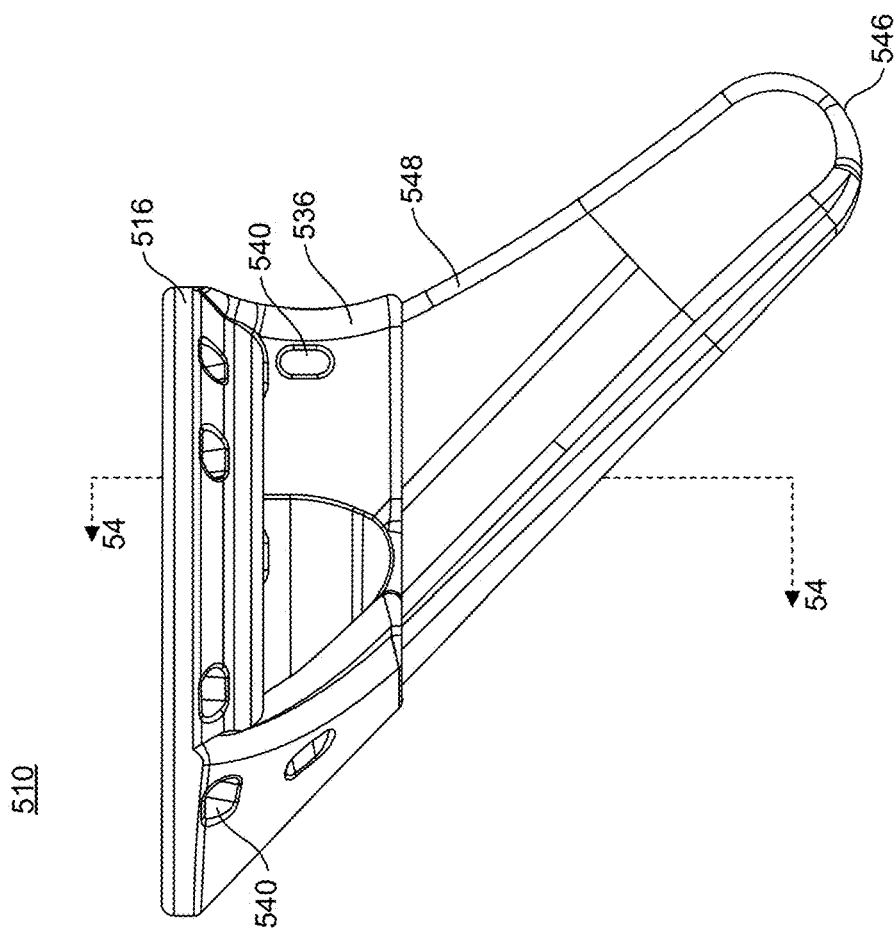
FIG. 50 is a second side view of the stemmed humeral implant of FIG. 45, in accordance with an aspect of the present invention.
Figure 49:
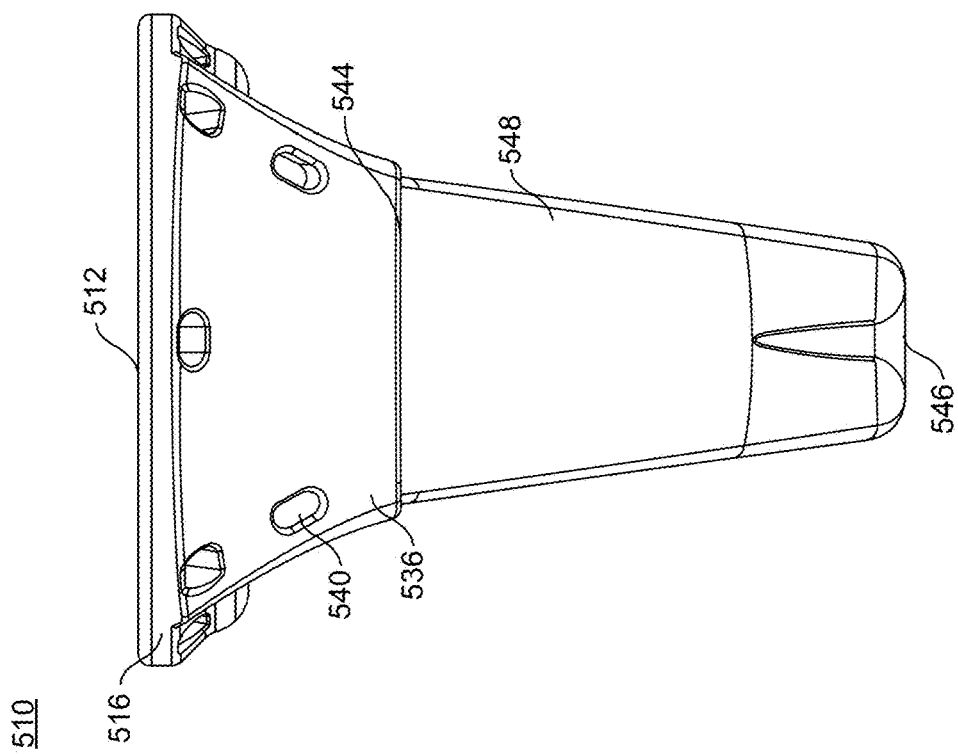
FIG. 49 is a lateral view of the stemmed humeral implant of FIG. 45, in accordance with an aspect of the present invention.
Figure 51:
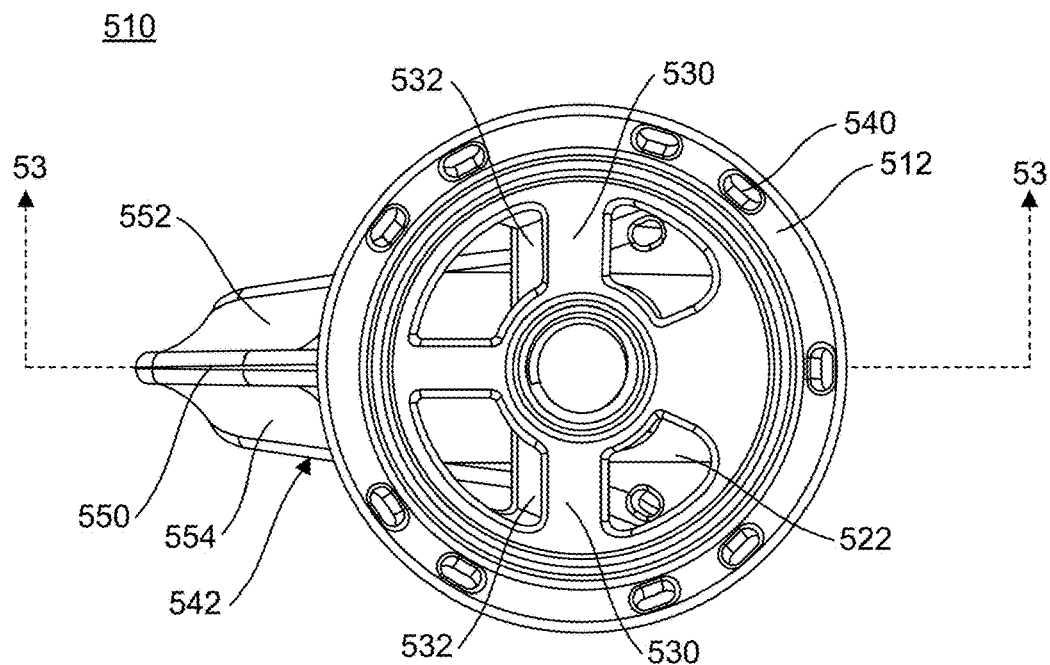
FIG. 51 is a top view of the stemmed humeral implant of FIG. 45, in accordance with an aspect of the present invention.
Figure 52:
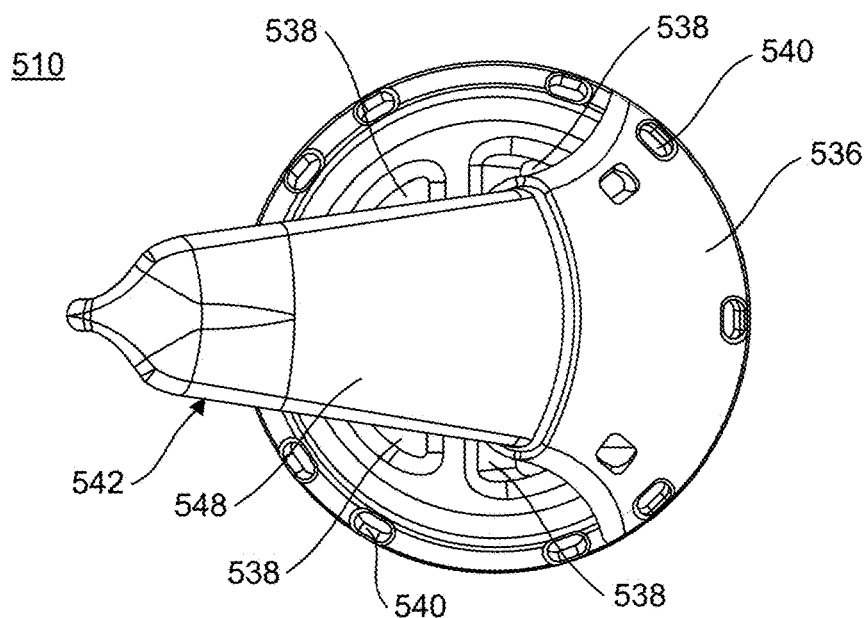
FIG. 52 is a bottom view of the stemmed humeral implant of FIG. 45, in accordance with an aspect of the present invention.
Figure 54:
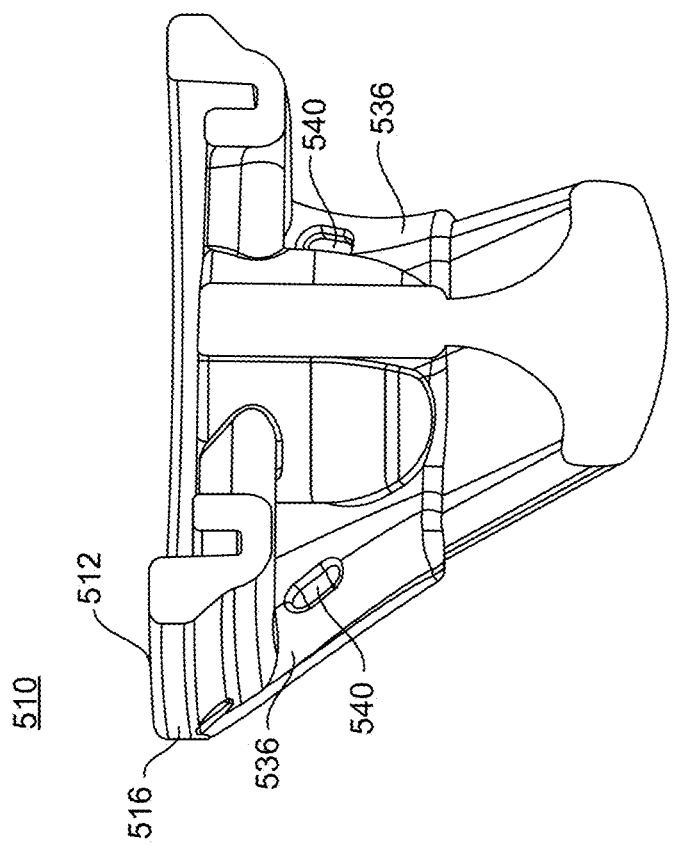
FIG. 54 is a cross-sectional view of the stemmed humeral implant of FIG. 45 taken along line 54-54 in FIG. 50, in accordance with an aspect of the present invention.

With continued reference to FIGS. 45-54, the stem component 510 may also include arms 530 extending between the interior lip 520 and the central member 522. The arms 530 may include, for example, at least one tapered edge 532, as shown in FIG. 51. As shown, the stem component 510 may include two arms 530 which may be positioned on opposite sides of the central member 522. The stem component 510 may also include a first support member 534 and a second support member 536. The first support member 534 may be positioned between the two arms 530. Likewise, the second support member 536 may be positioned between the 2 arms 530 and the second support member 536 may be positioned opposite the first support member 534. The first support member 534 may extend between the first end 512 of the stem component 510 and the stem 542 on a first side. The second support member 536 may extend between the first end 512 and the stem 542 on a second side. The base 516 may also include windows or openings 538 positioned between the arms 530 and support members 534, 536. The openings 538 may extend entirely through the base 516. The base 516 may also include a plurality of fastener openings 540. The plurality of fastener openings 540 may be, for example, configured or sized and shaped to receive fasteners, such as, sutures and the like. The plurality of fastener opening 540 may extend through the base 516 from the first end 512 toward the second end 514. In addition, the plurality of fastener openings 540 may include openings extending through the second support member 536 from an interior surface to an exterior surface.

As also shown in FIGS. 45-54, the stem 542 may include a proximal end 544 coupled to the second support member 536 of the base 516 and a distal end or tip 546 positioned at the second end 514 of the stem component 510. The stem 542 extends away from a bottom surface of the base 516 to the second end 514. The stem 542 may extend away from the base 516 at an angle, as shown in FIGS. 48, 50 and 53. The stem 542 may include an exterior surface 548 and at least one interior surface 552, 554. The stem 542 may also include a fin, legs, or protrusion 550 extending away from the at least one interior surface 552, 554. The fin 550 may be positioned, for example, at a midpoint or midline of the stem 542. The fin 550 may divide the interior surface 552, 554 into a first interior surface 552 and a second interior surface 554. Each interior surface 552, 554 may be, for example, curved or arced from the medial or lateral exterior surface to the fin 550. As shown in at least FIGS. 46 and 54, the stem 542 may have, for example, a "T" shape as the stem 542 extends away from the distal end of the base 516. The exterior surface 548 and at least one interior surface 552, 554 make up the horizontal portion of the "T" shape and the fin 550 makes up the vertical portion of the "T" shape. The stem 542 may be, for example, tapered as it extends away from the proximal end 544.

Referring now to FIGS. 55-67, the assembled stemmed implant system 500 is shown. Specifically, FIG. 63 shows a cross-section of an assembled stemmed implant system 500. The first end 172 of the coupling member 170 is inserted into the opening 160 of the articulating portion 150. The alignment protrusion 180 may be, for example, aligned with at least one slot 164 and inserted into a slot 164 of the at least one slot 164 to prevent rotation of the articulating portion 150 with respect to the coupling member 170. The coupling member 170 may be coupled to the articulating portion 150, for example, with a fastener (not shown), a friction fit, such as, a taper fit, and alternative known methods for coupling articulating portion 152 and stem component 510. The base 516 of the humeral component 510 may be, for example, received within the recessed region 156 of the articulating portion 150, as shown is FIG. 63.

Referring now to FIGS. 68-80 and with continued reference to FIGS. 45-54, a reversed stemmed implant system 600 is shown. The implant system 600 includes a stem component 510, a coupling member or spacer 210, and a socket member 240. The stem component 510 is as described with reference to implant system 500 and which will not be described again here for brevity's sake. The coupling member 210 and the socket member 240 are as described above with reference to implant system 200, which will not be described again here for brevity's sake.

As shown in FIGS. 68-80, the implant system 600 may be assembled by inserting the protrusion 232 of the coupling member 210 into the opening 524 of the stem component 510 and the extension number 224 of the coupling member 210 into the interior of the base 516. Specifically, extension member 224 may be inserted into the recessed region 518 to secure the spacer 210 to the base 516 of the stem component 510 in the reverse implant system 600. In addition, the protrusion 258 of the socket member 240 may be inserted into the through hole 234 of the coupling member 210 and the engagement protrusion 250 may engage the recessed region 218 of the coupling member 210. An O-ring 260 or like coupling member may be positioned within the circumferential groove 220 of the coupling member 210 and the circumferential groove 252 of the socket member 242 secure the socket member 242 the coupling member 210. Finally, a fastener (not shown) may engage the threads 528 of the stem component 510 and the threaded opening 234 of the coupling member 210 to secure the stem component 510 to the coupling member 210.

Referring now to FIGS. 81-91, there are shown several views of stem component 710 in accordance with the present invention. The stem component 710 includes a base 712, a stem 726, and a plate 730.

Referring again to FIGS. 81-91, the base 712 has a proximal surface 714, an opposing distal bone contacting surface 716, and an open center or opening 718. The base 712 also includes a flat anterior segment 720, a flat anterior lateral segment 722, and a flat anterior medial segment 724.

Referring still to FIGS. 81-91, the elongate stem 726 extends across the diameter of the open center of the base 712 such that stem 726 bisects the open center 718 of the base 712 and connects to anterior segment 720. The stem 726 further extends from the base 712 in a direction opposite the proximal surface 714 of the base 712.

With continued reference to FIGS. 81-91, the tapered elongated posterior plate 730 extends medially and laterally from the stem 726. The plate 730 further extends from bone contacting surface 716 of the base 712 in a direction opposite the proximal surface 714 of the base 712. As further illustrated in FIGS. 81-91, the plate 730 is disposed perpendicularly to the stem 726. Moreover, the plate 730 has an anterior face 732 connected to the posterior face 734 of the stem 726.

Referring now to FIGS. 92-102, there are shown several views of a shoulder implant assembly 800 in accordance with the present invention. As illustrated in FIGS. 92-102, the implant assembly 800 generally includes humeral component 710 attached via traditional means known in the art to articular liner 810.

Referring now to FIGS. 98-102, there are shown several views of a shoulder implant assembly 800. As illustrated in FIGS. 98-102, implant assembly 800 includes humeral component or stem component 710 attached via traditional means known in the art to an articular liner 810. It is within the scope of the present invention to provide a system of implants comprising a plurality of stem components, humeral heads, and liners of various sizes.

For illustrative purposes, several views of should implant assembly 800 implanted into a humerus are shown in FIGS. 98-102.

A surgical method for implanting the implant systems 100, 200, 300, 400, 500, 600, 700, 800 may include preparing the patient's joint using cut guides. Next, punches may be used to prepare the interior surfaces of the bone for receiving a stemless component 110, 310 or a stemmed component 510, 710. Using the punches for insertion of the implant systems 100, 200, 300, 400, 500, 600, 700, 800 maximizes bone preservation, especially since additional bone does not need to be removed after the punches are used in order to implant the stemless components 110, 310 or the stemmed components 510, 710. Once the bones are prepared, the implant systems 100, 200, 300, 400, 500, 600, 700, 800 may be inserted or coupled to the bones. Since the instruments and preparation technique are the same to this point for both the stemless and stemmed implants, either a stemless implant 100, 200, 300, 400 or stemmed implant 500, 600, 700, 800 may now be inserted into the prepared bone. The stemless implants 100, 200 may be inserted at an insertion angle which is, for example, in a generally perpendicular orientation. As shown in FIGS. 37 and 44, the stemless implants 300, 400 may be inserted at an insertion angle which is, for example, in a vertical orientation with respect to the axis of the canal of the humerus. As shown in FIGS. 98-102, the stemmed implants 500, 600, 700, 800 may be inserted at an insertion angle which is, for example, in a generally vertical orientation.

When inserted into a patient's bone, the base 116, 516 each include a large ring extending away from the groove 118, 518 and the large ring should be placed into contact with cancellous bone to provide better support for the implant 100, 200, 300, 400, 500, 600, 700, 800. Once placed in the desired position, the anchor members 110, 510 of the implants 100, 200, 300, 400, 500, 600, 700, 800 may be, for example, sutured in place. Next, for an anatomic implant 100, 300, 500, 800 the coupling member 170 with the tapered second portion 182 engaging the tapered through hole 124 in the anchor member 110, 510 may be used to secure the anchor member 110, 510 to the articulating portion 150. Alternatively, for a reverse implant 200, 400, 600, 800 the coupling member 210 with the tapered extension member 224 engaging the tapered groove 118 of the anchor member 110, 510 may be used to secure the anchor member 110, 510 to the socket member 240. Finally, the patient's incision may be closed.

As may be recognized by those of ordinary skill in the art based on the teachings herein, numerous changes and modifications may be made to the above-described and other embodiments of the present disclosure without departing from the scope of the disclosure. The components of the implants, devices, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants, devices, and/or systems may include more or fewer components or features than the embodiments as described and illustrated herein. For example, the components and features of implants 100, 200, 300, 400, 500, 600, 700, 800 may be used interchangeably and in alternative combinations as would be modified or altered by one of skill in the art. Further, the steps of the surgical methods associated with the implants 100, 200, 300, 400, 500, 600, 700, 800 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. An anchor for use in an orthopedic implant assembly, the anchor comprising:
   a base including a proximal surface, an opposing distal bone contacting surface, and a central opening;
   a first keel extending across a diameter of the central opening of the base in a direction opposite the proximal surface, and the first keel having a length;
   a second keel extending from the base in a direction opposite the bone contacting surface, and the second keel having a length, wherein the second keel length is the same length or smaller than the length of the first keel;
   a third keel extending from the base in a direction opposite the bone contacting surface, the third keel disposed medially of the first keel, and the third keel including a length, wherein the length of the third keel is the same length or smaller than the length of the first keel; and
   a fourth keel extending from the base in a direction opposite the bone contacting surface, the fourth keel disposed laterally of the first keel and the fourth keel including a length, wherein the length of the fourth keel is the same length or smaller than the length of the first keel;
   wherein each keel further comprises:
      a proximal end; and
      a distal end;
      wherein the base is disposed at a constant angle relative to the proximal end of each keel.

2. The anchor of claim 1, wherein said first keel comprises a plurality of bone engaging fins extending from said first keel.

3. The anchor of claim 2, wherein said first keel has a constant width in a direction perpendicular to said plurality of bone engaging fins of said first keel.

4. The anchor of claim 1, wherein said second keel comprises a plurality of bone engaging fins extending from said second keel.

5. The anchor of claim 1, wherein said third keel comprises a plurality of bone engaging fins extending from said third keel.

6. The anchor of claim 1, wherein said fourth keel comprises a plurality of bone engaging fins extending from said fourth keel.

7. The anchor of claim 1, wherein each of said keels comprises a plurality of bone engaging fins extending from said keels and wherein said plurality of bone engaging fins of said second keel, third keel, and fourth keel are oriented perpendicularly relative to said plurality of bone engaging fins of said first keel.

8. The anchor of claim 7, wherein said first keel has a constant width in a direction perpendicular to said fins of said first keel.

9. The anchor of claim 1, wherein said first keel length is no more than 45 mm from said bone contacting surface of said base.

10. The anchor of claim 1, wherein said first keel length is no more than 40 mm from said bone contacting surface of said base.

11. The anchor of claim 1, wherein said first keel length is no more than 35 mm from said bone contacting surface of said base.

12. The anchor of claim 1, wherein said first keel length is no more than 30 mm from said bone contacting surface of said base.

13. An orthopedic implant assembly, said assembly comprising:
an anchor for use in the orthopedic implant assembly, said anchor adapted to be inserted into a humeral bone, said anchor comprising:
a base, said base having a proximal surface, an opposing distal bone contacting surface, and an open center;
a first keel, said first keel extending across a diameter of said open center of said base, said first keel extending from said base in a direction opposite said proximal surface;
a second keel, said second keel extending from said base in a direction opposite said bone contacting surface, said second keel;
a third keel, said third keel extending from said base in a direction opposite said bone contacting surface, said third keel disposed medially of said first keel;
a fourth keel, said fourth keel extending from said base in a direction opposite said bone contacting surface, said fourth keel disposed laterally of said first keel;
wherein each keel further comprises a proximal end and a distal end and said base is disposed at a constant angle relative to the proximal end of each said keel; and
a humeral head, said humeral head attached to said proximal surface of said anchor.

14. The anchor of claim 13, wherein said first keel comprises a plurality of bone engaging fins extending from said first keel.

15. The anchor of claim 14, wherein said first keel has a constant width in a direction perpendicular to said plurality of bone engaging fins of said first keel.

16. The anchor of claim 13, wherein said second keel comprises a plurality of bone engaging fins extending from said second keel.

17. The anchor of claim 13, wherein said third keel comprises a plurality of bone engaging fins extending from said third keel.

18. The anchor of claim 13, wherein said fourth keel comprises a plurality of bone engaging fins extending from said fourth keel.

19. The anchor of claim 13, wherein each of said keels comprises a plurality of bone engaging fins extending from said keels and wherein said plurality of bone engaging fins of said second keel, third keel, and fourth keel are oriented perpendicularly relative to said plurality of bone engaging fins of said first keel.

20. The anchor of claim 13, wherein said first keel has a constant width in a direction perpendicular to said plurality of bone engaging fins of said first keel.

21. An orthopedic implant assembly, said assembly comprising:
an anchor for use in the orthopedic implant assembly, said anchor adapted to be inserted into a humeral bone, said anchor comprising:
a base, said base having a proximal surface, an opposing distal bone contacting surface, and an open center;
a first keel, said first keel extending across a diameter of said open center of said base, said first keel extending from said base in a direction opposite said proximal surface;
a second keel, said second keel extending from said base in a direction opposite said bone contacting surface, said second keel;
a third keel, said third keel extending from said base in a direction opposite said bone contacting surface, said third keel disposed medially of said first keel;
a fourth keel, said fourth keel extending from said base in a direction opposite said bone contacting surface, said fourth keel disposed laterally of said first keel;
wherein each keel further comprises a proximal end and a distal end and said base is disposed at a constant angle relative to the proximal end of each said keel; and
an articular liner, said articular liner having a concave articular surface, said liner attached to said proximal surface of said anchor.

22. The anchor of claim 21, wherein said first keel length is no more than 45 mm from said bone contacting surface of said base.

23. The anchor of claim 21, wherein said first keel length is no more than 40 mm from said bone contacting surface of said base.

24. The anchor of claim 21, wherein said first keel length is no more than 35 mm from said bone contacting surface of said base.

25. The anchor of claim 21, wherein said first keel length is no more than 30 mm from said bone contacting surface of said base.

26. The anchor of claim 21, wherein said first keel comprises a plurality of bone engaging fins extending from said first keel.

27. The anchor of claim 26, wherein said first keel has a constant width in a direction perpendicular to said plurality of bone engaging fins of said first keel.

28. The anchor of claim 21, wherein said second keel comprises a plurality of bone engaging fins extending from said second keel.

29. The anchor of claim 21, wherein said third keel comprises a plurality of bone engaging fins extending from said third keel.

30. The anchor of claim 21, wherein said fourth keel comprises a plurality of bone engaging fins extending from said fourth keel.

31. The anchor of claim 21, wherein each of said keels comprises a plurality of bone engaging fins extending from said keels and wherein said fins of said second keel, third keel, and fourth keel are oriented perpendicularly relative to said plurality of bone engaging fins of said first keel.

32. The anchor of claim 31, wherein said first keel has a constant width in a direction perpendicular to said plurality of bone engaging fins of said first keel.

* * * * *